(12) United States Patent
Treco et al.

(10) Patent No.: US 6,270,989 B1
(45) Date of Patent: *Aug. 7, 2001

(54) PROTEIN PRODUCTION AND DELIVERY

(75) Inventors: Douglas A. Treco, Arlington; Michael W. Heartlein, Boxborough; Brian M. Hauge, Beverly; Richard F Selden, Wellesley, all of MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/406,030

(22) Filed: Mar. 17, 1995

Related U.S. Application Data

(63) Continuation-in-part of application No. 08/243,391, filed on May 13, 1994, now Pat. No. 5,641,670, which is a continuation-in-part of application No. 07/985,586, filed on Dec. 3, 1992, now abandoned, and a continuation-in-part of application No. 07/911,533, filed on Jul. 10, 1992, now abandoned, and a continuation-in-part of application No. 07/787, 840, filed on Nov. 5, 1991, now abandoned, and a continuation-in-part of application No. 07/789,188, filed on Nov. 5, 1991, now abandoned.

(51) Int. Cl.[7] .................................................. C12P 21/02

(52) U.S. Cl. .................. 435/69.1; 435/69.4; 435/69.51; 435/69.6; 435/69.7; 435/463; 435/367; 435/371; 435/372.3; 435/346; 435/208; 536/23.4; 536/23.51; 536/24.1; 530/350

(58) Field of Search ............................... 435/69.1, 172.3, 435/320.1, 69.6, 463, 367, 371, 372.3, 69.51, 69.4, 69.7, 346, 208; 536/24.1, 23.4, 23.51; 935/22, 34, 36, 41, 47, 52, 59, 66

(56) References Cited

U.S. PATENT DOCUMENTS

| | | |
|---|---|---|
| 4,497,796 | 2/1985 | Salser . |
| 4,703,008 | 10/1987 | Lin ...................................... 435/240.2 |
| 4,751,348 * | 6/1988 | Malmberg et al. ....................... 800/1 |
| 4,789,550 | 12/1988 | Hommel et al. . |
| 4,892,538 | 1/1990 | Aebischer et al. . |
| 5,171,674 * | 12/1992 | Stevens et al. ........................ 435/69.1 |
| 5,236,838 * | 8/1993 | Rasmussen et al. ................... 435/209 |
| 5,272,071 | 12/1993 | Chappel ............................ 435/172.3 |
| 5,356,804 * | 10/1994 | Desnick et al. ....................... 435/208 |
| 5,547,933 | 8/1996 | Lin ............................................ 514/8 |
| 5,578,461 * | 11/1996 | Sherwin et al. ...................... 435/69.1 |
| 5,618,698 | 4/1997 | Lin ....................................... 435/69.4 |
| 5,621,080 | 4/1997 | Lin .......................................... 530/350 |
| 5,641,670 | 6/1997 | Treco et al. ......................... 435/240.2 |
| 5,756,349 | 5/1998 | Lin ........................................ 435/325 |
| 5,789,215 | 8/1998 | Berns et al. ....................... 435/172.3 |
| 5,955,422 | 9/1999 | Lin .......................................... 514/8 |

FOREIGN PATENT DOCUMENTS

| | | | |
|---|---|---|---|
| 0 038 765 | 3/1981 | (EP) . | |
| 0 289 034 | 11/1988 | (EP) . | |
| 0 452 894 | 10/1991 | (EP) . | |
| 2 159 172 | 11/1985 | (GB) . | |
| WO 87/00201 | 1/1987 | (WO) . | |
| WO 88/08306 | 11/1988 | (WO) . | |
| WO 89/01517 | 2/1989 | (WO) . | |
| WO 90/06757 | 6/1990 | (WO) . | |
| WO 90/11354 | 10/1990 | (WO) . | |
| WO91/06666 | 5/1991 | (WO) . | |
| WO91/06667 | 5/1991 | (WO) . | |
| WO 91/09955 | 7/1991 | (WO) . | |
| WO 91/13151 | 9/1991 | (WO) . | |
| WO 91/19796 | 12/1991 | (WO) . | |
| WO 93/03164 * | 2/1993 | (WO) | ............................ C12N/15/90 |
| WO93/09222 | 5/1993 | (WO) . | |
| WO 94/05784 | 3/1994 | (WO) | ............................ C12N/15/09 |
| WO94/10567 | 5/1994 | (WO) | ......................... G01N/33/487 |
| WO94/12650 | 7/1994 | (WO) | ............................ C12N/15/90 |
| WO95/18858 | 7/1995 | (WO) . | |
| WO95/21626 | 8/1995 | (WO) | ............................ A61K/38/19 |
| WO95/31560 | 11/1995 | (WO) | ............................ C12N/15/67 |

OTHER PUBLICATIONS

Alberts, *Molecular Biology of the Cell* (Glossary), third edition, Garland Publishing, Inc., New York.
Antin et al., *Biotechniques* 6:640–42 (1988).
Behr et al., *Proc. Nat'l. Acad. Sci. USA*, 86:6982–86 (1989).
Bennett et al., *Mol. Biol. Med.*, 7:471–77 (1990).
Boggs, S., International Journal of Cell Cloning, 8, 80–96 1990.
Brash et al., *Mol. Cell. Biol.* 7:2031–34 (1987).
Brenner et al., *Mol. Biol. Med.* 7:105–15 (1990).
Brigham et al., *Am. J. Respir. Cell. Mol. Biol.* 1:95–100 (1989).
Burrin et al., *Mol. Endocrinol.* 3:1643–51 (1989).
Cann et al., *Oncogene* 3:123–28 (1988).

(List continued on next page.)

*Primary Examiner*—James Ketter
(74) *Attorney, Agent, or Firm*—Fish & Richardson P.C.

(57) ABSTRACT

The invention relates to novel human DNA sequences, targeting constructs, and methods for producing novel genes encoding thrombopoietin, DNase I, and β-interferon by homologous recombination. The targeting constructs comprise at least: a) a targeting sequence; b) a regulatory sequence; c) an exon; and d) a splice-donor site. The targeting constructs, which can undergo homologous recombination with endogenous cellular sequences to generate a novel gene, are introduced into cells to produce homologously recombinant cells. The homologously recombinant cells are then maintained under conditions which will permit transcription of the novel gene and translation of the mRNA produced, resulting in production of either thrombopoietin, DNase I, or β-interferon. The invention further relates to a methods of producing pharmaceutically useful preparations containing thrombopoietin, DNase I, or β-interferon from homologously recombinant cells and methods of gene therapy comprising administering homologously recombinant cells producing thrombopoietin, DNase I, or β-interferon to a patient for therapeutic purposes.

356 Claims, 30 Drawing Sheets

OTHER PUBLICATIONS

Capecchi, *Science* 244:1288–1292 (1989).
Chang et al., *Biochem. Biophys. Act.* 1092:153–160 (1991).
Chang et al., *Mol. Biol. Med.*, 7:461–70 (1990).
Cline, *Pharmac. Ther.*, 29:69–92 (1986).
Daubas et al., *Nucleic Acids Research*, 16(4) 1251–1271 (1988).
Diatloff–Zito et al., *Proc. Nat'l. Acad. Sci. USA*, 83:7034–38 (1986).
Doering et al., *J. Neurosci. Res.*, 29:292–98 (1991).
Doetschmann et al., *PNAS*, 85:8583–8587 (1988).
Drucker et al., *J. Biol. Chem.* 261:9637–9643 (1986).
Duncan & Reddell, *Biochemistry (Moscow)*, 621263–1274 (1997).
Fountain et al., *Gene*, 68:167–172 (1988).
Friedmann, *Science*, 244:1275–1280 (1989).
Gao et al., *Biochem. Biophys. Res. Commun.*, 179:280–85 (1991).
Gareis et al., *Cell. Mol. Biol.*, 37:191–203 (1991).
Ginot et al., *Eur. J. Biochem.*, 180:289–94 (1989).
Harper et al., *J. Invest. Dermatol.*, 91:150–53 (1988).
Hesse et al., *Proc. Nat'l Acad. Sci. USA*, 83:4312–16 (1986).
Iannuzzi et al., *Am. Rev. Respir. Dis.*, 138:965–68 (1988).
Itzhaki et al., *Nucleic Acids Research*, 19(14) 3835–42 (1991).
Jensen et al., *Exp. Cell Res.*, 189:163–68 (1990).
Keating et al., *Exp. Hematol.*, 18:99–102 (1990).
Keating et al., *Prog. Clin. Biol. Res.*, 333:491–98 (1990).
Kremer et al., *J. Clin. Invest.*, 87:884–93 (1991).
LeMouellic et al., *PNAS*, 87:4712–16 (1990).
Litwer et al., *J. Biol. Chem.*, 264:14597–600 (1988).
Loeffler et al., *J. Neurochem.*, 54:1812–15 (1990).
Lu et al., *Pfugers Arch.*, 415:198–203 (1989).
Mansour et al., *Nature*, 336:348–352 (1988).
Mercola et al., *Ann. NY Acad. Sci.*, 397:272–80 (1982).
Mes–Masson et al., *J. Cell. Sci.*, 94:517–25 (1989).
Narayanan et al., *Biochem. Biophys. Res. Comm.*, 141:1018–24 (1986).
Pasco et al, *DNA*, 8:535–41 (1989).
Ponder et al., *Hum. Gene. Ther.*, 2:41–52 (1991).
Potter, *Anal. Biochem.*, 174:361–73 (1988).
Rippe et al., *Mol. Cell. Biol.*, 10:689–95 (1990).
Robertson, *Biol. Reprod.*, 44:238–45 (1991).
Scharfmann et al., *Proc. Nat'l. Acad. Sci. USA*, 88:4626–30 (1991).
Sedivy et al., *Proc. Nat'l Acad. Sci. USA*, 86:227–231 (1989).
Selden et al., *Science*, 236:714–18 (1987).
Selden et al., *New England Journal of Medicine*, 317(17):1067–76 (1987).
Shesely et al., *Proc. Nat'l Acad. Sci. USA*, 88:4294–98 (1991).
Stacey et al., *Immunol. Cell. Biol.*, 71 (Pt 2):75–85 (1993).
Tatsuka et al., *Exp. Cell Res.*, 178:154–62 (1988).
Thomas et al., *Nature*, 346:847–50 (199).
Thomas et al., *Cell.*, 51:503–512 (1987).
Thompson et al., *Cell.*, 56:313–21 (1989).
Toneguzzo F. & Keating A., *Proc. Nat'l Acad. Sci.*, 83:3496–99 (1986).
Tur–kaspa R. et al., *Mol. Cell. Biol.*, 6:716 (1986).
Vega, *Hum. Genet.*, 87:245–53 (1991).
Verma, *Scientific American*, 68–84 (Nov. 1990).
Vogelstein & Kinzler, *Trends Genet* 9, 138–141 (1993).
Weidle et al., *Gene*, 73:427–37 (1988).
Werner et al., *J. Neurosci. Res.*, 25:50–57 (1990).
Yang et al., *Proc. Nat'l Acad. Sci. USA*, 87:9568–72 (1990).
Zheng et al., *Proc. Nat'l Acad. Sci. USA*, 88:8067–71 (1991).
Capecchi, "Researchers Can Now Create Mice Bearing Any Chosen Mutations In Any Known Gene. The Technology Is Revolutionizing the Study of Mammalian Biology," Scientific American, pp. 52–59, (Mar. 1994).
Capecchi, "The New Mouse Genetics: Altering the Genome By Gene Targeting," Trends in Genetics, 5(3):70–76, (Mar. 1989).
Capecchi, "Altering the Genome By Homologous Recombination," Science, 244:1288–1292, (Jun. 1989).
Darnell et al., "DNA Synthesis, Repair, and Recombination," Molecular Cell Biology, (Scientific American Books distributed by W. H. Freeman and Co., New York, NY), eds.:555–565 (1986).
Folger et al., "Patterns of Integration of DNA Microinjected Into Cultured Mammalian Cells: Evidence for Homologous Recombination Between Injected Plasmid DNA Molecules," Molecular and Cellular Biology, 2(11):1372–1387, (Nov. 1982).
Griffiths et al., "Mechanisms of Genetic Change II: Recombination," An Introduction to Genetic Analysis, $6^{th}$ ed. (W.H. Freeman and Co., New York, NY), Chapter 20:617–636, (1996).
Joyner et al., "Retrovirus Long Terminal Repeats Activate Expression of Coding Sequences for the Herpes Simplex Virus Thymidine Kinase Gene," Proc. Natl. Acad. Sci. USA, 79:1573–1577 (1982).
Kaetzel et al., "Expression of Biologically Active Bovine Luteinizing Hormone In Chinese Hamster Ovary Cells," Proc. Natl. Acad. Sci. USA, 82:7280–7283, (Nov. 1985).
Lin et al., "Cloning and Expression of the Human Erythropoietin Gene," Proc. Natl. Acad. Sci. USA, 82:7580–7584, (Nov. 1985).
Powell et al., "Human Erythropoietin Gene: High Level Expression in Stably Transfected Mammalian Cells and Chromosome Localization," Proc. Natl. Acad. Sci. USA, 83:6465–6469, (Sep. 1986).
Rubnitz et al., "The Minimum Amount of Homology Required for Homologous Recombinations in Mammalian Cells," Molecular and Cellular Biol., 4:2253–2258 (1984).
Smithies et al., "Insertion of DNA Sequences Into the Human Chromosomal βGlobin Locus By Homologous Recombination," Nature, 317:230–234, (1985).
Yanagi et al., "Recombinant Human Erythropoietin Produced by Namalwa Cells," DNA, 8(6):419–427, (1989).
Barton et al., "Replacement Therapy for Inherited Enzyme Deficiency—Macrophage–Targeted . . . " N.E. J. of Medicine 324(21):1464–1470, 1991.*
Furbish et al., "Enzyme replacement therapy in Gaucher's disease: Large–scale purification of . . . " Proc. Nat'l. Acad. Sci. USA 74(8):3560–3563, 1997.*
Goodman and Gilman, *The Pharmacological Basis of Therapeutics*, 8th ed., Pergamon Press, 1990, pp. 1190–119 pp. 1323–1324; p. 1509; p. 1507; pp. 1281–1282; p. 1342.*
J.D. Wilson et al., *Harrison's Principles of Internal Medicine*, 12th ed., McGraw Hill, Inc., NY, 1991, p. 43 and p. 1507.*
Bartley, T.D., et al., "Identification and Cloning of a Megakaryocyte Growth and Development Factor That Is a Ligand for the Cytokine Receptor MpI," *Cell* 77: 1117–1124 (1994).

Selden, R.F. et al., "Implantation of Genetically Engineered Fibroblasts into Mice: Implications for Gene Therapy," *Science*, 236:714–718 (1987).

Zheng, H. et al., "Fidelty of Targeted Recombination in Human Fibroblasts and Murine Embryonic Stem Cells," *Proc. Natl. Acad. Sci., USA*, 88:8067–8071 (1991).

Capecchi, Mario R., "Altering the Genome by Homologous Recombination," *Science*, 244:1288–1292 (1989).

Sedivy, J.M. et al., "Positive Genetic Selection for Gene Disruption in Mammalian Cells by Homologous Recombination," *Proc. Natl. Acad. Sci., USA*, 86:227–231 (1989).

Morgan, J.R. et al., "Expression of an Exogenous Growth Hormone Gene by Transplantable Human Epidermal Cells," *Science*, 237:1476–1479 (1987).

Itzhaki, J.E. et al., "Targeted Disruption of a Human Interferon Inducible Gene Detected by Secretion of Human Growth Hormone," *Nucleic Acids Res.*, 19(4):3835–3842 (1991).

Palmiter, R.D. et al., "Metallothionein–Human GH Fusion Genes Stimulate Growth of Mice," *Science*, 222:809–814 (1983).

Wolff, J.A. et al., "Direct Gene Transfer Into Mouse Muscle In Vivo," *Science*, 247:1465–1468 (1990).

Ponticelli, Claudio and Carati, Stefano, "Correction of Anaemia with Recombinant Human Erythropoietin," *Nephron*, 52:201–208 (1989).

Browne, J.K. et al., "Erythropoietin: Gene Cloning, Protein Structure, and Biological Properties," Cold Spring Harbor Symposia on Quantitative Biology, vol. LI, Cold Spring Harbor Laboratory, pp. 693–702 (1986).

Faulds, D. et al., "Epoetin (Recombinant Human Erythropoietin) Review of Its Pharmacodynamic and Pharmacokinetic Properties and Therapeutic Potential in Anaemia and the Stimulation of Erythropoiesis," *Drugs*, 38(6):863–899 (1989).

Shak, Steven et al., "Recombinant human DNase I reduces the viscosity of cystic fibrosis sputum," *Proc. Natl. Acad. Sci. USA* 87:9188–9192 (1990).

May, Lester T. and Sehgal Pravinkumar B., "On the Relationship Between Human Interferon $\alpha_1$ and $\beta_1$ Genes," *J. of Interferon Research* 5:521–526 (1985).

Fuchs, Henry J. et al., "Effect of Aerosolized Recombinant Human DNase on Exacerbations of Respiratory Symptoms and on Pulmonary Function in Patients with Cystic Fibrosis," *New Eng. J. Med.*,331(10):637–642 (1994).

Kaushansky, Kenneth et al., "Promotion of megakaryocyte progenitor expansion and differentiation by the c–Mpl ligand thrombopoietin," *Letters to Nature*, 369:568–571 (1994).

Lok, Si et al., "Cloning and expression of murine thrombopoietin cDNA and stimulation of platelet production in vivo," *Letters to Nature*, 369:565–568 (1994).

Metcalf, Donald, "Thrombopoietin—at last," *Nature*, 369:519–520 (1994).

de Sauvage, Frederic J. of et al., "Stimulation of megakaryocytopoiesis and thrombopoiesis by the c–Mpl ligand," *Nature*, 369:533–538 (1994).

Foster et al., "Human thrombopoietin: Gene structure, cDNA sequence, expression, and chromosomal localization", Proc. Nat. Acad. Sci. USA 91: 13023–13027, Dec. 1994.*

Sohma et al., "Molecular cloning and chromosomal localization of the human thrombopoietin gene", FEBS Lett. 353: 57–61, 1994.*

Jurka et al., "Reconstruction and analysis of human Alu genes", J. Mol. Evol. 32: 105–121, 1991.*

Claverlie et al., "Alu alert", Nature 371: 752, Oct. 1994.*

ATCC Catalogue of Cell lines & Hybridomas, 1985, pp. 1–5, 42, 67, 85, 139 and 147.*

Li et al., Cancer Research, vol. 50, Sep. 1, 1990, pp. 5328–5332.*

De la Salle et al., Nature, vol. 316, 1985, pp. 268–270.*

Busby et al., Nature vol. 316, 271–273, 1985.*

Pentchev et al., The Journal of Biological Chemistry, vol. 218, 1973, 5256–5261.*

Sorge et al., PNAS, vol. 84, 1987, pp. 906–909.*

Glover (ed.), DNA Cloning vol. II: A Practical Approach, IRL Press, 1985, pp. 144–148.*

Kaufman, Technique, vol. 2, Oct. 1990, pp. 221–236.*

Pecceu et al., Gene, vol. 97, 1991, pp. 253–258.*

Nagy et al., Journal of Cell Science, vol. 87, 1987, pp. 651–655.*

Migliaccio et al., The Journal of Cell Biology, vol. 109, 1989, pp. 833–841.*

Keene et al., The Journal of Biological Chemistry, vol. 264, 1989, pp. 4769–4775.*

McDonald, Experimental Hematology, vol. 16, 1988, pp. 201–205. (in Chemical Abstracts 108:124584).*

Shak et al., PNAS, vol. 87, Dec. 1990, pp. 9188–9192.*

Ohno et al., Nucleic Acids Research, vol. 10, 1982, pp. 967–977.*

Orkin et al., Report and Recommendations of the Panel to Assess the NIH Investment in Research on gene Therapy, NIH, 1995.*

Editorial from Nature Biotechnology, vol. 15, 1997, pp. 815.*

Verma et al., Nature, vol. 389, 1997, pp. 239–242.*

French Anderson, Nature, vol. 392 (Supp), 1998, pp. 25–30.*

ATCC Catalogue of Fungi/Yeasts, 1987, pp. 324–346.*

* cited by examiner

```
         Xbal (-6372)
-6373 TCTAGAGTCAGGATGGCACTGAAGGTCTCTGGGGAAGGGACGATGATGAGAGCCCGTCAGAA

-6311 ACCCTCCCCCCTTTCCTGGGTGATAGAGAAGACTCAGAACTTCACGCCCGGGGCTCTTTGCT

Apal (-6233)
-6249 CCCTACCTGCAGCCAGGGCCCGGTGCGATGAGAGCCCCCAGACCTCCCTGAAGGGTGAGTGA

-6187 GTGTCACAAGTGCCACATGCAGCTGTTCTGCCCTAAGGAGCCGCAGAGACAACCGAGGCACT

-6125 GCCCGCCACACCCCACAGACCTGGAGCAGAGAGACAAGAAGGCCCTACGCTCAGACACTGTG

-6063 CAGGCTAGGCCAATTAGGATGCCCAGGCAGGGCTTATGAAAAAGGAACATGGAAAGGAACCT

HindIII (-5985)
-6001 CCAGGGTGCCCTAGGAAGCTTAAGAAAGAACGCTGGAGCCAGATGCTTGGGTTCCAATCCTG

-5939 GCTGCACCACTTCCTAGCTGTGTGACCTTGAATCAAATCACATTATCCTACTGAGCCTCAGT

-5877 TCCCCCTTCTGTAAAATGGGCATCATAATGTCAGTGCCTTCCTCCCACTGGGCTGTGGTGAG

-5815 GACCACGGGAGGCAATGCAGAGCATGCTCTCGGCACAGTGCCCAGACTGGGCAAGTGCTATA

-5753 AATGGCATCATCTCACCAGGCCTATCTTGGGTTGRGTGGGCTGCAGGGTGCTCAAACAGGAC

BamHI (-5667)
-5691 ACTGCCATTGGAGTCTGAGAAGCGGATCCTGGTAGGGCGGTCCAGCCTGGGAATGAGAGGTC

-5629 GGGTGAGGCCGGACTGAGCCAAAAGCAGCCCCTCCCAGCTCTCCCAGTTTCCCTCCSGGCCC

-5567 CGGCAGCGTGACCCCTCCTTGCTCCTTCCCCTTTCTCACCGCCTGTAGGAGATAGAGAAGCG

-5505 GAGGCTAGAGCGCCAGCAGCGAGACTCGGCTCGTGCCACCGCCTGCGACCTCGGCCCTGTCA

-5443 GCAGCGCCACGAAGTCTGGGACGGGAGGAAGATGGCCTGAGCACTGTCAAACGCCGCTTTGG

-5381 TGGCCCAGCCTCAACCACAACCCCGCTGTTCGCCAGCCCCTACCCGTGTGGCCGTCACCAC

Apal (-5318)
-5319 GGGCCCGCTCCTCAGCGCCTGGCTCCCCGCGGTCGCTATAACTGCGATGCTCCGGGTCCCGC

-5257 GGATACACGAAGGACAGGCCGCTCGGCTGCCGCTCCGAACTGCTGCGCTCTGCGGSGGGGG

-5195 GTAAGAACACGGGCTTCAGCTGGCCATGGGAAAGGCCAGTCCGACGCCCCATCCAAGTGGCC
```

FIG. 4A

-5133 CGGGACCTAGTATCGTGGCCCTGCCTCCCTCCCCGCAGCGGAGCAAGACTTACCCTGGGGC

-5071 AGGTCTGGCAGCAGTGTCCCGGCAGCTGGCGCGGCTGCCCACAGGCCGGGGTTGGGCACTCT

-5009 GGTTTGATGTTCTTGCAGCTGACCCTGCCAGGCCCCTGGTACGGCGACCCCACTGAGGCTGC

-4947 TCCCGGAAAAGGCGGGAAACCCAAGTGAGTGCAAGATGCCAACTGATGAGACCCCCCCAGGC

-4885 AAGGATGTCCCGCAGAGTCAGCCAGCTCTGCCACTTACAAGCTGCGTGACCCTAGACAAGCT

-4823 ACTTCATCTCTCTGGGCCTCAAGGTCCCTGTCTGGAAAATGGGGATAATAATACTCTCTATC

-4761 TAGCAAGGCTGCCATGAGAGTTAGATGAGCAGGGAACGAAACGGAGTTGGCACAGAGCCTCA

-4699 CACAGAGTGGGCGATCAGTAACAGCACCTAAGAATTGGAGGGGCTGATTCCCCTTCCTCCAC

-4637 CAGAAAAATATCCCCAACATCTGCCGACTGGGCTCCTTCTCAGCAGCTCCGAGTCCACTCCG

-4575 ACGCCCGCGCGACCCGGCCGTCCCCACCCGCCAGCCCGGGCCGGCCGCGGGGTGCACTCACC

-4513 GCCTCGCAGGCCACAGCACGCAGCGCATCACCCCGAATGGCTCCCCTAGGTCCGGGTGCCAC

-4451 GTCTCGTCCAAGGCATAGACCTTCCCGCCGAAGTGCAGCCTGCGGGACGGGCTTGGCTGGAG

-4389 GCGCTGCCCAGCTCGCGCCGTGTGCCGCCCCGGGGGCTGCCCGCGGGTCCCGGGTCCCAGGC

-4327 ACCGCGCCCTTCTGCCCCCGCCCACCCTCCGGGCCGCCCGCCGCGCCGAGCCACCTGCGCCC

-4265 CGCGCCCCTCCTCCGGCTCGGCTGACTCGCCCCGAGCCCGACTCCCCGCCCGCCTCCCCCGG

-4203 GCGCCCACCTACCCTGCTGCCCGAACGGGCAGCGGCTCCTTCTCAGAACGGATGGGCAGCAC

SfiI (-4079)

-4141 GGGGGCTCTCGGGCCGCGCGGGGCGGGAGCCGAGCAGCAGCAGCCCGAGGAGCAGCAGCGGG

-4079 GCCGGCGGGGCCGGGAGGGCHCGGCATGACGCGAACGGGACAGCTGGGGAGGAGGGAGGGAG

-4017 GAGGGCGCGGGAGCGGGCGGAGGGAGGGAGGCGGGAGTGCGGAGGGCGGAGGGCCGGGCCGG

-3955 GGGCGGTGCGGCGGGAGGGGCCGGGCCGGGCCGGGCCGGGCAGTGCCCGCGAGGGGC

FIG. 4B

```
         NotI (-3885)
-3893 TCGTCGGGCGGCCGCAGAGTCGGCGCCGGGCCGGGCGGGGCGGGAGGAGCGGCCGGGAGGAG

-3831 CGCGGGCGGGCGGGCGCTGACCCGGGCCGTACGCGGCTCTACTGCCCCGGGCGCCGGCTCCG

-3769 GCCCGTTTTATGCCCCGCGCCCGACGCCCCGGCCGGGGGCCTCCTCCTCAGCAAACGGGGCG

-3707 GCGGCGGCGGCTCGGCGAGGGGCCGCTGAGCCCGGGGGGTCCGACCCAGCAGCAGCGGCCCG

-3645 GATCGCGGGTGGGGGAGGGGAGGGAGGGCTGGGACCGGGCAGGGGAGGAGGGAGGGGCGGGA

-3583 GGGGAAGGGGGAGCGGGGGAGGGGGAGGGGAGGGACCAGGGGGCGCGAAGAGGGGGAGGAGA

-3521 GGCGGCCCGGAGCCCCGCTGCTGGCGGCCACAGGGCGGCTGGACCAGGAGGTCGGTGTCCA

-3459 GCCCAGGAAGGGAGCCTCAGGCTAGGGAGGGGCAGAGGCTTACCTGAGGCCTGGACCGCTCT

-3397 GTGAGCGAGGCCCGGTTCCGCCCGAAGGATAAACTTGTCTTTAAAGATACACGTACAGGAAA

ApaI (-3307)
-3335 GGTCCATCAGCCGATCTCCCCCTGCCTGGGCCCACAGCGCCCCCCAAACCCTCACCACCCTC

-3273 TCTCACTGCCTAGCCTGCCTCCCTACCTTCTCTCTGAGGTCGCTCCTCWTTCTTGTGTTACC

-3211 CAGRACAGGGACCTAGCCAGAAACCGGCAGCATTCCCCCTTCTGTGGAGTGACAGTATCTCC

-3149 CTCTCATTGTAACTTATCCTCAGGCGCATTCGACAGTCCCCTCTTGCTTTCTCACCCCCTTC

-3087 CTTCACCCAAGGGACCCTCTGCCTCTCCAGCCCACTCCCAGCCTCCTTTCTCTTGGTTCCCT

-3025 GGTCATGCCTGCCTCCCTGTCTCCTGTCTCTCCCTCCCACACACACCCACTATCCTCCCAGC

-2963 TATCCCAGCACCCTCCTTCCTAATCTTGGGAGACATCTCGTCTGGCTGGACGGGAAAATTCC

-2901 AGGATCTAGGCCACACTTCTCAGCAGACATGCCCATCCTTGGGGAGGAGGAACAGGAGAGAG

-2839 CCTGAGGAAGTTCTGGGGGACAGGGGGATGATGGGATCAAGGTCAGGCCAGGAAGCCCCTGA

-2777 GGACAGAGACTGTGGGGAGACTTGGGACTGGGAAGAAAGCAAAGGAGCTAGAGCCAGGGCCA

-2715 AAGGAAAAGGGGGGCCAGCAGGGWGGTATTTGCGGGGGAGGTCCAGCAGCTGTCTTTCCTAA
```

FIG. 4C

```
-2653 GACAGGGACACATGGGCCTGGTTATTCCTCTTGTCACATGTGGAACGGTAGGAGATGGAAGA

ApaI (-2568)
-2591 CGGAGACAGAACAAGCAAAGGAGGGCCCTGGGCACAGAGGTCTGTGTGTGTAGCCATCTAAG

-2529 CCACTGGACCCCAGCAGACGAGCACCTAAGCTCAGGCTTAACCAGTGCACGTGTGCGCACAT

-2467 ACTGTGCCCCGCACCTGACGTCCACTCAACCCGTCCAAACCCTTTCCCCATAACACCAACCC

-2405 ATAACAGGAGATTTCTCTCATGTGGGCAATATCCGTGTTCCCACTTCGAAAGGGGGAATGAC

-2343 AAGATAGGACTCCCTAGGGGATTACAGAAAGAAAAGCAGGAAAGCAAGCATCCTGTTGGATT

-2281 TCAGCAGCAGGTATGATGTCCAGGGAAAAGAAATTTGGATAGCCAGGGAGTGAAAACCCCAC

-2219 CAATCTTAAACAAGACCTCTGTGCTTCTTCCCCAGCAACACAAATGTCCTGCCAGATTCCTC

-2157 CTGGAAAAAACTTCTGCTCCTGTCCCCCTCCAGGTCCAGGTTGCCCATGTCCAGGAAAAGAT

BamHI (-2094)
-2095 GGATCCCCCTCATCCAAATCTTCTCCGTGTGTGCTGTGGGTGGAGTGAGTRGWARCCCTGGT

-2033 CCAGGCAGGGVGCTCCAGGGAAGAGCAAGGCGTCACTTCCGGGSGCCTTCACCAGTGTCTGG

-1971 TGGCTCCCTTCTCTGATTGGGCAGAAGTGGCCCAGGCAGAGCGTATGACCTGCTGCTGTGGA

-1909 GGGGCTGTGCCCCACCGCCACATG
```

FIG. 4D

```
-1885  TCTTCCTACCCATCTGCTCCCCAGAGGGCTGCCTGCTGTGCACTTGGGTCCTGGAGCCCTTC

-1823  TCCACCCGGTGAGTGGCCAGCAGGGTGTGGGGTTATGTGAGGGTAGAAAGGACAGCAAAGAG

-1761  AAATGGGCTCCCAGCTGGGGGAGGGGCAGGCAAACTGGAACCTACAGGCACTGACCTTTGTC

-1699  GAGAAGAGTGTAGCCTTCCCAGAATGGGAGGAGCAGGGCAGAGCAGGGGTAGGGGTGGGGT

-1637  GCTGKTTTCCTGAGGGACTGATCACTTACTTGGTGGAATACAGCACAGCCCTGGCTGGCCCT

-1575  AAGGAAAGGGGACATGAGCCCAGGGAGAAAATAAGAGAGGGAGCTGCACTTAGGGCTTAGCA

-1513  AACACAGTAGTAAGATGGACACAGCCCCAATCCCCATTCTTAGCTGGTCATTCCTCGTTAGC

-1451  TTAAGGTTCTGAATCTGGTGCTGGGGAAGCTGGGCCAGGCAAGCCAGGGCGCAAGGAGAGGG

ApaI (-1377)
-1389  TAATGGGAGGAGGGCCCACTCATGTTGACAGACCTACAGGAAATCCCAATATTGAATCAGGT

-1327  GCAAGCCTCTTTGCACAACTTGTGAAAGGAGGAGGAAGCCATGTGGGGGGTCCTGTGAAGGA

-1265  ACCGGAAGGGGTTCTGCCAAGGGGGCAGGGAGGCAGGTGTGAGCTATGAGACAGATATGTTA

-1203  GTGGGCGCCTAAGACAAGGTAAGCCCCTAAGGTGGGCATCACCCAGCAGGTGCCCGTTCCTG

-1141  GGCAGCTGGTTTCAGGAAGGAAGTCCCAGAACTGTTAGCCCATCTCTTGGCCTCAGATAATG

-1079  GAGTATTTCAGGACTTGGAGTCCAGAGAAAAGCTCCAGTGGCTTTATGTGTGGGGGTAGATA

-1017  GGGAAAGAATAGAGGTTAATTTCTCCCATACCGCCTTTTAATCCTGACCTCTAGTGGTCCCA

-955  GTTACAGCTTTGTGCAGTTCCCCTCCCCAGCCCCACTCCCCACCGCAGAAGTTACCCCTCAA

-893  CATATTGCGCCCGTTTGCCAGTTCCTCACCCAGGCCCTGCATCCCATTTTCCACTCTCTTCT

-831  CCAGGCTGAAGCCACAATACTTTCCTTCTCTATCCCCATCCCAGATTTTCTCTGACCTAACA

-769  ACCAAGGTTGCTCAGAATTTAAGGCTAATTAAGATATGTGTGTATACATATCATGTCCTGCT

-707  GCTCTCAGCAGGGGTAGGTGGCACCAAATCCATGTCCGATTCACTGAGGAGTCCTGACAAAA
```

FIG. 5A

```
-645  AGGAGACACCATATGCTTTCTTGCTTTCTTTCTTTCTTTCTTTCTTTCTTTTTTTTTTTTGAG

-582  ACGGAGTTTCACTCTTATTGCCCAGGCTGGAGTGCAATGGTGCGATCTCGGCTCACCACAACC

-519  TCCGCCTCCCAGGTACAAGCGATTCTCCTGTCTCAGCCTCCCAAGTAGCTTGGATTACAGGCA

-456  TGAACCACCACACCCTGCTAGTTTTTTTGTATTTCGTAGAGCCGGGGTTTCACCATGTTAGTG

-393  AGGCTGGTGGCGAACTCCTGACCTCAGGTGATCCACCCGCCTTGGACTCCCAAAGTGCTGGGA

EcoRI (-268)
-330  TTACAGGCATGAGCCACTGCACCCGGCACACCATATGCTTTCATCACAAGRAAATGTGAGAGA

-267  ATTCAGGGCTTTGGCAGTTCCAGGCTGGTCAGCATCTCAAGCCCTCCCCAGCATCTGTTCACC

-204  CTGCCAGGCAGTCTCTTCCTAGAAACTTGGTTAAATGTTCACTCTTCTTGCTACTTTCAGGAT

-141  AGATTCTTCACCCTTGGTCCGCCTTTGCCCCACCCTACTCTGCCCAGAAGTGCAAGAGCCTAA

-78  GCCGCCTCCATGGCCCCAGGAAGGATTCAGGGGAGAGGCCCCAAACAGGGAGCCACGCCAGCC

AUG (1)
 -15  AGACACCCCGGCCAGA ATG GAG CTG ACT G GTGAGAACACACCTGAGGGGCTAGGGCC

43  ATATGGAAACATGACAGAAGGGGAGAGAGAAAGGAGACACGCTGCAGGGGGCAGGAAGCTGGG

106  GGAACCCATTCTCCCAAAAATAAGGGGTCTGAGGGGTGGATTCCCTGGGTTTCAGGTCTGGGT

EcoRI (178)
 169  CCTGAATGGGAATTCCTGGAATACCAGCTGACAATGATTTCCTCCTCATCTTTCAACCTCACC

232  TCTCCTCATCTAAGAA TTG CTC CTC GTG GTC ATG CTT CTC CTA ACT GCA

281  AGG CTA ACG CTG TCC AGC CCG GCT CCT CCT GCT TGT GAC CTC CGA GTC

329  CTC AGT AAA CTG CTT CGT GAC TCC CAT GTC CTT CAC AGC AGA CTG GTG

377  AGAACTCCCAACATTATCCCCTTTATCCGCGTAACTGGTAAGACACCCATACTCCCAGGAAGA

440  CACCATCACTTCCTCTAACTCCTTGACCCAATGACTATTCTTCCCATATTGTCCCCACCTACT

XbaI (562)
 503  GATCACACTCTCTGACAAGGATTATTCTTCACAATACAGCCCGCATTTAAAAGCTCTCGTCTA

566  GAACT
```

FIG. 5B

Restriction Map of the DNaseI 5' Flanking Region Including Exons 1 and 2

```
         HincII (-4511)
-4512    GTCAACCTTCACAGTAATTGCTTGTTCAGTGACTGCCACAACCCAGCCTGGCAGAGAGAGGGAA

-4448    GATACCCTATAAAGCAAGGTAACGTTAATGTTGAGACCATGAATGGCCTTGAGCAGAGCAGAGT

-4384    ATCATTGCTTCCTTCAAAATTCAGAAGGATCTGATGGTGCTCTGTGAGTTCATGGGGGTGCCTC

-4320    CGTGCAGGTTGAAACCACAGCTGTCGTCCTTCCGCTTTCCCTCTTGATCAGTAGAAGGGTACCC

-4256    TCCCTGGCCTGCACGTCGCTGGGTCACACAACACTGGCTGTCGTTGCACAAAGCCACGGCCACC

-4192    AGCGTTCCTTTGAGGCCATTTGTTTCCAGCCATGGTGCCTATAGGATTTTTCCTTTATCCTGTA

-4128    ATTTCAGCCAAATCAGAGCATGTGACCTGGCTTAGATGTCAATATAATTGTTGTTATGTGCTCT

-4064    TTTCCCTTCCTGTGTCTGTGACAGGTTTAATTTAACCTGAGAAGGCTGCAGATCCTCGGGGGTT

-4000    GGTGTAAAAACACCTCATCCTGATCTGAGAAGGCGGTCAGCTTTTCTCCTCGTTGCCGTTGGCT

-3936    GCCAGCACCCATTCTCTGTGGATGTGAAAATCCCAGAAGGGCTGGGCTTCCTTCTTGGCATTCC

ApaI (-3851)
-3872    CCAGGCCTATCTCCAGAGTGGGGCCCAGCATGGGAGGATTGTACCCCACTCACTCCCCTGATGT

-3808    GGGGCTTGGACCTACAGCTCGACAGCACCCATGGAATGTGGGCAGAAGCGACAGCAGCCAACGT

-3744    CCGCCTTGGCCTTAGGGCGGCACGTGTTCTGCTTGTGCCCTGGGAGCCTCCACCTTCCACACTG

-3680    TGGGAAGAGGGTGCCCAGGGAGCTGCAGTCTCTCCAGCCCAGCCCCAGGACGAGGCCCAGGCAG

-3616    CAGAGCCACCCCAGCAGACCTGGCAGTGTGAGAGAAATGCATGTGTATACACTGAGTTTGCAGG

-3552    TGGCTGTTACATGGCAGCATTGACTGACACAGACAGAAAAGAGATCCACGAGGGAGAAGTGAGA

-3488    GTGCTGGAGACTCCAACAAGCCACAGGCTGCAGGGGCAGGATGGCTTCTTAGAAGGTGAATGAT

-3424    TGTTCTGGGAATCTATCAGAGGAAGACATAGAGGCTCCAGACGGTTGAAGGCCCAACAGTGATC

ApaI (-3353)
-3360    CCAGACGGGCCCCATGTCAGACCAGGCTCCTCCAGGGCTGTCGCTGCCCTCACCAAAGCCCGTC

-3296    CTGAGGGCAGCCACACAGCAGGCAGCACTCGCCATTTGTACAAGCGAGGCCCAAGTTCCAGCCT
```

FIG. 10A

```
-3232 TCCTTCTGGCAGGTAGAGGAAGCAGGGGCACTATGCCTGGGAGTTCCTGAAAGCAGATGGGGCA

Espl (-3109)
-3168 GCATTTGGTCAAGAGCCAGGAGGGGATGACAGACCAGAGGGGAACCCTCGTCCCACGTGCTGAG

-3104 CACACGTAGGGGGTTGGGCACTTGCTCTGTGAGCTATAATTGGTGTCCCTGTGCCCCGCCGGAA

-3040 GCTGCACCAGGCAGTTTCTTGGTGGAGGACAGTGGCCGCCCTCTAGCTTTACTCCCTTCCCCGT

-2976 GATGGGTCGCTGTCAGATGTGTGTCCAGGAAAGGCAAACACCAAAGGCAGAGGACTAGTCCCTA

-2912 CACCGAATACTCCGGTGGCCTTGCTTGGGGCTGGGTTTTGACGTGCTGGAGGCTGTCCTAGAC

-2848 TTAGAGATTAAAAACAGGGAAGAACCATTGCTGAAACCTTTGGAAAAGCCTGCAATGGCCTCTG

-2784 GCAGCCTGAGGAGTGGTGGTGTTTCCATCTGGTAGACGCCGTCTCAATAGGAGGGACAGATGAG

-2720 TGCACCAGTGCTGCCAGCCAGAGGCGTCTGTTGGCGTGTCTTTATGGAATGGGGTGCCAGTCTT

-2656 GTGGAGGGTGGTTTACCTTCCTGTTTCTAGTCCCCACTGGGCCTGCCTTCTGCTTCATGCCAGC

-2592 TGGCCAGACCGAGCACTTTCCTGACTTTCGACCTTGGCCCCTGCTGACTCTTGCCGTTGAGGCC

-2528 TCCTGCAGACCCCATTTGTATTCATTTCCTGCAGTTCTCATACCTGAATCCCGCCTGGACTTCT

-2464 GCCAACCGTTCCAGGCCCTCCTCCCAGGGGACCACAGATGCTACGTGCAGGGCTGTCCTTGGA

-2400 GGGCCAGCACAGCCCCTTCCAAGTGGGCAAGACCCAGGGGTGGCTCAAAAGATAGCTGTGCCCT

-2336 AGCCCTGGAACCTCTGAATGTTGATTTTTGTAGCAAAAAAGGACTTGCAGATGTGAGTAAAGGC

-2272 TGTTGAGATAAGGACATCCTCCCTGCTCTCTGGGAGGACCCCAAATGCAGGTGCACAGATCTTA

-2208 AGAAGAAGAGGCAGAGACTGGGGTGATGCAGCCACAACTAAGGAAAGCCAAGGATTGCTGGCAG

-2144 CCTGCAGAAACTGGAGGGCAAGGAGCATCCCCCAACCGCCCGGAGCCTCCAGGAGGCGCAAGGT

BamHI (-2032)
-2080 CCTACTGACTCCCTGACTTCAGACGTCCAGTCTCCGGAATTTTGAGAGGATCCATTTCTGTTAT

-2016 TTTAAGCAACCAAACTTGTGGTAGTTTCACCAGTCTCAGGAAATGAATACGAATGGAAAGTCAA
```

FIG. 10B

```
-1952  AGATTCCAAGAAATGAGTGGCGGGGTGCGGTGGCTCACACTTGTAATCCCAGCATTTGCGGGAA

-1888  GATTGCTTGGGCTCAGGACTTGGAGACCTTGTGTCTGTGAGAAACTTAAAAAATAGGCTGGGTG

-1824  CGATCGTCACGCCTGTAATCCCAGCACTTTGGGAGGCCGAGGCAGGCGGATCACAAGGTCACGA

-1760  GTTTGAGACCAGTGTGACCAACATGGTGAAACCCTGTCTCTACTAAAAATACAAAAATTAGCCG

-1696  GGTGTGGTGGTGCGTGCCTGTAATCCCAGCTACTCGGGAGGCTGAGGCAGAAGAATTGCTTGAA

-1632  CCCAGGAAGCAGAGGTTGCAGTGAGCCGAGATAGTATTACTGCACTCCAGGCTGGGCAGCAGAG

SphI (-1509)
-1568  CAAGATTCCGCCTCAAAAAAAAAAAAAAAAAAAAAAAAAAAAAAAAACTGAGCATGGTAGCATGC

-1504  ACCTGTGGTCCTCGTACGCCGGAGGATTGCCTGAAGCCAGGAGTTCAAGACCAGTCTGGACAAA

-1440  AGAGCAAGACCCCATCTCTACCAAAAAAATTTAAAAATTAGCCAGGCATGGTGCCGTACCCATA

-1376  GTCTTAGCTACTCAGGAGGCTGAGGAGGGAGGATTATCTGAGCCTGGCGGTTGAGGCTATAATG

-1312  AGCCATGATTTGGCCACTGCACTCCAGCCTTGGCAACACAGTGTGAGACCCTGTCTCAAAAACA

-1248  ATAAAAACCCAAAACAAAAGAACCAAGAAATTACTGGACCTGAGCCTGGCCTTTAGCTGCTGCC

BamHI (-1162)
-1184  CTGCCCTKTGACTGGTCACTCGGATCCCTGGGCCTAAACACACAGCCTATTGTCTACCTCAAGA

-1120  AGGCTCCCCACTGCTTGGCTGGCAATTGGGGTGGCTTTGCAGGCCCCACCTGTCCTGGCCCCAC

-1056  GGCGCTGGTGCTGCAGGCCCCCACCACTGCTTGTTCCGAGCTCCCCAGCCTCCTGCAGAGTTGC

-992  CTGCACCTGATGGCGATGAATCAGGAAGGCAGGCGTGTCCTGGGCCACAGAGCAGTCATGCTGT

-928  CAGCCACCAGGGGGCTCCATTTGCAACTTTGGATGTGGCTTTGGCCTCTTTGTCCAAAGTGACC

ApaI (-860)
 -864  TTGGGGCCCCAGACAAGAGACAGGGAGACTGGAGCCCAGCCCCACCCTCCCGCACATACCTGG

-800  CCCATCCCTGCCCTATCCTGGAAGATGGGGGCCACCACACGTRCAAGGGACACGGGATAGGAAC

-736  CTTTGGCCTTGTTATCAGACATTTTAAAACTAAGTGCAAACGTGATTATCAGGTGCAGTTTTTA
```

FIG. 10C

-672 CAGCAGCAAGAAACCTGTGCTTACAGAAAGAAACACGTGCTAGCAACCCACCTATGCGGAAAGCC

-607 ACACAGAGCCATTGTTTTCTGCACTCTCAGGTGACGGCTCACATTTGCCCCAGGGAAGGTCACAG

BamHI (-498)
-542 CTGCCTGAACTTTTAAAACTCCCAGACACGCACTGCCTGTGCAGGATCCGGAGCCCAGCAGCACT

-477 GCCAGGG

FIG. 10D

```
       CAP site (-469)
-470   CCTTGAAGTGCTTCTTCAGAGACCTTTCTTCATAGACTACTTTTTTTTCTTTAAGCAGCAAA

-408   AGGAGAAAATTGTCATCAAAGGATATTCCAGATTCTTGACAGCATTCTCGTCATCTCTGAGG

-346   ACATCACCATCATCTCAGGTGAGCACCAGGTGGAGTGCCTCTGGGTGACTGGCCGGTTTGGA

-284   GCAGGGAGGGAGGCTTAGAGTCTCATCCTCCAGCAGCGAGTGAGGCGGAGGCTCCAGCGTCC

SmaI (-220)
-222   TCCCGGGCGGGTTTTCTGGTGGATGGAGGAGTGACTCGGGGTCCTCTACGTGGTGCCAGCTG

-160   TTTGGCTTTCTGGACGTTGTAGGAAAGGGTTTCCCCCGCCTGCGTCCCCCTGACCTTGAGCT

-98   CCACCAGCCCCTGCCAGCTGGGCTCCAGAAGGCTGGAGTGCTGTGGCAGGGATGACGTCTCA

AUG (1)
 -36   CTTCTGTTATGTCTCTGTGCCCTGTGCTCTCCCAGG ATG AGG GGC ATG AAG CTG

19   CTG GGG GCG CTG CTG GCA CTG GCG GCC CTA CTG CAG GGG GCC GTG

64   TCC CTG AAG ATC GCA GCC TTC AAC ATC CAG ACA TTT GGG GAG ACC

109   AAG ATG TCC AAT GCC ACC CTC GTC AGC TAC ATT GTG CAG ATC CTG

154   AGC CGC TAT GAC ATC GCC CTG GTC CAG GAG GTC AGA GAC AGC CAC

199   CTG ACT GCC GTG GGG AAG CTG CTG GAC AAC CTC AAT CAG GAT GCA

244   CCA GAC ACC TAT CAC TAC GTG GTC AGT GAG CCA CTG GGA CGG AAC

289   AGC TAT AAG GAG CGC TAC CTG TTC GTG TAC AGG CCT GAC CAG GTG

334   TCT GCG G
```

FIG. 11

```
-8711  AGCTTCTGCTTTAGGAAAGTAGAAAAATAAGAGCAAATTAAATCCAAGGTAAGTAAAAAAAAAA

-8646  AAAAAAAAAAAAGAAATAAAAATTAGAGCAGAAATCAATAAAATTGAAGACAGTAAATCAATAAA

-8581  GAAAATCAACATAAAAAGTCTGGTTCTTGAAAAGATATATAAAATTGATAAGCATCTACCTAGGA

-8516  TAATTAAGGAAAAAGACAGAGGACACAGATTACTAATATCAAACATAAAAGCGGGAACATCACT

-8451  GCAAATTTTATAGGCATTGAAAGCGTAATAAAAGAATACTATAAACTATTCTATAACTACAAATT

-8386  TGATAAGTAAATAGAATGAACCAATTCCTTGAAAGACATAATCTGAAAAATGTAAAAGAAGAAA

-8321  TAAACAATCTGAATAGCCTATATCTATTAAATAAATTGAATCAGTAATTAATAACCTCTCAAAAC

EcoRI (-8223)
-8256  AGGAAGCACAATGCCCAGATGGGTTCACTAGTGAATTCTATCAAATATTTAAAGAAAAAAAATT

-8191  GTATCAACTTTCTACAATCTCTTTCAGAAGACAGAAGCAGAGGGAATACTTCCTAAATCATTCAA

-8126  CTAGGCCAGCATTACCTTAATACCGGAACTAGAAAATGACATTACAAGAAAAGAAAACAACAGAC

-8061  CAATATCTCTCATGAACAAAGATACAAACATTTTCAACAAAATATTAGCAAAAGAATCCAAGAA

-7996  TGTATCAAAAATATACACCACAACCAAGTAGAATTTATTCCAGATATGTAAGGGTGGTTCAACG

-7931  TTTGAAAATCAATTAACGTAATTTGTCCCATCAACAGGTTAAAGAAGAAAATCACATGGTCATAT

-7866  TGATAGACACAGAAAAGCATTTGACAAAATTTAACACCCATTCATGATGCAATCTCTCAGTAAA

-7801  CTAGGAATAGAGGAAAACTTCCTCAGCTTGAATGTACCTTCCTCTCAATTTTGCTATGAACCTGA

-7736  AACTCCTCTTAAAAAATAAAGTTTTTCATTTAAAAAGAAAACAAAAAACATGGAGGAGCGTTGAT

-7671  GTATCTCATTTTAGACCAATCAGCTATGGATAGTTAGGCGACAGCACAGATAGCTGCTGTACTTC

-7606  TGTTTCTGGCAATGTTCCAGACTACATTTAAAAAATTTTTAATTATAGACTTGTACTTAATGTTC

-7541  AAGAAAAATATGAAAATGCTTTGCCGTGTTAATGCTACTCTTTTTTAAAAAAAACTAAAGTTCAA

-7476  ACTTTATTTATATTTCATTAGTTTTTTAGCTACTGTTCTTTTTCTGTTCTGGGATCTCATTCAGA
```

FIG. 14A

-7411  ATGCCACATTACATATAATTCTCATGTCTCCTTGGGTTCCTCTTAGTTTTGACAGTTCCTCAGAC

-7346  TTTTCTTATTTTTGATGACCTTGACAGTTTTGAGGAGTACTGGTTAGATATAGGGTAATGGTTTT

-7281  TAAAGTATATTTGTCATGATTTATACTGGGTAAGGGTTTGGGAGGAAGCCATGGGTAAGTACTGT

-7216  TCTCATCACATCATATCAAGTTATATACCATCAATATTGCCACAGATGTTACTTAGCCTTTTAAT

-7151  ATTTCTCTAATTTAGTGTATATGCAATGATAGTTCTCTGATTTCTGAGATTGAGTTTCTCATGTG

-7086  TAATGATTATTTAGAGTTTCTCTTTCATCTGTTCAAATTTTGTCTAGTTTTATTTTTTACTGATT

-7021  TGTAAGACTTCTTTTTATAATCTGCATATTACAATTCTCTTTACTGGGGGTGTTGCAAATATTTT

-6956  CTGTCATTCTATGGCCTGACTTTTCTTAATGGTTTTTTAATTTTAAAAATAAGTCTTAATATTCA

-6891  TGCAATCTAATTAACAATCTTTTCTTTGTGGTTAGGACTTTGAGTCATAAGAAATTTTTCTCTAC

-6826  ACTGAAGTCATGATGGCATGCTTCTATATTATTTTCTAAAAGATTTAAAGTTTTGCCTTCTCCAT

-6761  TTAGACTTATAATTCACTGGAATTTTTTTGTGTGTATGGTATGACATATGGGTTCCCTTTTATTT

-6696  TTTACATATAAATATATTTCCCTGTTTTTCTAAAAAAGAAAAAGATCATCATTTTCCCATTGTAA

-6631  AATGCCATATTTTTTTCATAGGTCACTTACATATATCAATGGGTCTGTTTCTGAGCTCTACTCTA

-6566  TTTATCAGCCTCACTGTCTATCCCCACACATCTCATGCTTTGCTCTAAATCTTGATATTTAGTGG

-6501  AACATTCTTTCCCATTTTGTTCTACAAGAATATTTTTGTTATTGTCTTTTGGGCTTCTATATACA

-6436  TTTTAGAATGAGGTTGGCAAGTTAACAAACAGCTTTTTTGGGGTGAACATATTGACTACAAATTT

-6371  ATGTGAAAAGAAAGTATACCTTCACAATATTAAGTCTTTTAGTTCATGAATATAGTATGTCTCTC

BglII (-6248)
-6306  CGTTTCTGCATTAACTTAGACATTCATTAATTTCTCTCACAATTTATAAGTTTATTTAGATCTTC

-6241  ATTCATTTAAATCTTCACTAACCTCTCATTTACAATTTGTAAGTTTTCTGGGTAACAGTCTTGCA

-6176  CTTCTTTGCCTAGATTTATTTCCAAGTAGATTATTTTCATACATCGTCTATGGTGTCATTTTTAA

FIG. 14B

```
-6111  AATGTAATTTTTCACCTTTTTATTGCTAAAGAGAGATGACTGATTGTTAATATTGATCTTGTGCG

EcoRI (-6032)
-6046  TGGCGACCTTGCTGAATTCTAATCGTTTATCTATAAATTCTTTTGTATTTTGAATGTAAACAATT

-5981  AGATCATCTGCATATAATTTTTAAAATCTGATAAGTCAACAAGAGATTGAAACAGGCTCTTCACA

-5916  AAGAAAATATCCAAATGGTCAATAAACATATGAAAAGATGCTGAAACTTGTTAATAATCAGAGAG

-5851  ATGCAAATTAAACTATAATGAAGTATTATTGTACAACAATAGAATGACTGAAATTAAAAAGACTG

-5786  ACAATATCAAAGTTGGCAAGAGTCTGATACAACTGGAACTTCTCAAACACTGTTAGTAAGAATGT

-5721  AAATTGGTACAAACATTTGGGAAGTCATTACAATATTATCTGCTAAATCTGAACATATACATATT

-5656  CTATGAGCCAGTTACTTCATTCTAGGCATATACCCAAAAGAAGTATGTACTATTGTGCAGTAAAA

-5591  AATACAGACAAGGAATTTCATAGGAGCATTAATTATCATGGCAAATATTTTAAAAAATTATTAGT

-5526  AGTAGAAGGGATAAAACATTGTGGTATACTTCTAAATAGGGTAAAACACATTAATGTAAATTAAT

-5461  AAACTATACACACAAGATAGACGAATTTCGCAGACATTCTGTTGAGGGTAAGAAGACCATTTATA

-5396  CAAAGCTCAAAAACAGACAGAATCTAGAGTGTTAAAAGACTGCATGGTAGTGACTTTGGGAGAAG

-5331  AAAGTAGTGACGAGAGAGAGGAGAGAGAATAATGATTGCGAGGTGCTATAGTCTGAAGGTTTGTG

-5266  TCCCCCAAATTTCACATGTTAAAACCTAATCCCCAATGCAATCATTTTAAGAAGTGGGTCCTTTA

-5201  GTGGATAATTAGGTAATGGAACAAGAGCCCTAACAAATGGGATTGGTGCCTTATAAAAGAAGCCT

-5136  GAGCCTGAGGGACCTTGTTTCCCGCTTCTACCATATGAGAATGCAATGAGAAGGCACAAAGCAAA

-5071  GAGCAAGCCCTCATCAGACACTGAATCTGCTAGGGCCTTAGTCTTGGCTTTTCCAACCTCCAGAA

-5006  CTATAAAAAGAAATGCTTGTTGTTTAAAAGGCATTCAGTCTATCGGTGTTTTGTTAGAGCAGCCC

-4941  CAAGAGACTTAAGAGGGAACAAGAGGGCGATTTCTGTTGTGTTGATAATGTTTAGTTTGTGGTTA

-4876  CAAAGAGTGCAGACGTTTTTATTTTATAACAATTCATTGAGCTATATCTTAAGATGTATGCGTAA
```

FIG. 14C

```
                                                            EcoRI (-4759)
-4811  TTTTCTATGTATATTATTGTTTTATAAACTTTTTCTTAAAAGAGGAAATGGGAATTCTCCCTTTT

-4746  ATGTATTAATCTCTTATGAAAGAGTTTGTTGGCTTCCCAAGATATTTCTGAAAGATTGCTTTTGG

-4681  CTTCATTTATGTTCTGCCACTGCTTATGCACCTCTCAATAACTCTTCATCTTGTATAATTTATCA

-4616  TTCTTTGATAGGGACCCTCTTCCTTGAAAAATAATTGAAGATATAAGGAGGAGGAAGAGAAGACA

-4551  ACTAAATGTTTATTTCTAGATACATAGTAGTCTGCATAGATAATTATATTCAAAAGAGGAGGACA

-4486  AATTGGCTCCTATCTCTGAAATTTATAGAAAAGCATTTCCACATTAAAGTGATTTCAAATGACTA

-4421  GAAATGTCATTCAAGTTTTACTTTCTAAATGTCACTCTGTCTCTCCAAACCTCATTAACCACAAG

-4356  GAACTGGTGCAGGGACTGGAAGTAGTTTTCTCATACAACGGAAAGTTAACGAGGGGAGGAAAGGA

-4291  TGTGTGCAAAAATAACGTCCACAGAAGGGACAAATAACAAAGGGAAAGATGACAGGAAAGGGTTC

-4226  GGGCACTAACCCTTACAATGCAGATACACACTGGGCTGGTCTAAGAAATAGGGTTCCCTGGTAGA

-4161  CAGAAGGTTAAATAAATTTTCCTGGTTATTCTGATACAACTCTAATAAAAGAAGAGAAATGAAGC

-4096  TAAAACTTAAAATGATGTATTTAAAAGGAAGAAATTTTAACCCATTCATAGGTGAGCTTCTGCCA

-4031  AGATTACTACTAATCCTCAGGAGAAGGGGTAGAGGAGAAACTCCATAAAGGCAACTGGAAGTGGA

-3966  GTATTAGGAAGCACCTCAAGAACACAATAGCAGGAAGTAGCTAGAGAACAAAGAGAAGAAAACCA

-3901  GAAAAAAAAAATCCCTTTTTATTTTTCTGTTTCCATTCCTTTGGCTCCATTTCCACAGCTATGGC

-3836  CTTTATTTTCACCCTCCACAGCCATGAGAGCCTCTGGGCAGGAGTTCTCCTCGCCTCTCCCTGTT

-3771  CCAATCACCTCTAACATTTCTGCCTATTGTTCTGCCCAGGGAAAAAACTCCAGTCTCTTCTCTGT

-3706  CAAAGACCTCTTGAATTAAGTCCAAATGCTACACTCTGGCATTCAAGACTCGTAATACAGCTCAA

-3641  CCTGACTTTTCCACCCTCAGCCTCCTTGATTCCTAAAATGAAGCCTGTCCACAATTGAAGCTCCT

-3576  TGTCTTTGCTCCTGCAAATTTGTTCATTCTCCTGGCTGTGTTTGTGCTGGTCTCTGTCTATCTAG
```

FIG. 14D

```
-3511  AGCTGTGGATATCATGGTATCTATTGTCTATCATGCTAGCCATGAACCACATGTGGCTGGTGAGC

-3446  ATTTTATATGGTACTAGTCTAAATTCACATCTACTGTGAGTGTAAAAATGTGCATTATGTTTTGA

-3381  AGACTGTACACAAAATTTAATTATCTCATGAATAATTTTAGATTGGTTATATGTTGAAATTATAA

-3316  TATTTTGGATATACTATGCTAAATAAAACATATTATTAAAATTAACTTCACCTGTTTCTTTTCCT

-3251  CTTTCAATATGGCTACTAGAGCTTTTTAAATTGCATTATGTGACTTTATTGGACAGTACCGATTG

-3186  AATGCCCTCAACCACATCACCTCACCACAGCCACCTCTACCTGTAGTGATCATACCACTTCTTTA

-3121  GGCACACTGCCTGCATTAAGGGCAATGAATGCCTTTTCATCTTCTCCACTAGATGTAGTTTCTTT

-3056  TTTCTTTGAGAGCCATCATCACCATCATGGTTGACACCATGAACCTATCTGAAGATGTCAGCCAT

-2991  AGACTGCTTGATATTCTACAGGAAAGATCACAGTTTTAAGTGCAATCTACCCATGTTATTAGCAG

-2926  TGTGTATCTTTCACACATTACACAGCCTCTCTAAGCCTCATTTCTCTCCTCTGTAAGATGGGGAT

-2861  GATAATAACCCATCTCAAATGTTTACTATGAGGATTATTCAAAGAATGGCAAATAGCAAGTGCTT

-2796  AATAAATGATAACTAGTACTACCGCCACTACTGTTGTTTTTATTGTATTAGATTATGAACTCTCT

-2731  AAGGACCATTTCCGGATGGAGGATAAGAGACCATTTGATGTGGGCAGTGATGAGGCCTTCTGTTG

-2666  CACCTGGAAAGGTCAACTATATACAAGCCTGCAAGTCATTCTATAGGAGCAGGCCCCAGTGACCA

-2601  GACTCTATAGACTGTCTCCTCTTTCCTGAGAGGGACAGCCATCTCTAGGTTGACTAACCTCTGAA

-2536  GCTCCTTGCATTGGCTTTTGTGCTATGAGCCATGGATGATTCCAGACTAATCCGAGAATGCTCGT

-2471  CAAAACCCCAAGGAATTACTCAAATACTGACATAACAGACATTTTTGAGTGGAAGAGCCGAGTTT

-2406  TTTTTAATATTCTGAAACTCATTGTTTTTAAAATGCATGAGATGGCCAAGGTCTTGCTAAGAGCT

-2341  GGCCTGCAAAGCGAAAGGCAGAGAGAATGAAACCCATAGAGAGGCAGAATAACCAGAAAGGTTGG

-2276  GACTCGTTTATTTTATAATGTAAATTAGTCTATTATGAAACAATACTTGTTTACTGGTGGAAAAT
```

FIG. 14E

```
-2211  TGGAAAATACAAAGAATAAAAGGAGGAAAAAAATCACTCTTTAGTTTCACAAGCCAAATCAAGCC

-2146  ACTATTAAAATGGTGGTTTACTTCCTTTTATTAATTTTCTGTACATATTTTTGCATAATCATGTT

-2081  GTATGTACAATTTTATGTTCTATTTTTCAATATTAACTGGTGTCTTTCAAATTTCCTAATGACAA

-2016  AAATAATATATGCTCATAATAGAACATTTTAAATGCAAATAAAACAAAATAAATGTTAAAATTTA

-1951  GTAATATTTATTAAATTTTCTCCAAGTGCACGAAATTACAAATGTAACAACCTAATTCCCTAGTG

-1886  GCCTAATAACCCTATTTCCAGACCTCTTCTCATTACAAGGAAAAACTCATATGCAGATAGTTCTA

-1821  AAGGTATGAAGTGAAAAGATAAAGATTTTTCTTCCTTGCTGCATCCTCACCCCATCAGCATTATT

-1756  CCCCAGGGTAACTACTATTAATAGATAGTAATTCTACCCAAAGGAAAAAATCATATGCATATAAC

-1691  AGCATCATATGTATACCTTTCTAGTAACTTACAAAACAAATGATAATATCATATCCTTTCTTATG

PvuII (-1580)
-1626  TGTATTGCTCTTTTCACTAAATGTATCTGTGATATGTGTCTATATCAGCTGATTGTCCTTTTTGA

-1561  TGGCTGAATAATATTCCATCTTGTCCACGTGATAGTATTACTTGACAAGCTCCCTGCTGATGGAC

-1496  ATTTGTCTTTGTTACTATGATAGTAATATAATCAACATTTATATATGTTTTGTATGTATCTATAA

-1431  TACACATGCACATACACATGCATATTTCTGCAGGGATAGCCATAGTAAATAACTAGTAACGGTAT

-1366  TGCAAGTTAAAGGAACAATCTCATTGCTTGAAATTTTAAATTTTGAAATACACTGCCAATTTTCA

-1301  TGGTCTCTCCTTGTAAGCTAGTTTGGGCTTTCTCACAGCATGACAGGCTCAGGGCAGTCAGACCA

-1236  TCCTGGCCAAAGAGCAGAGTGCCACAGACCACAACTGCTTCTAATCAGCCATCTTCCCAAAGCCT

-1171  TCTCTTTTTTCTATTAATAACTTTGTATGAGATTCCATCTTAATACTTTTCTGTTGTTTGGTCTT

-1106  GTAAGAGCTTATTTTTCTGAACCAGGAAGTGGTTCAGGGCGGTTTTTCTAACTTCACAGAGCTCC

-1041  CTCTTCTGTTAGCTTTTGTGAAATGGTCAAAAACATAGCAGCCTGCCTTCTGAGTTCTCCATCCC

-976  ACCCTGGTTGGGCCTTCTCTATCCTTGTCTGTGTTGTTTATATCCTGCTGAAGTGTGATTCCACT
```

FIG. 14F

```
-911  TGTGCAGTTTCTCCTCTGTGTAGGATCAAAAGGGCTGTGGCTGGTTGGTTTGAAAATTTCTTATAC

-845  CCTAGACTATTCCAGTGCCTTTCAGAAGTTTCCAAGGCCCTCTCACACTAATCTATTATCATATTG

-779  GGCAAAACTCCTTGCAGTTTCAGCTACTATTCCCTGATTGACTTTTCAGTAAATCTATCTCTCAGT

-713  CTTTCAGTATCCAAAGAAGATTGGTTCTAGGACCACCATCCCGCTGCCTCCACAGATACCAAAATC

-647  AGAGGATGCTCAATTCCCTCTTATAAAACGTTGCAGTATTTGCATATAATCTGCACATGTATTTCT

-581  GTATATTTTAAATCATCCCTAGATTACTTATAATACCTGATACAATATAAATGCTAAATAGCTGTA

-515  ACACTGTATCTTTAAAATTTACATTATTTTTTGTTGTTGTATTATTATTTTTATTGTATTTTTAAA

-449  AAATATTTTCCATCTACAGTCAGTAGAATCCACGGATACAGAACCTATGGATAGGAAGGACCAACT

-383  GTATCTTTTAGTGTTTTGAGGTTCTTG
```

FIG. 14G

-356 AATTCTCAGGTCGTTTGCTTTCCTTTGCTTTCTCCCAAGTCTTGTTTTACAATTTGCTTTAGTCA

-291 TTCACTGAAACTTTAAAAAACATTAGAAAACCTCACAGTTTGTAAATCTTTTTCCCTATTATATA

-226 TATCATAAGATAGGAGCTTAAATAAAGAGTTTTAGAAACTACTAAAATGTAAATGACATAGGAAA

-161 ACTGAAAGGGAGAAGTGAAAGTGGGAAATTCCTCTGAATAGAGAGAGGACCATCTCATATAAATA

CAP (-81)
-96 GGCCATACCCACGGAGAAAGGACATTCTAACTGCAACCTTTCGAAGCCTTTGCTCTGGCACAACA

AUG (1)
-31 GGTAGTAGGCGACACTGTTCGTGTTGTCAAC ATG ACC AAC AAG TGT CTC CTC CAA

25 ATT GCT CTC CTG TTG TGC TTC TCC ACT ACA GCT CTT TCC ATG AGC TAC

73 AAC TTG CTT GGA TTC CTA CAA AGA AGC AGC AAT TTT CAG TGT CAG AAG

121 CTC CTG TGG CAA TTG AAT GGG AGG CTT GAA TAC TGC CTC AAG GAC AGG

Pvull (199)
169 ATG AAC TTT GAC ATC CCT GAG GAG ATT AAG CAG CTG CAG CAG TTC CAG

217 AAG GAG GAC GCC GCA TTG ACC ATC TAT GAG ATG CTC CAG AAC ATC TTT

265 GCT ATT TTC AGA CAA GAT TCA TCT AGC ACT GGC TGG AAT GAG ACT ATT

313 GTT GAG AAC CTC CTG GCT AAT GTC TAT CAT CAG ATA AAC CAT CTG AAG

361 ACA GTC CTG GAA GAA AAA CTG GAG AAA GAA GAT TTC ACC AGG GGA AAA

409 CTC ATG AGC AGT CTG CAC CTG AAA AGA TAT TAT GGG AGG ATT CTG CAT

457 TAC CTG AAG GCC AAG GAG TAC AGT CAC TGT GCC TGG ACC ATA GTC AGA

505 GTG GAA ATC CTA AGG AAC TTT TAC TTC ATT AAC AGA CTT ACA GGT TAC

BglII (565)
553 CTC CGA AAC TGAAGATCTCCTAGCCTGTGCCTCTGGGACTGGACAATTGCTTCAAGCATTCT

615 TCAACCAGCAGATGCTGTTTAAGTGACTGATGGCTAATGTACTGCATATGAAAGGACACTAGAAG

FIG. 15A

680  ATTTTGAAATTTTTATTAAATTATGAGTTATTTTTATTTATTTAAATTTTATTTTGGAAAATAAA

745  TTATTTTTGGTGCAAAAGTCAACATGGCAGTTTTAATTTCGATTTGATTTATATAACCATCCATA

810  TTATAAAATTGCCAAGTACCTATTAGTTGTTCTTTTTAAAATATACCTGCAAAGTAGTATACTTT

875  CTGGCCCCTGCCTTTAAGGAATTTAAAATTCAAGAAAGCCATGATGGAATATATAAGGTAAGAGA

940  CAATAAGGGGACCTGAACCTTATGGGGAATAAATATGGCATGAACTGCTGTGGGATTAAAAGAG

1005 AAAAGGAAAGCTGGAGGGTCTGGAACTAAACCTGGGGTTCCCATTCCTCCTACTGTGTGTTCCAG

Ball (1099)
1070 ATTCTCTCATCATAAAGTTAGAATTGAGCTGGCCATCAGGAATAGCCAGAGGAATATGTCAGCTT

1135 TTGTGTTCTCCCTAACCTTCCCCAGTTATTTGGGGGATCACTTTGCTCCTCGAAAGATTTTTAAA

1200 TAATTATGTGCCCCCCACCATCCCTGCAA

FIG. 15B

PROTEIN PRODUCTION AND DELIVERY

RELATED APPLICATIONS

This application is a Continuation-In-Part of U.S. patent application Ser. No. 08/243,391, filed May 13, 1994, now U.S. Pat. No. 5,641,670, which is a Continuation-In-Part of U.S. patent application Ser. No. 07/985,586, filed Dec. 3, 1992, now abandoned and is also a Continuation-In-Part of U.S. patent application Ser. No. 07/911,533, filed Jul. 10, 1992, now abandoned, and is also a Continuation-In-Part of U.S. patent application Ser. No. 07/787,840, filed Nov. 5, 1991, now abandoned, and is also a Continuation-In-Part of U.S. patent application Ser. No. 07/789,188, filed Nov. 5, 1991, now abandoned all of which are incorporated herein by reference. This application also claims priority and is related to PCT/US93/11704, filed Dec. 2, 1993, and is also related to PCT/US92/09627, filed Nov. 5, 1992. The teachings of PCT/US93/11704 and PCT/US92/09627 are incorporated herein by reference.

BACKGROUND OF THE INVENTION

Current approaches to treating disease by administering therapeutic proteins include in vitro production of therapeutic proteins for conventional pharmaceutical delivery (e.g. intravenous, subcutaneous, or intramuscular injection, or by intranasal or intratracheal aerosol administration) and, more recently, gene therapy.

One protein which may be useful in the treatment of platelet disorders is thrombopoietin (TPO). Platelets are small (2–3 microns in diameter) anucleated cells which play an important role in primary hemostasis by adhering to and aggregating at sites of vascular damage. In addition, platelets release factors which are important components of the blood coagulation, inflammation, and wound healing pathways. Patients with very low levels of circulating platelets (thrombocytopenia) exhibit bleeding into superficial sites (e.g. skin, mucous membranes, genitourinary tract, and gastrointestinal tract) as a result of mild trauma, and are at risk for death from catastrophic hemorrhage occurring spontaneously or resulting from trauma. The physiologic role of platelets and the etiology of platelet disorders have been described (cf. *Hematology: Clinical and Laboratory Practice*, Eds. R. L. Bick et al., pp. 1337–1389, Mosby, St. Louis (1993); *Harrison's Principles of Internal Medicine*, Eds. J. D. Wilson et al., 11th Ed., pp. 1500–1505, McGraw Hill, N.Y., 1991).

Thrombocytopenia may be caused by decreased production of platelets by the bone marrow, increased sequestration of platelets in the spleen, or accelerated platelet destruction. Decreased production of platelets by the bone marrow may result from destruction of hematopoietic precursor cells by irradiation or treatment with cytotoxic agents during therapy for cancer. In addition, alcohol, estrogens, and thiazide diuretics can suppress platelet production (drug-induced thrombocytopenia). Furthermore, infiltration of the bone marrow by malignant cells and the disorders congenital amegakaryocytic hypoplasia and thrombocytopenia with absent radii (TAR syndrome) can result in decreased platelet production.

Increased splenic sequestration of platelets may occur as a result from splenomegaly associated with a variety of conditions, including liver disease, infiltration of the spleen with tumor cells as in myeloproliferative or lymphoproliferative disorders, and Gaucher's disease.

Accelerated platelet destruction and thrombocytopenia may be caused by vasculitis, hemolytic uremic syndrome, disseminated intravascular coagulation, and the presence of intravascular prosthetic devices such as cardiac valves. In addition, certain viral infections, drugs, and autoimmune disorders lead to immunologic thrombocytopenia in which platelets become coated with antibody, immune complexes, or complement and are rapidly cleared from the circulation. A number of drugs can elicit an immune response leading to immunologic thrombocytopenia, including sulfathiazole, novobiocin, para-aminosalicylate, quinidine, quinine, carbamazepine, digitoxin, arsenical drugs, and methyldopa.

Thrombocytopenia is currently treated most readily by transfusion with platelet concentrates, although corticosteroid therapy or plasmapheresis can be effective in immunologic thrombocytopenia. Treatment with platelet concentrates is severely limited by availability of suitable donors and the risk of transmission of blood-borne infectious diseases.

As an alternative to transfusion therapy, platelet deficiencies could be treated with hematopoietic growth factors which promote proliferation and maturation of megakaryocytes, the nucleated progenitor cells from which platelets are derived. Recently, cDNA clones were isolated which encode the human, mouse, and dog analogs of a protein purified from aplastic porcine plasma which displays megakaryocytopoietic activity (de Sauvage, F. J. et al. *Nature* 369:533–538 (1994); Lok, S. et al. *Nature* 369:565–568 (1994); Bartley, T. D. et al. *Cell* 77:1117–1124 (1994)). The encoded protein, termed thrombopoietin (TPO), stimulates proliferation and maturation of megakaryocytes and induces platelet production in vivo upon injection into experimental animals.

Methods for the production and delivery of other proteins with therapeutic properties are desirable. For example, it has been demonstrated that recombinant β-interferon is an effective medication for treatment of exacerbations in patients with relapsing-remitting multiple sclerosis (MS; see Kelley, C. L. and Smeltzer, S. C. *J. Neuroscience Nursing* 26:52–56 (1994)). Furthermore, it has been reported that β-interferon isolated from non-transfected cultured human fibroblasts may be an effective means for preventing the progression of acute non-A, non-B hepatitis to chronic disease (Omata, M. et al., *Lancet* 338:914–915 (1991)).

As another example, it has been demonstrated that recombinant human DNase I is an effective agent for reducing the viscosity of sputum from cystic fibrosis (CF) patients (Shak, S. et al., *Proc. Natl. Acad. Sci. USA* 87:9188–9192 (1990)) and for improving pulmonary function and decreasing exacerbations of respiratory disease in CF patients (Fuchs, H. J. et al., *New Engl. J. Med.* 331:637–642 (1994)). It has been further suggested that DNase I may be effective in improving respiratory function in patients with other respiratory diseases, such as chronic bronchitis and pneumonia (Shak, S. et al., op. cit.).

While TPO, β-interferon, and DNase I are useful, for example, in the treatment of thrombocytopenia, MS, and CF, respectively, production of therapeutic proteins using genetic engineering technology as taught in the prior art is limited to conventional recombinant DNA methods, in which the recombinant protein is purified from mammalian cells expressing an exogenous cloned gene or cDNA under the control of a suitable promoter. The exogenous DNA encoding the protein of interest is introduced into cells in the form of a viral vector, circular plasmid DNA, or linear DNA fragment. Chinese Hamster Ovary (CHO) cell lines and their derivatives (Gottesman, M. M. *Meth. Enzymol.* 151:3–8 (1987) or mouse cell lines, such as NSO (Galfre, G. and Milstein, C., *Meth. Enzymol.* 73(B): 3–46 (1981)) or P3X63Ag8.653 (Kearney, J. et al. *J. Immunol.* 123: 1548–1550 (1979)) are commonly used, and the production of human therapeutic proteins is thus accomplished by expression and purification of the protein from a cell of non-human origin.

In many cases, it is desirable to produce human therapeutic proteins in a human cell, for example, when it is desired that the glycosylation pattern of the protein be similar to patterns normally found on human cells. In addition, the expression of human proteins in human cells is important in the development of gene therapy methods, in which a patient's cells are engineered to produce a desired therapeutic protein to alleviate the symptoms or cure a disease.

Clearly, the development of novel methods for the production of these human proteins in human cells would be of benefit to patients, through the availability of a wider range of products with therapeutic effectiveness. One approach proposed by scientists in the field for accomplishing this goal is to use homologous recombination, or gene targeting, to introduce a cloned, exogenous regulatory element (i.e. a promoter and/or enhancer) into a cell's genome at a preselected site such that the regulatory element activates expression of a nearby gene, ultimately resulting in production of the protein encoded by that gene. This approach has been suggested in U.S. Pat. No. 5,272,071 and in foreign patent applications WO 91/06666, WO 91/06667 and WO 90/11354.

SUMMARY OF THE INVENTION

Described herein are new methods for producing TPO, DNase I, and β-interferon through the generation of novel transcription units within a cell's genome, methods which differ dramatically from those in the art and represent a major advance in the ability to manipulate expression in mammalian cells. The methods are based on the fact that an exogenous regulatory sequence, an exogenous exon, either coding or non-coding, and a splice-donor site can be introduced into a preselected site in the genome by homologous recombination. The resulting cells are referred to as targeted or homologously recombinant cells. The introduced DNA is positioned such that transcripts under the control of the exogenous regulatory region include both the exogenous exon and endogenous exons present in either the TPO, DNAse I, or β-interferon genes, resulting in transcripts in which the exogenous and endogenous exons are operatively linked. The novel transcription units produced by homologous recombination allow TPO, DNAse I, or β-interferon to be produced in human cells using the naturally-occurring endogenous exons encoding these proteins without introducing any portion of the coding sequences of the cognate genes. The present invention further relates to improved materials and methods for both the in vitro production of TPO, β-interferon, and DNase I and for the production and delivery of TPO, β-interferon, and DNase I by gene therapy.

The methods of the present invention teach the production of TPO, β-interferon, or DNase I by gene activation, in which the coding DNA sequence of the corresponding protein is not introduced into a cell by transfection of exogenous DNA encoding the protein. Instead, noncoding sequences upstream of one of these genes or coding or noncoding sequences within the genes are manipulated by gene targeting to create a novel transcription unit which expresses TPO, β-interferon, or DNase I. It is a purpose of this invention to define sequences upstream of the TPO, β-interferon, or DNase I genes, non-coding sequences (introns and 5' non-translated sequences) within the human TPO, β-interferon, or DNase I genes, and methods for utilizing these sequences for the production of TPO, β-interferon, or DNase I.

The methods described herein teach production of TPO, β-interferon, or DNase I proteins, by the generation of novel genes in which exogenous and endogenous exons are operatively linked. As a result of introduction of exogenous components into the chromosomal DNA of a cell, the expression of the protein encoded by the endogenous gene is activated. Other forms of altered gene expression may be envisioned, such as increasing expression of a gene which is expressed in the cell as obtained, changing the pattern of regulation or induction such that it is different than occurs in the cell as obtained, and reducing (including eliminating) expression of a gene which is expressed in the cell as obtained. For example, it may be desirable to perform in vitro protein production or gene therapy to produce a protein other than TPO, DNase I, or β-interferon using a cell type that naturally produces one of these proteins. In these settings, it would be desirable to eliminate expression of TPO, DNase I, or β-interferon.

The present invention further relates to DNA constructs useful in the method of activation of the TPO, β-interferon, or DNase I genes. The DNA constructs comprise: (a) targeting sequences; (b) a regulatory sequence; (c) an exon; and (d) an unpaired splice-donor site. The targeting sequence in the DNA construct is derived from chromosomal DNA lying within and/or upstream of the desired gene and directs the integration of elements (a)–(d) into the chromosomal DNA in a cell such that the elements (b)–(d) are operatively linked to sequences of the desired endogenous gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence in the DNA construct is derived from chromosomal DNA lying within and/or upstream of the desired gene and directs the integration of elements (a)–(f) such that the elements of (b)–(f) are operatively linked to the desired endogenous gene. The targeting sequence is homologous to the preselected site within or upstream of the TPO, β-interferon, or DNase I genes in the cellular chromosomal DNA with which homologous recombination is to occur. In the construct, the exon is generally 3' of the regulatory sequence and the splice-donor site is 3' of the exon. Constructs of this type are disclosed in pending U.S. patent applications U.S. Ser. No. 07/985,586 and U.S. Ser. No. 08/243,391, all of which are incorporated herein by reference.

The following serves to illustrate two embodiments of the present invention, in which the sequences upstream of the TPO gene are altered to allow expression of TPO in primary, secondary, or immortalized cells which do not express TPO in detectable quantities in their untransfected state as obtained. In embodiment 1 (FIG. 1), the targeting construct contains two targeting sequences. Both the first and second targeting sequences are homologous to sequences upstream of the TPO coding region, with the first targeting sequence 5' of the second targeting sequence. The targeting construct also contains a regulatory region, an exon (which in this case, comprises noncoding sequences and begins at a CAP site) and an unpaired splice-donor site. The homologous recombination event that generates the novel transcription unit producing TPO is shown in FIG. 1.

In embodiment 2 (FIG. 2), the targeting construct also contains two targeting sequences. The first targeting sequence is homologous to sequences upstream of the endogenous TPO coding region, and the second targeting sequence is homologous to the second intron of the TPO gene. The targeting construct also contains a regulatory region, an exon (in this case a coding exon derived from the human growth hormone (hGH) gene) and an unpaired splice-donor site. The homologous recombination event that generates the novel transcription unit producing TPO is shown in FIG. 2.

In these two embodiments, the products of the targeting events are novel transcription units which generate a mature mRNA in which an exogenous exon is positioned upstream of exon 2 (Embodiment 1) or exon 3 (Embodiment 2) of the endogenous TPO gene. The product of transcription, splicing, translation, and post-translational cleavage of the signal peptide is mature TPO. Embodiments 1 and 2 differ with respect to the relative positions of the regulatory sequences of the targeting construct that are inserted and the specific pattern of splicing that needs to occur to produce the final, processed transcript.

The invention further relates to a method of producing TPO, β-interferon, or DNase I in vitro or in vivo through introduction of a construct as described above into host cell chromosomal DNA by homologous recombination to produce a homologously recombinant cell. The homologously recombinant cell is then maintained under conditions which will permit transcription, translation and secretion of TPO, β-interferon, or DNase I.

The present invention also relates to cells, such as homologously recombinant primary or secondary cells (i.e., non-immortalized cells) and homologously recombinant immortalized cells, useful for producing TPO, β-interferon, or DNase I, methods of making such cells, methods of using the cells for in vitro protein production, and methods of gene therapy. Homologously recombinant cells of the present invention are of vertebrate origin, particularly of mammalian origin, and even more particularly of human origin. Homologously recombinant cells produced by the method of the present invention contain exogenous DNA which causes the homologously recombinant cells to express a desired gene at a higher level or with a pattern of regulation or induction that is different than occurs in the corresponding cell that has not undergone homologous recombination.

In one embodiment, the activated TPO, β-interferon, or DNase I gene can be further amplified by the inclusion of an amplifiable selectable marker gene which has the property that cells containing amplified copies of the selectable marker gene can be selected for by culturing the cells in the presence of the appropriate selectable agent. The activated gene is amplified in tandem with the amplifiable selectable marker gene. Cells containing many copies of the activated gene are useful for in vitro protein production and gene therapy.

Homologously recombinant cells of the present invention are useful in a number of applications in humans and animals. In one embodiment, the cells can be implanted into a human or an animal for protein delivery in the human or animal. For example, TPO, DNase I, or β-interferon can be delivered systemically or locally in humans for therapeutic benefit in the treatment of disease (TPO for thrombocytopenia, DNase I for CF, or β-interferon for the treatment of MS). In addition, homologously recombinant non-human cells producing TPO, DNase I, or β-interferon of non-human origin may be produced, and human or non-human cells expressing TPO, DNase I, or β-interferon may be enclosed within barrier devices and implanted into humans or animals for use in a therapy.

BRIEF DESCRIPTION OF THE DRAWINGS

FIGS. 4A–4D present the nucleotide sequence of 4,488 bp of genomic DNA (SEQ ID NO: 3) from the human TPO locus lying 5' to the known cDNA sequence (de Sauvage et al., op. cit.). Nucleotide numbers are noted at the beginning of each line. Numbering is based on the ATG initiation codon at position 1 (see FIGS. 5A–5B). Ambiguities in the nucleotide sequence are represented using the following code: R=A or G (purine); H=A, C, or T; V=A, C, or G; N=A, C, G, or T; K=G or T; S=G or C; W=A or T. The recognition sites for ApaI, BamHI, HindIII, NotI, SfiI and XbaI and their corresponding nucleotide positions are indicated above the sequence.

FIGS. 5A–5B present the nucleotide sequence of 2,455 bp of genomic DNA (SEQ ID NO: 4) from the human TPO locus extending downstream from the position of the 5' end of the known cDNA sequence (de Sauvage et al., op. cit.). Nucleotide numbers are noted at the beginning of each line. Numbering is based on the ATG initiation codon at position 1. Shown are exon 1, intron 1, exon 2, intron 2, exon 3, and a portion of intron 3. Exons 1, 2, and 3 are underlined, and the coding portions of exons 2 and 3 are noted as underlined triplets. The intron-exon boundaries are deduced from the published cDNA sequence (de Sauvage et al., op. cit.). The recognition sites for ApaI, EcoRI, and XbaI and their corresponding nucleotide positions are indicated above the sequence.

FIGS. 10A–10D present the nucleotide sequence encompassing 4,042 bp of DNA (SEQ ID NO: 17) from the human DNase I locus lying 5' to the known cDNA sequence (Shak, S. et al. op. cit.). Nucleotides numbers are noted at the beginning of each line. Numbering is based on the ATG initiation codon at position 1 (see FIG. 11). The recognition sites, and the corresponding nucleotide positions for ApaI, BamHI, HincII, EspI, and SphI are indicated above the sequence.

FIG. 11 presents the nucleotide sequence of 810 bp of DNA (SEQ ID NO: 18) from the human DNase I locus extending downstream from the position of the 5' end of the known cDNA sequence (Shak, S. et al. op. cit.). Shown are exon 1, intron 1, and a portion of exon 2. Exon 1 and 2 sequences are underlined and the coding sequences are noted as underlined triplets. The positions of the putative CAP site and the AUG initiation codon are indicated. The intron-exon boundaries are deduced from the published cDNA sequence (Shak S. et al., op. cit.).

FIGS. 14A–14G present the nucleotide sequence of 8,355 bp of DNA (SEQ ID NO: 23) from the human β-interferon locus lying 5' to the known sequence (GenBank HUMIFNB1F). Nucleotide numbers are noted at the beginning of each line. Numbering is based on the ATG initiation codon at position 1 (see FIG. 15). The recognition sites for BglII, EcoRI and PvuII and their corresponding nucleotide positions are indicated above the sequence.

FIGS. 15A–15B present the nucleotide sequence of 1,584 bp of DNA (SEQ ID NO: 24) from the human β-interferon locus extending downstream from the 5' end of the known sequence (GenBank HUMIFNB1F). Nucleotide numbers are noted at the beginning of each line. Numbering is based on the ATG initiation codon at position 1. The transcribed region is underlined and the coding sequences are noted as underlined triplets. The position of the CAP site and AUG initiation codon are indicated. The recognition sites for BalI, BglII and PvuII and their corresponding nucleotide positions are indicated above the sequence.

DETAILED DESCRIPTION OF THE INVENTION

Figure 1:
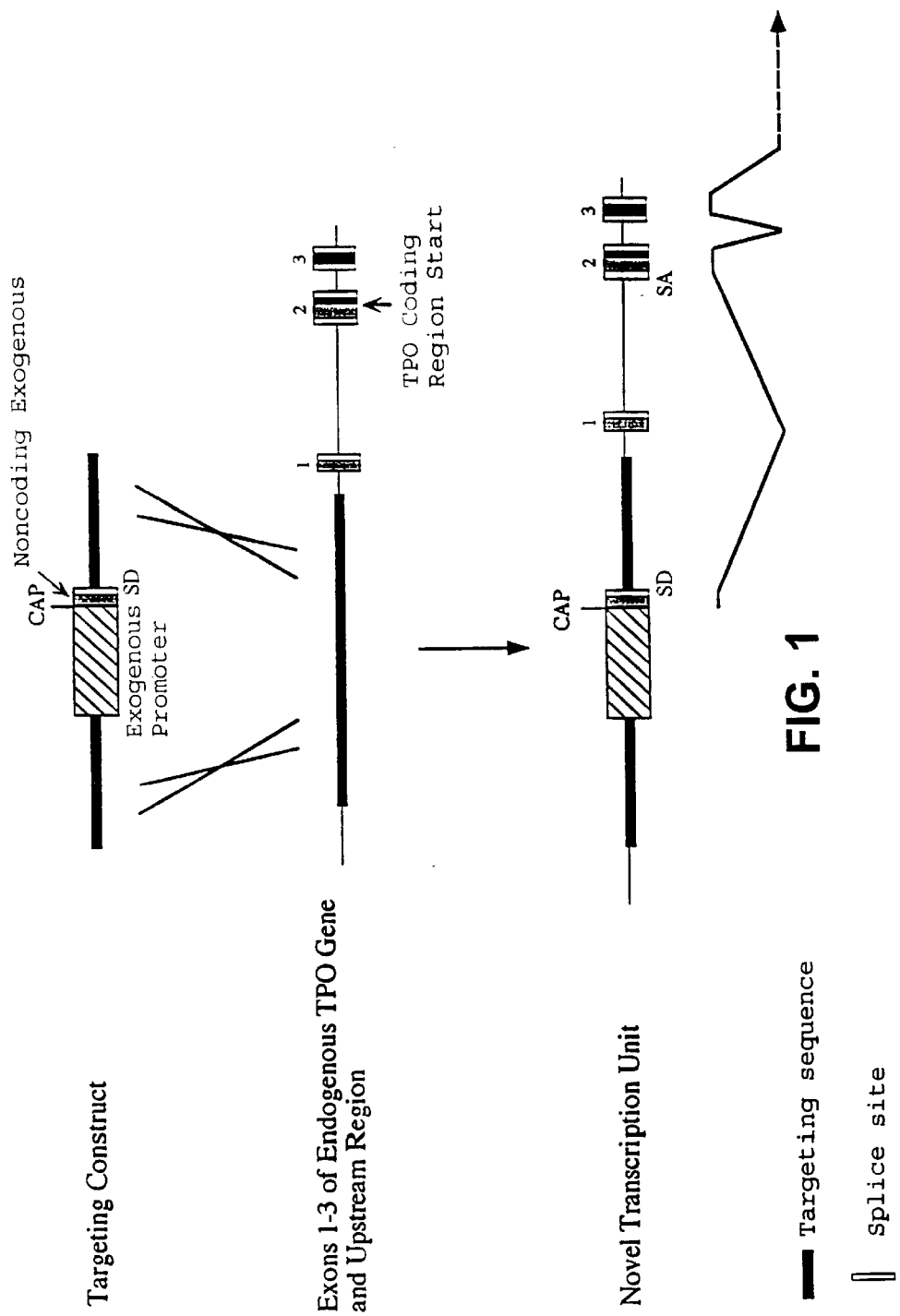
FIG. 1 is a schematic diagram of a strategy for transcriptionally activating the TPO gene by the creation of a novel transcription unit; thick lines: targeting sequences; thin lines: introns and 5' upstream region; cross-hatched box, regulatory sequence; stippled boxes: noncoding exon sequences; black boxes: coding exon sequences; open boxes: splice sites. The splice-donor site (SD) of the exogenous exon in the targeting construct and the splice-acceptor site (SA) flanking TPO exon 2 which is involved in splicing to the exogenous exon are indicated.
Figure 2:
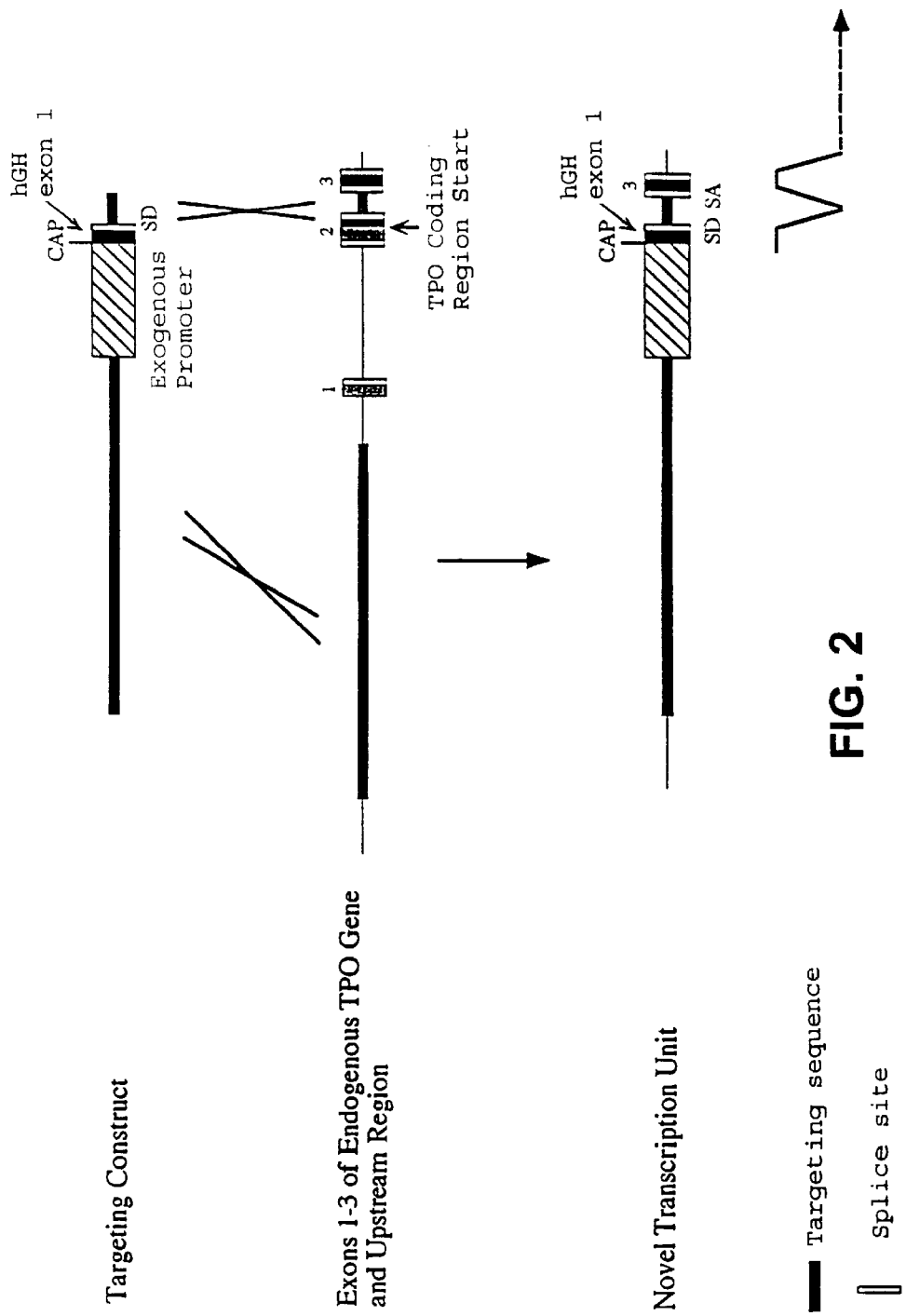
FIG. 2 is a schematic diagram of a strategy for transcriptionally activating the TPO gene by the creation of a novel transcription unit; thick lines: targeting sequences; thin lines: intron 1 and 5' upstream region; cross-hatched box: regulatory sequence; stippled boxes: noncoding exon sequences; black boxes: coding exon sequences; open boxes, splice sites. The splice-donor site (SD) of the exogenous exon in the targeting construct and the splice-acceptor site (SA) flanking TPO exon 3 which is involved in splicing to the exogenous exon are indicated.

The present invention as set forth above, relates to a method of expressing TPO, DNase I, or β-interferon in human cells by activation of the endogenous TPO, DNase I, or β-interferon genes. In the present invention, homologous recombination is used to insert a regulatory region, an exon, and a splice-donor site upstream of endogenous exons coding for TPO, DNase I, or β-interferon, generating novel transcription units which are active in the homologously recombinant cell produced. The present invention further relates to homologously recombinant cells produced by the present method and to uses of the homologously recombinant cells. In a related embodiment, an activated TPO, DNase I, or β-interferon gene is amplified subsequent to activation, thus allowing enhanced expression of the activated gene.

The invention is based upon the discovery that the regulation or activity of endogenous genes of interest in a cell can be altered by creating a novel gene, in which the transcription product of the gene combines exogenous and endogenous exons and is under the control of an exogenous promoter. The method is practiced by inserting into a cell's genome, at a preselected site, through homologous recombination, DNA constructs comprising: (a) one or more targeting sequences; (b) a regulatory sequence; (c) an exon and (d) an unpaired splice-donor site, wherein the targeting sequence or sequences are derived from chromosomal DNA within and/or upstream of a desired endogenous gene and directs the integration of elements (a)–(d) such that the elements (b)–(d) are operatively linked to the endogenous gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence or sequences are derived from chromosomal DNA within and/or upstream of a desired endogenous gene and directs the integration of elements (a)–(f) such that the elements of (b)–(f) are operatively linked to the first exon of the endogenous gene.

The present invention relates particularly to novel DNA sequences that can be used in the construction of targeting constructs. Non-coding genomic DNA sequences within and upstream of the transcribed regions of the TPO and DNase I genes, and upstream of the transcribed region of the β-interferon gene, were cloned and are described for the first time. These sequences or DNA fragments comprising these sequences may be used as targeting sequences in DNA constructs useful for gene activation by homologous recombination. Typically, a targeting sequence is at least about 20 base pairs in length. The size of the sequence is chosen to be a size which selectively promotes homologous recombination with desired genomic DNA sequences.

Analysis of the genomic DNA sequences and comparison to the known cDNA sequences revealed features essential for the construction of targeting constructs. For example, for the first time, it is shown that the first exon of the human TPO gene is entirely non-coding, and that translation initiates within the second exon of the endogenous gene. This information was important to the design of the gene activation constructs described herein, in which splicing of an exogenous exon to the endogenous second exon requires that the exogenous exon be non-coding, or in which splicing of an exogenous coding exon requires that targeting be performed such that the exogenous coding exon is inserted in a position so that it can be spliced to the endogenous third exon of the TPO gene. Furthermore, the cloning of approximately 6.3 kb of DNA sequence from upstream of the human TPO gene provided targeting sequences useful for the development of gene activation constructs. FIG. 4 shows approximately 4.5 kb of novel DNA sequence from the human TPO locus lying 5' of the known cDNA sequence (de Sauvage, F. J. et al., op. cit.). FIG. 5 shows approximately 2.5 kb of DNA sequence from the human TPO locus extending in the 3' direction from the 5' boundary of the known cDNA sequence. Intron sequences (positions −1815 to −145, positions 14 to 245, and positions 374 to 570) of FIG. 5 are novel. DNA constructs comprising the novel sequences of FIGS. 4 and 5, or fragments derived from these sequences, are useful for homologous recombination as taught herein.

Similarly, for the first time it is shown that the first exon of the human DNase I gene is entirely non-coding. This information was important to the design of the targeting constructs described herein. Example 5, for example, describes a targeting construct which includes two non-coding exons separated by an intron, and which is inserted upstream of DNase I exon 1. This configuration allows promoter position to be optimized by varying the length of either the exogenous intron or the intron present between the exogenous exon and the endogenous second exon of the DNase I gene, while ensuring that the primary transcript will be spliced appropriately and that translation initiates at the correct position for synthesis of functional DNase I. Furthermore, the cloning of approximately 4.5 kb of DNA sequence from upstream of the human DNase I gene provided targeting sequences useful for the development of gene activation constructs. FIG. 10 shows approximately 4 kb of novel DNA sequence from the human DNase I locus lying 5' of the known cDNA sequence (Shak, S. et al. op. cit.). FIG. 11 shows approximately 0.8 kb of DNA sequence from the human DNase I locus extending in the 3' direction from the 5' boundary of the known cDNA sequence. Intron sequences (positions −328 to −2) of FIG. 11 are novel. DNA constructs comprising the novel sequences of FIGS. 10 and 11, or fragments derived from these sequences, are useful for homologous recombination as described herein.

Finally, the analysis of the upstream region of the β-interferon gene (a gene which is known to lack introns) was cloned and sequenced and a detailed restriction map was produced. Previously, only 357 bp of DNA upstream of the translation initiation codon was characterized (see Genbank entry HUMIFNB1F). The cloning and sequence analysis provided approximately 9.6 kb of genomic DNA upstream of the gene for the design and construction of a targeting construct (Example 7). FIG. 14 shows approximately 8.4 kb of novel DNA sequence from the β-interferon locus lying 5' of the known sequences (Genbank entry HUMIFNB1F). DNA constructs comprising the novel sequences of FIG. 14, or fragments derived from these sequences, are useful for homologous recombination as taught herein.

The following defines the DNA constructs of the present invention, the elements comprising the DNA constructs of the present invention (Section A), methods in which the DNA constructs are used to produce homologously recombinant cells (Section B), the structure of the targeted gene and the resulting product (Section C), the homologously recombinant cells produced (Section D), uses of these cells (Sections E and F), and the advantages of the constructs and methods described herein (Section G).

A. The DNA Construct

The DNA constructs of the present invention include at least the following components: a targeting sequence; a regulatory sequence; an exon and a splice-donor site. In the construct, the exon is 3' of the regulatory sequence and the splice-donor site is 3' of the exon. In addition, there can be multiple exons and/or introns preceding (5' to) the exon flanked by the splice-donor site. Taken as a group, the exons, introns, and splice-sites are referred to as the "structural elements" of the construct, so-called because they are important in defining the structure of the novel gene produced by homologous recombination between genomic DNA and DNA of the targeting construct. As described herein, there frequently are additional construct components, such as a selectable and/or amplifiable markers.

The DNA in the construct is referred to as exogenous DNA, defined herein as DNA which is introduced into a cell by the methods described herein, such as with the DNA constructs of the present invention. Exogenous DNA can contain sequences identical to or different from the endogenous DNA. The term endogenous DNA is defined herein as DNA present in the cell as obtained.

The DNA of the construct can be obtained from sources in which it occurs in nature or can be produced, using genetic engineering techniques or synthetic processes.

1. The Targeting Sequence

The targeting sequence or sequences are DNA sequences which permit homologous recombination into the genome of the selected cell containing the gene of interest. Targeting sequences are, generally, DNA sequences which are homologous to (i.e., identical or sufficiently similar to) DNA sequences present in the genome of the cells as obtained (e.g., coding or noncoding DNA, located upstream of the transcriptional start site, within the transcribed region encompassing the gene, or downstream of the transcriptional stop site of the gene, or sequences present in the genome through a previous modification), such that the targeting sequence and cellular DNA can undergo homologous recombination. In general, two sequences are described as homologous if a DNA strand of one sequence is capable of hybridizing to a DNA strand of the other sequence under conditions standardly used for the detection of sequence similarity (see, for example, Ausubel et al., *Current Protocols in Molecular Biology*, Wiley, New York, N.Y. (1987)). The targeting sequence or sequences used are selected with reference to the site into which the DNA in the DNA construct is to be inserted and may be derived from either genomic or cDNA sequences. Typically, a targeting sequence is at least about 20 base pairs in length. The size of the sequence is chosen to be a size which selectively promotes homologous recombination with desired genomic DNA sequences.

One or more targeting sequences can be employed. For example, a circular plasmid or DNA fragment preferably employs a single targeting sequence. A linear plasmid or DNA fragment preferably employs two targeting sequences with exogenous DNA to be inserted into genome positioned between the two targeting sequences. The targeting sequence or sequences can be within an endogenous gene (e.g., within the sequences of an exon and/or intron), within the endogenous promoter sequences, or upstream of the endogenous promoter sequences. The targeting sequence or sequences can include those regions of a gene presently known or sequenced and/or regions further upstream which are structurally uncharacterized but can be mapped using restriction enzymes and cloning approaches available to one skilled in the art.

2. The Regulatory Sequence

The regulatory sequence of the DNA construct can be comprised of one or more of a variety of elements, including: promoters (such as a constitutive or inducible promoters), enhancers, scaffold-attachment regions or matrix attachment regions, (McKnight, R. A. et al., *Proc. Natl. Acad. Sci. USA* 89:6943–6947 (1992); Phi-Van, L. and Strätling, W. H. *EMBO J.* 7:655–664 (1988)) negative regulatory elements, locus control region, (Pondel, M. D. et al., *Nucl. Acids Res.* 20:237–243 (1992); Li, Q. and Stamatoyannopoulos, G. *Blood* 84:1399–1401 (1994)) transcription factor binding sites, or combinations of said sequences.

3. Structural Elements of the DNA Construct a. Exons and Introns

An exon is defined herein as a DNA sequence which is copied into RNA and is present in a mature mRNA molecule. An intron is defined as a sequence of one or more nucleotides lying between two exons and which is removed, by splicing, from a precursor RNA molecule in the formation of an mRNA molecule.

The DNA constructs of the present invention contain one or more exons. The exons can, optionally, contain DNA which encodes one or more amino acids and/or partially encodes an amino acid (i.e., one or two bases of a codon). Where the exogenous exon or exons encode one or more amino acids and/or a portion of an amino acid, the DNA construct is designed such that, upon transcription and splicing, the reading frame is in-frame with the second or subsequent exon of the endogenous gene's coding region. As used herein, in-frame means that the encoding sequences of, for example, a first exon and a second exon when fused, join together nucleotides in a manner that does not change the appropriate reading frame of the portion of the mRNA derived from the second exon.

In the case of activating the TPO and DNase I genes, the exogenous exon can, preferably, be derived from any gene in which the exon includes a CAP site and non-coding sequences. Examples would include the first exon of the CMV immediate-early gene and follicle stimulating hormone (FSH) gene. In the case of β-interferon, whose gene contains no natural introns, there are preferably two exogenous non-coding exons, separated by an intron, in the targeting construct.

b. Splice-Sites

Introns contained within the mRNA of eukaryotic cells are removed through the recognition of signals termed splice-donor and splice-acceptor sites. A splice-donor site is a sequence which directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. Splice-donor sites have a characteristic consensus sequence represented as: (A/C)AGGURAGU (where R denotes a purine nucleotide) with the GU in the fourth and fifth positions being required (Jackson, I. J., *Nucleic Acids Research* 19: 3715–3798 (1991)). The first three bases of the splice-donor consensus site are the last three bases of the exon. Splice-donor sites are functionally defined by their ability to effect the appropriate reaction within the mRNA splicing pathway.

An unpaired splice-donor site is defined herein as a splice-donor site which is present in a targeting construct and is not accompanied in the targeting construct by a splice-acceptor site positioned 3' to the unpaired splice-donor site. Upon homologous recombination between the targeting sequences and genomic DNA, the unpaired splice-donor site results in splicing to an endogenous splice-acceptor site.

A splice-acceptor site is a sequence which, like a splice-donor site, directs the splicing of one exon to another exon. Acting in conjunction with a splice-donor site, the splicing apparatus uses a splice-acceptor site to effect the removal of an intron. Splice-acceptor sites have a characteristic sequence represented as: YYYYYYYYYYNYAG, where Y denotes any pyrimidine and N denotes any nucleotide (Jackson, I. J., *Nucleic Acids Research* 19:3715–3798 (1991)).

c. Marker Genes for Selection and Amplification

The identification of the targeting event can be facilitated by the use of one or more selectable marker genes typically contained within the targeting DNA construct. The use of both positively and negatively selectable markers for identifying targeted events is described in related pending applications U.S. Ser. Nos. 08/243,391, 07/985,586, 07/789,188, PCT/US93/11704, and PCT/US92/09627.

Homologously recombinant cells containing multiple copies of the novel transcription units produced by the present invention may be isolated by including within the targeting DNA construct an amplifiable marker gene which has the property that cells containing multiple copies of the selectable marker gene can be selected for by culturing the cells in the presence of an appropriate selectable agent. The novel transcription unit will be amplified in tandem with the amplified selectable marker gene, allowing the production of very high levels of the desired protein. Amplifiable marker genes and their use are described in applications U.S. Ser. Nos. 08/243,391, 07/985,586, and PCT/US93/11704.

In one embodiment the positively selectable marker neo is used (derived from the bacterial neomycin phosphotransferase gene) is used to select for cells which have stably incorporated the DNA of the targeting construct, and the mouse dhfr (dihydrofolate reductase) gene is used to subsequently amplify the novel transcription unit present in homologously recombinant cells.

d. Additional Elements of the Targeting Construct

As taught herein, gene targeting can be used to insert a regulatory sequence within an endogenous gene (e.g., within the sequences of an exon and/or intron), within the endogenous promoter sequences, or upstream of the endogenous promoter sequences, with said genes corresponding to the endogenous cellular TPO, β-interferon, or DNase I gene. Alternatively or additionally, the targeting constructs may be designed to include sequences which affect the structure or stability of the TPO, β-interferon, or DNase I protein or corresponding RNA molecule. For example, RNA stability elements, splice sites, and/or leader sequences of RNA molecules can be modified to improve or alter the function, stability, and/or translatability of an RNA molecule. Protein sequences may also be altered, such as signal sequences, active sites, and/or structural sequences for enhancing or modifying glycosylation, transport, secretion, or functional properties of a protein. According to this method, introduction of the exogenous DNA results in the alteration of the structural or functional properties of the expressed proteins or RNA molecules.

In one embodiment the method can be used to create novel transcription units encoding fusion proteins in which structural, enzymatic, or ligand or receptor binding protein domains of another protein are fused to TPO, DNase I, or β-interferon. In these cases the exogenous coding DNA contains an ATG translation initiation codon in-frame with the coding sequences of the endogenous TPO, DNase I, or β-interferon gene. For example, the exogenous DNA can encode a sequence which can anchor TPO or DNase I to a membrane, a portion of a signal peptide designed to improve cellular secretion, leader sequences, enzymatic regions, transmembrane domain regions, co-factor binding regions, or other functional regions.

The DNA construct can also include a bacterial origin of replication and bacterial antibiotic resistance markers or other selectable markers, which allow for large-scale plasmid propagation in bacteria or any other suitable cloning/host system.

B. Transfection and Homologous Recombination

According to the present method, the construct is introduced into the cell, such as a primary, secondary, or immortalized cell, as a single DNA construct, or as separate DNA sequences which become incorporated into the chromosomal or nuclear DNA of a transfected cell.

The targeting DNA construct can be introduced into cells on a single DNA construct or on separate constructs. The total length of the DNA construct will vary according to the number of components and the length of each and the construct will generally be at least about 200 nucleotides. Further, the DNA can be introduced as linear, double-stranded (with or without single-stranded regions at one or both ends), single-stranded, or circular DNA.

Any of the construct types of the disclosed invention is then introduced into the cell to obtain a transfected cell. The transfected cell is maintained under conditions which permit homologous recombination, as is known in the art (reviewed in Capecchi, M. R., *Science* 244:1288–1292 (1989)). When the homologously recombinant cell is maintained under conditions sufficient for transcription of the DNA, the regulatory region introduced by the targeting construct, as in the case of a promoter, will activate expression of the novel transcription unit produced by homologous recombination.

The DNA constructs may be introduced into cells by a variety of physical or chemical methods, including electroporation, microinjection, microprojectile bombardment, calcium phosphate precipitation, and liposome-, polybrene-, or DEAE dextran-mediated transfection.

C. The Targeted Gene and Resulting Product

The targeting DNA construct, when introduced by homologous recombination or targeting into cells containing the TPO, β-interferon, or DNase I gene, produces a novel transcription unit which results in the expression of TPO, β-interferon, or DNase I.

At the targeted site in the genome, the exogenous regulatory sequence is operatively linked to a CAP site, which initiates transcription. Operatively linked is defined as a configuration in which the exogenous regulatory sequence, exon, splice-donor site and, optionally, an intron sequence and splice-acceptor site, are appropriately targeted at a position relative to the endogenous gene such that the regulatory element directs the production of a primary RNA transcript which initiates at a CAP site and includes sequences corresponding to the exogenous exon or exons and endogenous exons the TPO, DNase I, or β-interferon gene. In an operatively linked configuration the splice-donor site of the targeting construct directs a splicing event between an exogenous exon and the splice-acceptor site of an endogenous exon, such that a desired protein can be produced from the fully spliced mature transcript. In one embodiment, the splice-acceptor site is endogenous, such that the splicing event is directed to an endogenous exon of the TPO or DNase I gene. In another embodiment an intron and a splice-acceptor site are included in the targeting construct used to activate the β-interferon gene, and a splicing event removes the intron introduced by the targeting construct.

D. The Homologously Recombinant Cells

The targeting event results in the insertion of the regulatory and structural sequences of the targeting construct into a cell's genome, creating a novel transcriptional unit under the control of the exogenous regulatory sequences.

Homologous recombination between the genomic DNA and the introduced DNA results in a homologously recombinant cell, which may be a primary, secondary, or immortalized human or other mammalian cell in which sequences which alter the expression of an endogenous gene are operatively linked to the endogenous TPO, DNase I, or β-interferon gene. Particularly, the invention includes a homologously recombinant cell comprising exogenous regulatory sequences and an exon, flanked by a splice-donor site, which are introduced at a predetermined site by a targeting DNA construct, and are operatively linked to the coding region of the endogenous gene. Optionally, there may be multiple exogenous exons (coding or non-coding) and introns operatively linked to any exon of the endogenous gene. The resulting homologously recombinant cells are cultured under conditions which select for amplification, if appropriate, of the DNA encoding the amplifiable marker and the novel transcriptional unit. With or without amplification, cells produced by this method can be cultured under conditions, as are known in the art, suitable for the expression of TPO, β-interferon, or DNase I.

The targeting constructs and methods of the present invention may be used with, for example, primary or secondary cell strains (which exhibit a finite number of mean population doublings in culture and are not immortalized) and immortalized cell lines (which exhibit an apparently unlimited lifespan in culture). Primary and secondary cells include, for example, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Where the homologously recombinant cells are to be used in gene therapy, primary cells are preferably obtained from the individual to whom the resulting homologously recombinant cells are administered. However, primary cells can be obtained from a donor (other than the recipient) of the same species. Examples of immortalized human cell lines which may be used with the DNA constructs and methods of the present invention include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (Van der Blick, A. M. et al., Cancer Res, 48:5927–5932 (1988), Raji cells (ATCC CCL 86), WiDr colon adenocarcinoma cells (ATCC CCL 218), SW620 colon adenocarcinoma cells (ATCC CCL 227), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) may be used. Further discussion of the types of cells that may be used in practicing the methods of the present invention is presented in applications U.S. Ser. Nos. 08/243,391, 07/985,586, 07/789,188, 07/911,533, 07/787,840, PCT/US93/11704, and PCT/US92/09627.

E. In Vivo Protein Production

Homologously recombinant cells of the present invention in which the expression properties of the endogenous TPO, β-interferon, or DNase I gene are altered are useful in gene therapy, as populations of homologously recombinant cell lines, as populations of homologously recombinant primary or secondary cells, homologously recombinant clonal cell strains or lines, homologously recombinant heterogenous cell strains or lines, and as cell mixtures in which at least one representative cell of one of the preceding categories of homologously recombinant cells is present. Homologously recombinant primary cells, clonal cell strains or heterogenous cell strains are administered to an individual in whom the abnormal or undesirable condition is to be treated or prevented, in sufficient quantity and by an appropriate route, to express or make available the desired product at physiologically relevant levels. A physiologically relevant level is one which either approximates the level at which the product is normally produced in the body or results in improvement of the abnormal or undesirable condition. Methods for gene therapy in which homologously recombinant cells are introduced into an individual for the purpose of in vivo protein production are described in pending applications U.S. Ser. Nos. 08/243,391, 07/985,586, 07/789,188, 07/911,533, U.S. Ser. No., PCT/US93/11704, and PCT/US92/09627.

In one embodiment, the invention relates to a method of providing TPO to a mammal introducing homologously recombinant cells into the mammal in sufficient number to produce an effective amount of TPO in the mammal.

In another embodiment homologously recombinant cells expressing DNase I can be administered to the trachea and lungs of a cystic fibrosis patient, for the purpose of in vivo secretion of DNase I for the relief of respiratory distress.

In a third embodiment, homologously recombinant cells expressing β-interferon may be implanted into a patient suffering from multiple sclerosis, for the purpose of in vivo secretion of β-interferon to diminish exacerbations associated with the disease.

F. In Vitro Protein Production

Homologously recombinant cells produced according to this invention can also be used for in vitro production of TPO, β-interferon, or DNase I. The cells are maintained under conditions, as are known in the art, which result in expression of the protein. Proteins expressed using the methods described may be purified from cell lysates or cell supernatants. Proteins made according to this method can be prepared as a pharmaceutically-useful formulation and delivered to a human or non-human animal by conventional pharmaceutical routes as is known in the art (e.g., oral, intravenous, intramuscular, intranasal, intratracheal or subcutaneous). As described herein, the homologously recombinant cells can be immortalized, primary, or secondary human cells. The use of cells from other species may be desirable in cases where the non-human cells are advantageous for protein production purposes where the non-human TPO, DNase I, or β-interferon produced is useful therapeutically.

G. Advantages

The methodologies, DNA constructs, cells, and resulting proteins of the invention herein possess versatility and many other advantages over processes currently employed within the art in gene targeting. The ability to activate expression of an endogenous TPO, β-interferon, or DNase I gene by positioning an exogenous regulatory sequence and other structural sequences at various positions ranging from directly fused to portions of the normal gene's coding region to 30 kilobase pairs or further upstream of the transcribed region of an endogenous gene, or within an intron of an endogenous gene, is advantageous for gene expression in cells. For example, it can be employed to position the regulatory element upstream or downstream of regions that normally silence or negatively regulate a gene. The positioning of a regulatory element upstream or downstream of such a region can override such dominant negative effects that normally inhibit transcription. In addition, regions of DNA that normally inhibit transcription or have an otherwise detrimental effect on the expression of a gene may be deleted using the targeting constructs, described herein. The present invention also allows proteins to be expressed in the context of their normal intron sequences, which have been shown to be important factors in the expression of genes in mammalian cells (cf. Korb. M. et al. *Nucl. Acids Res.* 21: 5901–5908 (1993)).

Additionally, since promoter function is known to depend strongly on the local environment, a wide range of positions may be explored in order to find those local environments optimal for function. However, since, ATG start codons are found frequently within mammalian DNA (approximately one occurrence per 48 base pairs as calculated from nearest-neighbor dinucleotide frequencies in human DNA), transcription cannot simply initiate at any position upstream of a gene and produce a transcript containing a long leader sequence preceding the correct ATG start codon, since the frequent occurrence of ATG codons in such a leader sequence will prevent translation of the correct gene product and render the message useless. Thus, the incorporation of an exogenous exon, a splice-donor site, and, optionally, an intron and a splice-acceptor site into targeting constructs comprising a regulatory region allows gene expression to be optimized by identifying the optimal site for regulatory region function, without the limitation imposed by needing to avoid inappropriate ATG start codons in the mRNA produced. This provides significantly increased flexibility in the placement of the construct and makes it possible to activate a wider range of genes than is possible using other technologies. For example, U.S. Pat. No. 5,272,071 and foreign patent applications WO 91/06666, WO 91/06667 and WO 90/11354 describe homologous recombination methods for inserting a regulatory sequence upstream of the coding region of an endogenous gene. In these methods, only a very small number of positions for promoter insertion are acceptable for expression, limited by the frequent occurrence of ATG start codons as described above.

The present invention provides further advantages over the methods available in the art. For example, the use of homologous recombination results in the production of cells in which the novel transcription unit is present in the same location in all cells in which homologous recombination has occurred. Thus, the novel transcription unit will function similarly in all homologously recombinant cells derived independently. This allows for the production of cells with highly predictable properties. In the case of in vitro protein production, it is desirable to develop cells in which the behavior (e.g. the expression and amplification properties) of the desired gene can be controlled and there is little variation when comparing individual cells which are being processed for large-scale production purposes. In the case of in vivo protein production or gene therapy, it is desirable to be able to develop cells in which the properties are predictable and uniform among individual patients. This allows for a high degree of precision in achieving appropriate levels of the desired protein in vivo, leading to controlled and reproducible methods for treating disease.

The DNA constructs described above are useful for operatively linking exogenous regulatory and structural elements to endogenous coding sequences in a way that precisely creates a novel transcriptional unit, provides flexibility in the relative positioning of exogenous regulatory elements and endogenous genes and, ultimately, enables a highly controlled system for and regulating expression of genes of therapeutic interest.

The subject invention will now be illustrated by the following examples, which are not intended to be limiting in any way.

EXAMPLES

Example 1

Cloning of the TPO Gene and Identification of 5' Flanking Sequences

The human thrombopoietin gene was isolated from a human genomic DNA library. The library was prepared from male leukocyte DNA partially-digested with MboI and cloned into the bacteriophage vector lambda EMBL3 (Clontech, Palo Alto, Calif.; Cat. #HL1006d). For screening, a probe was isolated by PCR amplification of human genomic DNA using oligonucleotides 1.1 and 1.2.

Oligo 1.1 (TPO sense) (SEQ ID NO: 1)
5' AATTGCTCCT CGTGGTCATG CTTCT
Oligo 1.2 (TPO anti-sense) (SEQ ID NO: 2)
5' CTGTGAAGGA CATGGGAGTC A These primers were designed using the known TPO mRNA sequence (de Sauvage, F. J. et al. *Nature* 369:533–538 (1994)). The amplified probe (probe A; 120 bp) was labeled with $^{32}$P dCTP by the polymerase chain reaction and used to screen the genomic DNA library. Filters were hybridized for 6 hours at 68° C. in 125 mM Na$_2$HPO$_4$ (pH 7.2), 250 mM NaCl, 10% PEG 8000, 7% SDS, 1 mM EDTA. Filters were washed twice in 500 ml of 20 mM Na$_2$HPO$_4$, (pH 7.2), 1 mM EDTA, 5% SDS, followed by 4 washes in 500 ml of 20 mM Na$_2$HPO$_4$, (pH 7.2), 1 mM EDTA, 1% SDS. The wash buffers were pre-heated to 56° C. and washing was done on a rotary shaker at room temperature for approximately 5 minutes per wash. The hybridizing signals were identified by autoradiography at −80° C. with an intensifying screen. In one experiment, approximately 1.4×10$^6$ phage were screened and 7 positive signals were obtained. Phage plaques corresponding to positive signals were plaque purified. Following 2 rounds of plaque purification by low density screening using probe A, 4 of the phage, designated 5B, 25A, 25B and 28B, were retained for further analysis. Plaque purified phage were amplified and isolated by cesium chloride gradient ultracentrifugation (Yamamoto K. R. et al., *Virology* 40:734 (1970)) and DNA was isolated. Library screening, plaque purification of recombinant bacteriophage, and isolation bacteriophage DNA was performed using standard methods (Ausubel et al., *Current Protocols in Molecular Biology*, Wiley, New York, N.Y. (1987)).

An approximately 6.9 kb XbaI fragment comprising exon 1, intron 1, exon 2, intron 2, exon 3, and a portion of intron 3, as well as approximately 4.3 kb of nontranscribed DNA lying upstream of TPO exon 1 was identified by restriction enzyme and Southern hybridization analysis using probe A. This fragment was isolated from one genomic clone (28B) and subcloned into plasmid pBSIISK$^+$ (Stratagene Inc., La Jolla, Calif.) for further analysis. The resultant clones, pBS(X)/5'Thromb.8 and pBS(X)/5'Thromb.2, harbor the 6.9 kb XbaI fragment in opposite orientations with respect to the plasmid backbone. Restriction enzyme mapping yielded the restriction enzyme map shown in FIG. 3. The nucleotide sequence of the portion of this fragment lying upstream of the 5' end of the known cDNA sequence is shown in FIG. 4 (SEQ ID NO: 3). The nucleotide sequence of the portion of the 6.9 kb XbaI fragment lying downstream of the 5' end of the known cDNA sequence is shown in FIG. 5 (SEQ ID NO: 4). Comparison of the cloned genomic sequence presented here with the published cDNA sequence (de Sauvage, F. J. et al. *Nature* 369:533–538 (1994)) reveals that the 5' end of the TPO gene consists of a non-coding exon (exon 1) of at least 107 bp, a second exon (exon 2) which is 158 bp, and a third exon (exon 3) which is 128 bp in length. The 13 base pairs at the 3' end of exon 2 code for the first four and a portion of the fifth amino acid of the TPO signal peptide. Exon 3 codes for the remainder of the 21 amino acid signal peptide and a portion of the mature TPO polypeptide. Exons 1 and 2 are separated by intron 1 (1671 bp), and exons 2 and 3 are separated by intron 2 (231 bp). There are two differences between the sequence reported in FIG. 5 and the sequence published by de Sauvage et al.: nucleotides at positions −134 and −124 are reported as C residues by de Sauvage et al. and are shown as T residues in FIG. 5. These residues are outside of the coding sequence for TPO and may be explained by sequence polymorphism or by errors in compilation of the published sequence. In any event, this minor difference does not impact the ability of the person of skill to practice the invention as described herein.

Example 2

Figure 6:
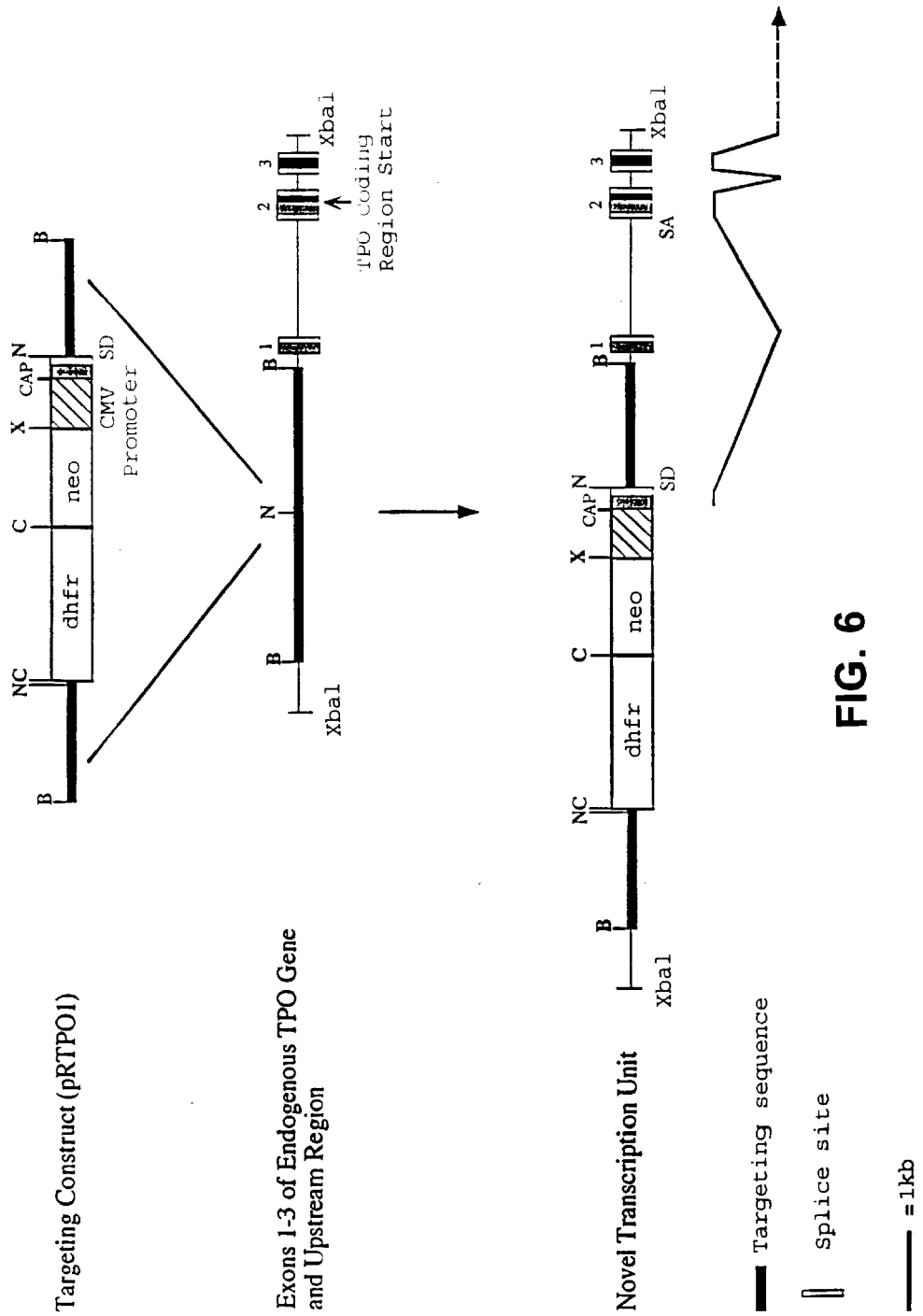
FIG. 6 is a schematic diagram of the strategy for activating the human TPO gene using targeting construct pTPO1 as described in Example 2. The positions of the dhfr and neo markers, the exogenous CMV promoter and TPO exons 1–3 are indicated. Thick lines: targeting sequences; thin lines: introns and 5' upstream region; cross-hatched box: CMV promoter; stippled boxes: noncoding exon sequences; black boxes: coding exon sequences, open boxes, splice sites. The splice-donor site (SD) of the exogenous exon in the targeting construct and the splice-acceptor site (SA) flanking TPO exon 3 which is involved in splicing to the exogenous exon are indicated. Recognition sites for BamHI (B), NotI (N), ClaI (C), XhoI (X), and XbaI which are relevant to the construction of the targeting construct are marked.
Figure 7:
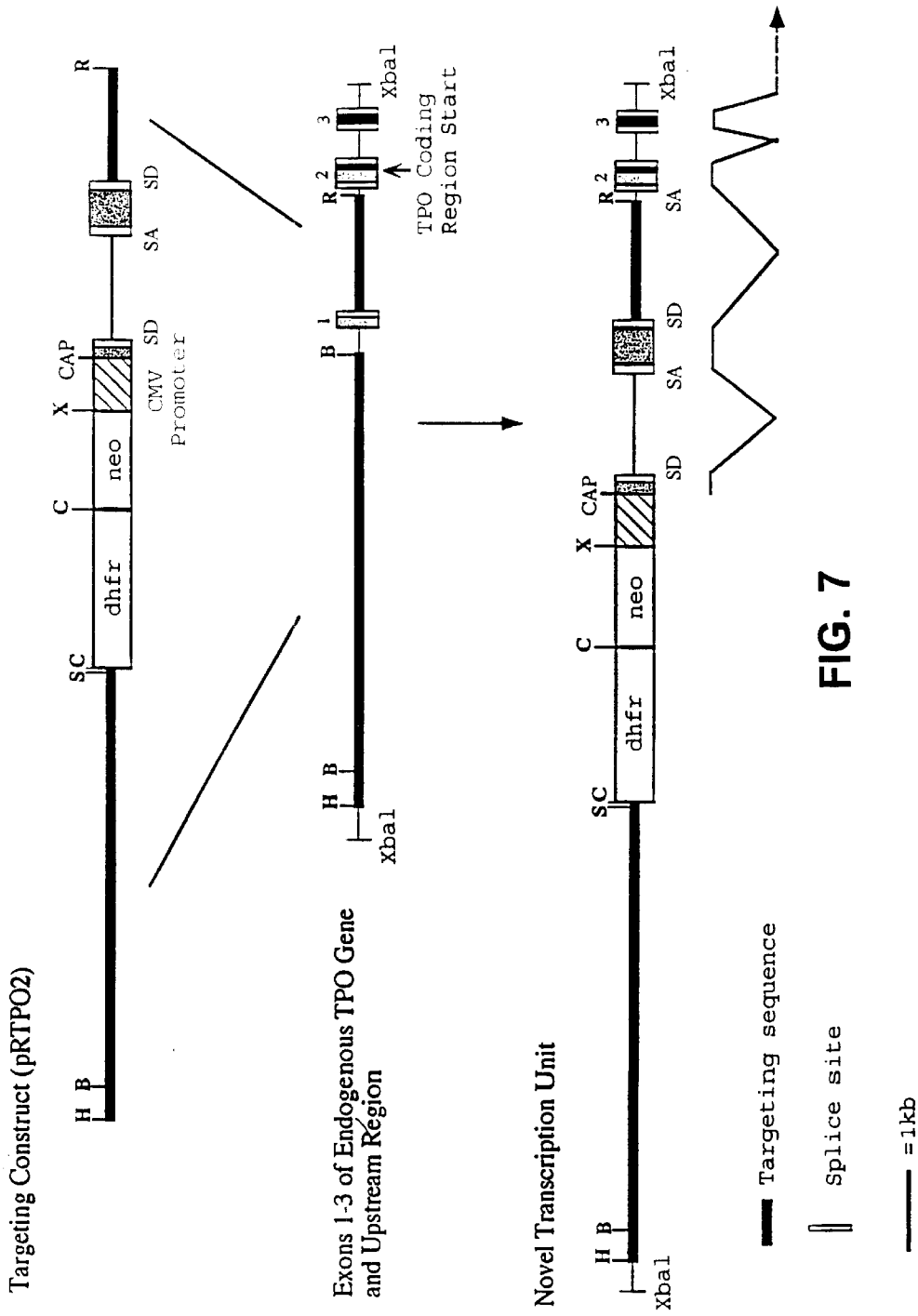
FIG. 7 is a schematic diagram of the strategy for activating the human TPO gene using targeting construct pTPO2 as described in Example 2. The positions of the dhfr and neo markers, the exogenous CMV promoter and TPO exons 1–3 are indicated. Thick lines: targeting sequences; thin lines: introns and 5' upstream region; cross-hatched box: CMV promoter; heavily stippled boxes: noncoding exons from the CMV IE gene; lightly stippled boxes: noncoding exon sequences of TPO exons 1 and 2; black boxes: coding exon sequences of TPO exons 2 and 3; open boxes: splice sites. The splice-donor (SD) and splice-acceptor (SA) sites flanking the noncoding exons in the targeting construct and the splice-acceptor site (SA) flanking TPO exon 2 which is involved in splicing to the unpaired splice-donor site of the 3' exogenous exon are indicated. Recognition sites for BamHI (B), HindIII (H), NotI (N), ClaI (C), SalI (S), EcoRI (R), and XbaI which are relevant to the construction of the targeting construct are marked.
Figure 8:
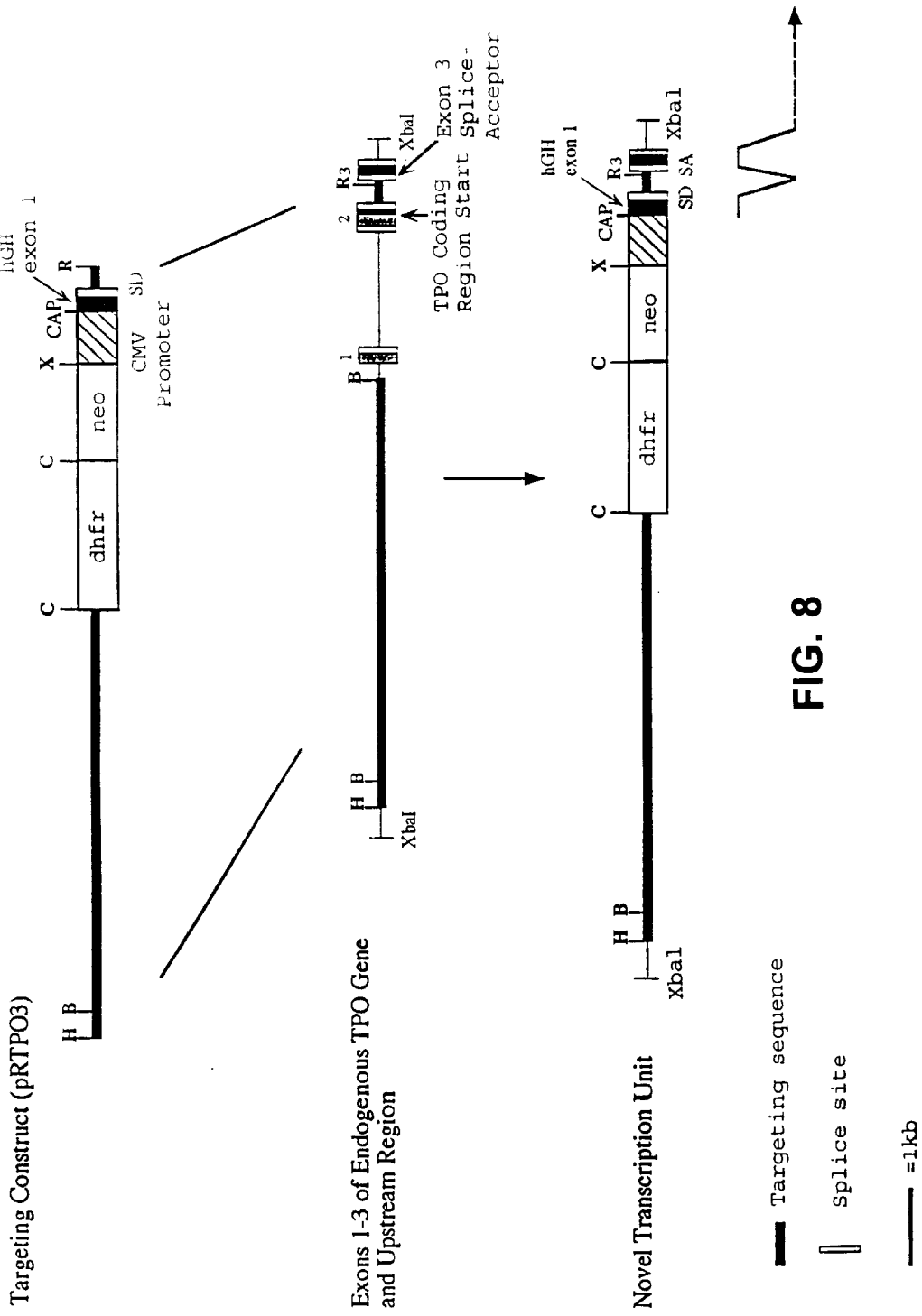
FIG. 8 is a schematic diagram of the strategy for activating the human TPO gene using targeting construct pTPO3 as described in Example 2. The positions of the dhfr and neo markers, the exogenous CMV promoter and TPO exons 1–3 are indicated. Thick lines: targeting sequences; thin lines: introns and 5' upstream region; cross-hatched box: CMV promoter; stippled boxes: noncoding exon sequences of TPO exons 1 and 2; black boxes: coding exon sequences (the coding exon corresponding to hGH exon 1 in the targeting construct and in the novel transcription unit is marked); open boxes: splice sites. The splice-donor site (SD) of the exogenous exon in the targeting construct and the splice-acceptor site (SA) flanking TPO exon 3 which is involved in splicing to the exogenous exon are indicated. Recognition sites for BamHI (B), HindIII (H), ClaI (C), XhoI (X), EcoRI (R), and XbaI which are relevant to the construction of the targeting construct are marked.

Construction of Targeting Plasmids for Activation and Amplification of the TPO Gene The activation of the TPO gene can be accomplished by a number of strategies, as shown in FIGS. 6–8. In the strategy shown in FIG. 6, a targeting fragment is introduced into the genome of recipient cells for insertion of a regulatory region, a non-coding exon, and a functional, unpaired splice-donor site upstream of the TPO coding region. Specifically, the targeting construct from which this fragment is derived (pRTPO1) is designed to include a first targeting sequence homologous to sequences upstream of the TPO gene, an amplifiable marker gene, a selectable marker gene, a regulatory region, a CAP site, a non-coding exon, an unpaired splice-donor site, and a second targeting sequence corresponding to sequences downstream of the first targeting sequence but upstream of TPO exon 1. By this strategy, homologously recombinant cells produce an mRNA precursor which includes the non-coding exon introduced upstream of the TPO gene by homologous recombination, the second targeting sequence and any sequences between the second targeting sequence and exon 2 of the TPO gene, and the remaining exons, introns, and 3' untranslated regions of the TPO gene (FIG. 6). Splicing of this message results in the fusion of the exogenous non-coding exon to exon 2 of the endogenous TPO gene which, when translated, will produce TPO. In this strategy the first and second targeting sequences are upstream of the normal target gene, but this is not required (see below). The size of the intron in the targeting construct and thus the position of the regulatory region relative to the coding region of the gene may be varied to optimize the function of the regulatory region.

Plasmid pRTPO1 is constructed as follows: Based on the restriction map of the TPO upstream region (FIG. 3), a 3.5 kb BamHI fragment can be isolated from subclone pBS(X)/5'Thromb.8 (Example 1). This fragment is ligated to BamHI digested plasmid pBS (Stratagene, Inc., La Jolla, Calif.) and transformed into competent *E. coli* cells to generate pBS-TPO1. This fragment includes sequences lying upstream of TPO exon 1. Next, a 0.73 kb fragment was amplified from hGH expression construct pXGH308, which has the CMV immediate-early (IE) gene promoter region beginning at nucleotide 546 and ending at nucleotide 2105 of Genbank sequence HS5MIEP fused to the hGH sequences beginning at nucleotide 5225 and ending at nucleotide 7322 of Genbank sequence HUMGHCSA, using oligonucleotides 2.1 and 2.2. (The source of the CMV IE gene is not critical, and other CMV IE promoter-based plasmids may be used, or wild-type CMV DNA may be used.) Oligo 2.1 (37 bp, SEQ ID NO: 5), hybridizes to the CMV IE promoter at −614 relative to the cap site (in Genbank sequence HEHCMVP1), and includes a NotI site followed by a partially overlapping XhoI site at its 5' end. Oligo 2.2 (36 bp, SEQ ID NO: 6), hybridizes to the CMV IE promoter at +131 relative to the cap site and includes the first 10 base pairs of the first intron of the CMV IE gene and contains a NotI site at its 5' end. The resulting PCR fragment is digested with NotI and gel-purified. Plasmid pBS-TPO1 is digested with NotI, which cleaves at a single site upstream of TPO exon 1 (FIG. 3), and the digested DNA is ligated to the CMV promoter fragment prepared above and transformed into competent *E. coli* cells. Colonies containing inserts of the CMV promoter inserted at the NotI site of pBS-TPO1 are analyzed by restriction enzyme analysis to confirm the orientation of the insert, and one recombinant plasmid in which the CMV promoter is oriented such that the direction of transcription is towards TPO exon 1 is identified and designated pBS-TPO2.

Oligo 2.1 (SEQ ID NO: 5)
5' TTTT<u>GCGGCC</u> <u>GCTCGAG</u>GAC ATTGATTATT GAC-TAGT
   NotI   XhoI Oligo 2.2 (SEQ ID NO: 6)
5'    TTTT<u>GCGGCC GC</u>CGGTACTT    ACGTCACTCT TGGCAC
      NotI Next, the neomycin phosphotransferase (neo) gene is inserted into pBS-TPO2 for use as a selectable marker in isolating stably transfected human cells. Plasmid pMC1neoPolyA [Thomas, K. R. and Capecchi, M. R. *Cell* 51:503–512 (1987); available from Stratagene Inc., La Jolla, Calif.] is digested with BamHI and made blunt-ended by treatment with the Klenow fragment of *E. coli* DNA polymerase. The treated DNA is then ligated to a double-stranded 10 base pair ClaI linker of the sequence 5'GGATCGATCC, chosen such that the BamHI site is not regenerated by the linker addition. The resulting DNA is digested with ClaI and the digested DNA is ligated under dilute conditions to promote recircularization and transformed into competent *E. coli* cells. Transformed colonies are analyzed by restriction enzyme digestion to identify cells containing a derivative of plasmid pMC1neoPolyA with an insertion of a ClaI site at the 3' end of the neo gene. This plasmid is designated pMC1neo-C. pMC1neo-C is digested with XhoI and SalI and the approximately 1.1 kb fragment containing the neo expression unit is gel purified. Plasmid pBS-TPO2 is digested at the unique XhoI site which was introduced by PCR at the 5' end of the CMV promoter, and the digested DNA is ligated to the purified XhoI-SalI fragment containing the neo gene and transformed into competent *E. coli* cells. Colonies containing inserts of the neo gene inserted at the XhoI site of pBS-TPO2 are analyzed by restriction enzyme analysis to confirm the orientation of the insert, and one recombinant plasmid in which the neo gene is oriented such that the direction of transcription is opposite to CMV is identified and designated pBS-TPO3.

Finally, the targeting construct pTPO1 is constructed by insertion of a dhfr expression unit (to select for amplification in targeted human cells) at the ClaI site located at the 5' end of the neo gene of pBS-TPO3. To obtain a dhfr expression unit, the plasmid construct pF8CIS9080 [Eaton et al., *Biochemistry* 25: 8343–8347 (1986)] is digested with EcoRI and SalI. A 2 kb fragment containing the dhfr expression unit is purified from this digest and made blunt by treatment with the Klenow fragment of DNA polymerase I. A ClaI linker (New England Biolabs, Beverly, Mass.) is then ligated to the blunted dhfr fragment. The products of this ligation are digested with ClaI ligated to ClaI digested pBS-TPO3. An aliquot of this ligation is transformed into *E. coli* and plated on ampicillin selection plates. Bacterial colonies are analyzed by restriction enzyme digestion to determine the orientation of the inserted dhfr fragment. One plasmid with dhfr in a transcriptional orientation opposite that of the neo gene is designated pRTPO1. For targeting to the TPO locus in cultured human cells, pRTPO1 is digested with BamHI to separate the targeting fragment containing the targeting DNA, neo gene, dhfr gene, CMV promoter, and splice-donor site from the pBS plasmid backbone.

A second strategy for activation of the TPO gene is shown in FIG. 7. In this strategy, a targeting fragment is introduced into the genome of recipient cells for insertion of a regulatory region, a non-coding exon, a splice-donor site, an intron, a splice-acceptor site, a second non-coding exon, and a functional, unpaired splice-donor site upstream of the TPO coding region. Specifically, the targeting construct from which this fragment is derived (pRTPO2) is designed to include a first targeting sequence homologous to sequences upstream of the TPO gene, an amplifiable marker gene, a selectable marker gene, a regulatory region, a CAP site, a non-coding exon, a splice-donor site, an intron, a splice-acceptor site, a second non-coding exon, an unpaired splice-donor site, and a second targeting sequence corresponding to sequences downstream of the first targeting sequence but upstream of TPO exon 2. By this strategy, homologously recombinant cells produce an mRNA precursor which corresponds to the first and second non-coding exogenous exons separated by an intron, the second targeting sequence, any sequences between the second targeting sequence and exon 2 of the TPO gene, and the remaining exons, introns, and 3' untranslated regions of the TPO gene (FIG. 7). Splicing of this message results in the fusion of the second non-coding exogenous exon to exon 2 of the endogenous TPO gene which, when translated, will produce TPO. In this strategy the first and second targeting sequences are upstream of the normal target gene, but this is not required (see below). The size of the intron in the targeting construct and thus the position of the regulatory region relative to the coding region of the gene may be varied to optimize the function of the regulatory region.

Plasmid pRTPO2 is constructed as follows: Based on the restriction map of the TPO upstream region (FIG. 3), a 1.8 kb BamHI-EcoRI fragment can be isolated from subclone pBS(X)/5'Thromb.8 (Example 1). This fragment is ligated to BamHI and EcoRI digested plasmid pBS (Stratagene, Inc., La Jolla, Calif.) and transformed into competent *E. coli* cells to generate pBS-TPO4. This fragment includes TPO exon 1 but contains no TPO coding sequences.

Next, oligonucleotides 2.3 to 2.6 are used in PCR to fuse CMV IE promoter sequences beginning at nucleotide 546 and ending at nucleotide 2105 of Genbank sequence HS5MIEP to sequences from the TPO gene comprised of exon 1 and a portion of intron 1. The properties of these primers are as follows: 2.3 (SEQ ID NO: 7) is a 30 base oligonucleotide homologous to a segment of the CMV IE promoter beginning at nucleotide 546 of Genbank sequence HS5MIEP (–614 relative to the cap site) and includes a XhoI site at its 5' end; 2.4 (SEQ ID NO: 8) and 2.5 (SEQ ID NO: 9) are 60 nucleotide complementary primers which define the fusion of CMV (position 2100 of Genbank sequence HS5MIEP) and TPO (position –1881 relative to the TPO translation start site) sequences; 2.6 (SEQ ID NO: 10) is 27 nucleotides in length and is homologous to TPO sequences ending in TPO intron 1 at position –1374 relative to the TPO translation start site and includes a natural ApaI site.

Oligo 2.3 (SEQ ID NO: 7)
5' TTTT<u>CTCGAG</u> GACATTGATT ATTGACTAGT
    XhoI

Oligo 2.4 (SEQ ID NO: 8)
5' catgggtctt ttctgcagtc accgtccttg CTACCCATCT GCTCCCCAGA GGGCTGCCTG Oligo 2.5 (SEQ ID NO: 9)
5° CAGGCAGCCC TCTGGGGAGC AGATGGGTAG caaggacggt gactgcagaa aagacccatg Oligo 2.6 (SEQ ID NO: 10)
5' TTTT<u>GGGCCC</u> TCCTCCCATT ACCCTCT
    ApaI Oligos 2.3–2.6: Bases in lower-case type denote CMV sequences; bases in upper-case type denote TPO sequences These primers are used to amplify a 2.1 kb DNA fragment comprising a fusion of CMV IE and TPO sequences. The fusion fragment is created by first using oligos 2.3 and 2.4 to amplify a 1.6 kb fragment from hGH expression construct pXGH308, which has the CMV immediate-early (IE) gene promoter region beginning at nucleotide 546 and ending at nucleotide 2105 of Genbank sequence HS5MIEP fused to the hGH sequences beginning at nucleotide 5225 and ending at nucleotide 7322 of Genbank sequence HUMGHCSA. (The source of the CMV IE gene is not critical, and other CMV IE promoter-based plasmids may be used, or wild-type CMV DNA may be used.) Then, oligos 2.5 and 2.6 are used to amplify a 0.54 kb fragment containing portions of TPO exon 1 and TPO intron 1 from plasmid pBS(X)/5'Thromb.8 (Example 1). The two amplified fragments are then combined and further amplified using oligos 2.3 and 2.6. The resulting product, a 2.1 kb PCR fragment is digested with XhoI and ApaI and gel purified. Plasmid pMCneo-C (see above) is digested with SalI and XhoI and the 1.1 kb neo containing fragment is gel purified. The purified 2.1 kb PCR fragment and the 1.1 kb neo fragment are then mixed and ligated to pBS-TPO4 (above) which has been cut with SalI and ApaI. The ligation mixture is transformed into *E. coli* cells and a plasmid with a single insert of each the fusion fragment and the neo gene is identified, this plasmid having the SalI site at the 3' end of the neo gene regenerated by ligation to the SalI site in the polylinker of pBS-TPO4. The resulting plasmid is designated pBS-TPO5.

A dhfr expression unit (to select for amplification in targeted human cells) is then inserted at the ClaI site located at the 5' end of the neo gene of pBS-TPO5. The dhfr expression unit is isolated from plasmid pF8CIS9080 [Eaton et al., *Biochemistry* 25: 8343–8347 (1986)] by digestion with EcoRI and SalI. A 2 kb fragment containing the dhfr expression unit is purified from this digest and made blunt by treatment with the Klenow fragment of DNA polymerase I. A ClaI linker (New England Biolabs, Beverly, Mass.) is then ligated to the blunted dhfr fragment. The products of this ligation are digested with ClaI ligated to ClaI digested pBS-TPO5. An aliquot of this ligation is transformed into *E. coli* and plated on ampicillin selection plates. Bacterial colonies are analyzed by restriction enzyme digestion to determine the orientation of the inserted dhfr fragment. One plasmid with dhfr in a transcriptional orientation opposite that of the neo gene is designated pBS-TPO6.

To complete plasmid pRTPO2, plasmid pBS(X)/5'Thromb.8 (Example 1) is partially digested with BamHI and ligated to a SalI linker. The resulting DNA is then digested with SalI and HindIII and the 3.7 kb fragment consisting of sequences upstream of the TPO gene is isolated for use as a second targeting sequence. This fragment is ligated to HindIII-SalI digested pBS-TPO6 to generate the targeting plasmid pRTPO2. For targeting to the TPO locus in cultured human cells, pRTPO2 is digested with HindIII and EcoRI to separate the targeting fragment containing the targeting DNA, neo gene, dhfr gene, and CMV promoter from the pBS plasmid backbone.

A third strategy for activation of the TPO gene is shown in FIG. 8. In this strategy, a targeting fragment is introduced into the genome of recipient cells for replacement of the normal TPO regulatory region, TPO exon 1, TPO intron 1, and TPO exon 2 with an exogenous regulatory region, a coding exon, and a functional, unpaired splice-donor site. Specifically, the targeting construct from which this fragment is derived (pRTPO3) is designed to include a first targeting sequence homologous to sequences upstream of the TPO gene, an amplifiable marker gene, a selectable marker gene, a regulatory region, a CAP site, an exon which includes sequences coding for the first 3⅓ amino acids of the human growth hormone (hGH) signal peptide, an unpaired splice-donor site, and a second targeting sequence corresponding to TPO intron 2 sequences. By this strategy, homologously recombinant cells produce an mRNA precursor which corresponds to the exogenous coding exon, intron 2 of the TPO gene, exon 3 of the TPO gene, and the remaining exons, introns, and 3' untranslated regions of the TPO gene (FIG. 8). Splicing of this message results in the fusion of the exogenous coding exon to exon 3 of the endogenous TPO gene which, when translated, will produce a fusion protein in which the first 3 amino acids of the signal peptide are derived from hGH. The signal peptide of this molecule is cleaved off prior to secretion from a cell to produce mature TPO. In this strategy the first targeting sequence is upstream of the normal target gene, while the second targeting sequence is within the gene, between exons 2 and 3. The position of the first targeting sequence and the amount of upstream DNA replaced or deleted by the targeting event may be varied to optimize the function of the regulatory region.

Plasmid pRTPO3 is constructed as follows: Oligonucleotides 2.8 to 2.11 are used in PCR to fuse CMV IE promoter sequences beginning at nucleotide 546 and ending at nucleotide 1258 of Genbank sequence HS5MIEP to sequences from the human growth hormone gene which encode the first 3⅓ amino acids of the hGH signal peptide, a splice donor site, and the second intron of the TPO gene. The properties of these primers are as follows: Oligo 2.8 (SEQ ID NO: 11) is a 30 base oligonucleotide homologous to a segment of the CMV IE promoter beginning at nucleotide 546 of Genbank sequence HS5MIEP (−614 relative to the cap site) and includes an XhoI site at its 5' end; 2.9 (SEQ ID NO: 12) and 2.10 (SEQ ID NO: 13) are 69 nucleotide complementary primers which define the fusion of CMV (position 2100 of Genbank sequence HS5MIEP) and hGH sequences (position −10 relative to the translation start site of the hGH gene; see the hGH gene N sequence in Genbank entry HUMGHCSA) sequences. These primers also include the first 29 base pairs of TPO intron 2 (nucleotides +14 to +42 relative to the TPO translation start site), which include the splice donor site; 2.11 (SEQ ID NO: 14) is 45 nucleotides in length and is homologous to TPO sequences in TPO intron 2 starting at position +182 relative to the TPO translation start site and extending upstream, and includes a natural EcoRI site at its 5' end.

Figure 3:
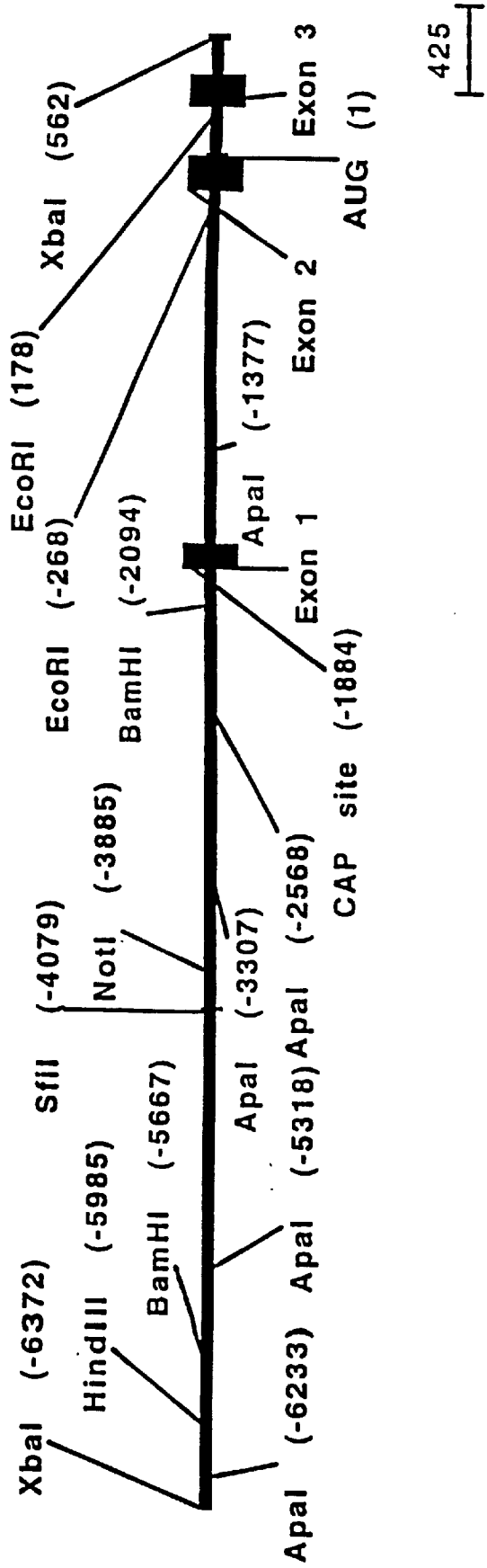
FIG. 3 presents the 6,943 bp genomic XbaI fragment encompassing the 5' flanking region and exons 1, 2, and 3 of the human thrombopoietin (TPO) gene. The XbaI fragment is depicted by the solid line, while exons 1, 2, and 3 are represented by the solid boxes. The nucleotide positions of the ApaI, BamHI, HindIII, EcoRI, NotI, SfiI and XbaI recognition sequences are indicated. Nucleotides are numbered starting at the hTPO ATG initiation codon.

The fusion fragment is created by first using oligos 2.8 and 2.9 to amplify a 0.7 kb fragment from CMV viral DNA containing a wild-type immediate early gene and promoter sequence. (The source of the CMV IE gene is not critical, and other CMV IE promoter-based plasmids may be used.) Then, oligos 2.10 and 2.11 are used to amplify a 0.17 kb fragment containing a portion of TPO intron 2 from plasmid pBS(X)/5'Thromb.8 (Example 1). The two amplified fragments are then combined and further amplified using oligos 2.8 and 2.11. The resulting product, a 0.9 kb PCR fragment is digested with XhoI and EcoRI and gel purified. Next, plasmid a pBS(X)/5'Thromb.8 (Example 1) is partially digested with BamHI and ligated to an XhoI linker. The resulting DNA is then digested with XhoI and HindIII and the 3.9 kb fragment consisting of sequences upstream of the TPO gene is isolated for use as a second targeting sequence. This fragment contains sequences from −5985 to −2095 relative to the TPO translation start site (FIG. 3). The isolated fragment is then ligated in a mixture containing the 0.9 kb fusion fragment purified above and HindIII and EcoRI digested plasmid pBS (Stratagene, Inc., La Jolla, Calif.) and transformed into competent E. coli cells to generate pBS-TPO7.

For insertion of the neo selectable marker gene, plasmid pMC1neo-C (see above) is digested with XhoI and SalI and ligated to XhoI digested pBS-TPO7. The ligation mix is transformed into E. coli cells and colonies are analyzed by restriction enzyme analysis to identify a plasmid with a single insert of the neo gene oriented such that the direction of transcription is opposite to that of the CMV promoter. This plasmid is designated pBS-TPO8.

A dhfr expression unit (to select for amplification in targeted human cells) is then inserted at the ClaI site located at the 5' end of the neo gene of pBS-TPO8. The dhfr expression unit is isolated from plasmid pF8CIS9080 [Eaton et al., *Biochemistry* 25: 8343–8347 (1986)] by digestion with EcoRI and SalI. A 2 kb fragment containing the dhfr expression unit is purified from this digest and made blunt by treatment with the Klenow fragment of DNA polymerase I. A ClaI linker (New England Biolabs, Beverly, Mass.) is then ligated to the blunted dhfr fragment. The products of this ligation are digested with ClaI ligated to ClaI digested pBS-TPO8. An aliquot of this ligation is transformed into E. coli and plated on ampicillin selection plates. Bacterial colonies are analyzed by restriction enzyme digestion to determine the orientation of the inserted dhfr fragment. One plasmid with dhfr in a transcriptional orientation opposite that of the neo gene is designated pRTPO3. For targeting to the TPO locus in cultured human cells, pRTPO3 is digested with EcoRI and HindIII to separate the targeting fragment containing the targeting DNA, neo gene, dhfr gene, CMV promoter, and hGH coding DNA from the pBS plasmid backbone.

Oligo 2.8 (SEQ ID NO: 11)
5' TTTTCTCGAG GACATTGATT ATTGACTAGT
   XhoI

Oligo 2.9 (SEQ ID NO: 12)
5' cgcggattcc ccgtgccaag CCTAGCGGCA ATGGCTACAG
   GTGAGAACAC ACCTGAGGGG CTAGGGCCA Oligo 2.10 (SEQ ID NO: 13)
5' TGGCCCTAGC CCCTCAGGTG TGTTCTACC
   TGTAGCCATT GCCGCTAGGc ttggcacggg gaatccgcg Oligo 2.11 (SEQ ID NO: 14)
5' TTTTGAATTC CCATTCAGGA CCCAGACCTG AAACCCAGGG AATCC
   EcoRI Oligos 2.8–2.11: Bases in lower-case type denote CMV sequences; upper-case, non-bold bases denote TPO sequences; boldface bases denote hGH exon 1 sequences.

Other approaches for targeting and activation of the TPO gene may be employed. For example, the first and second targeting sequences may correspond to sequences in the first or second intron of the TPO gene, and the targeting sequences may include TPO coding sequences. In any activation strategy, the second targeting sequence does not need to lie immediately adjacent to or near the first targeting sequence in the normal gene, such that portions of the gene's normal upstream region are deleted upon homologous recombination. Furthermore, one targeting sequence may be upstream of the gene and one may be within an exon or intron of the TPO gene.

A selectable marker gene is optional and the amplifiable marker gene is only required when amplification is desired. The amplifiable marker gene and selectable marker gene may be the same gene, their positions may be reversed, and one or both may be situated in the intron of the targeting construct. Amplifiable marker genes and selectable marker genes suitable for selection are described herein. The incorporation of a specific CAP site is optional. The regulatory region, CAP site, first non-coding exon, splice-donor site, intron, second non-coding exon, and splice acceptor site may be isolated as a complete unit from the human elongation factor-1a (EF-1a; Genbank sequence HUMEF1A) gene or the cytomegalovirus (CMV; Genbank sequence HEHCMVP1) immediate early region, or the components can be assembled from appropriate components isolated from different genes. In any case, either exogenous exon may be the same or different from the first exon of the normal TPO gene, and multiple non-coding exons may be present in the targeting construct.

As described herein, a number of selectable and amplifiable markers may be used in the targeting constructs, and the activation may be effected in a large number of cell-types.

Example 3

In Vitro Production of TPO by Activation and Amplification of the TPO Gene in an Immortalized Cell Line Transfection of primary, secondary, or immortalized human cells and isolation of homologously recombinant cells expressing TPO may be accomplished using the methods described in U.S. Ser. No. 08/243,391 incorporated by reference. Homologously recombinant cells may be identified by PCR screening strategy as exemplified therein and in published methods available to one skilled in the art (see, for example, Kim, H-S and Smithies, O., *Nucl. Acids Res.* 16:8887–8903 (1988)). The identification of cells expressing TPO may also be accomplished using a variety of assays based on the structure or properties of TPO. For example, TPO may be functionally identified by an in vitro or in vivo megakaryocytopoiesis assay (de Sauvage et al., *Nature* 369:533–538 (1994)). Alternatively, TPO may be assayed by the stimulation of proliferation of cells expressing the c-mpl ligand, the receptor for TPO. In this assay, cells such as Ba/F3-mpl cells (de Sauvage et al., *Nature* 369:533–538 (1994)), are exposed to TPO and cell proliferation is monitored by $^3$H-thymidine uptake. TPO may also be assayed through its effects on in vivo platelet production, either by direct platelet counts or by incorporation of $^{35}$S into platelets. Finally, peptides corresponding to portions of the TPO molecule may be synthesized in order to generate anti-TPO antibodies for use in an ELISA assay.

The isolation of cells containing amplified copies of the amplifiable marker gene and the activated TPO locus is performed as described in U.S. Ser. No. 07/985,586 incorporated by reference.

Example 4

Cloning of the Human DNase I Gene and Identification of the 5' Flanking Sequences The human DNase I gene was isolated from a human genomic DNA library. The library (Clontech, Palo Alto, Calif.; Cat. #HL1006d) was constructed by cloning MboI partially digested male leukocyte DNA into the BamHI site of the bacteriophage lambda vector EMBL3. For library screening, a DNA probe was isolated by PCR amplification of human genomic DNA using oligonucleotides 4.1 and 4.2.
Oligo 4.1 (SEQ ID NO: 15)
5' TGCCTTGAAG TGCTTCTTCA
Oligo 4.2 (SEQ ID NO: 16)
5' CCTCAGAGAT GACGAGAATG C These primers were designed based on the published DNase I mRNA sequence (Shak S. et al., *Proc. Natl. Acad. Sci. USA* 87:9188–9192 (1990)). The amplified probe (probe A; 126 bp) was labeled with $^{32}$P-dCTP by PCR and used to screen a bacteriophage lambda genomic DNA library. The filters were hybridized for 16 hours at 68° C. in 125 mM $Na_2HPO_4$ (pH 7.2), 250 mM NaCl, 10% PEG 8000, 7% SDS, 1 mM EDTA. Filters were washed two times in 500 ml of 20 mM $Na_2HPO_4$ (pH 7.2), 5% SDS, 1 mM EDTA, followed by 4 washes in 500 ml of 20 mM $Na_2HPO_4$ (pH 7.2), 1% SDS, 1 mM EDTA. The wash buffers were preheated to 56° C. and washing was performed at room temperature on a rotary shaker for approximately 5 minutes per wash. The hybridization signals were visualized by autoradiography at −80° C. with an intensifying screen. In this experiment, approximately $1 \times 10^6$ phage were screened and 18 positive signals were obtained. Bacteriophage plaques corresponding to 10 of the positive signals were plated at low density and subjected to a second round of screening using probe A. Four of the phage (designated 2a, 3b, 4c and 14a) gave positive hybridization signals following the secondary screening and were retained for further analysis. DNA was isolated from the plaque purified phage following amplification and subsequent purification by cesium chloride gradient ultra centrifugation (Yamamoto, K. R. et al., *Virology* 40:734 (1970)). Library screening, plaque purification of recombinant bacteriophage and isolation of bacteriophage DNA was performed using standard methods (Ausubel et al., *Current Protocols in Molecular Biology*. Wiley, New York, N.Y. (1987)).

Figure 9:
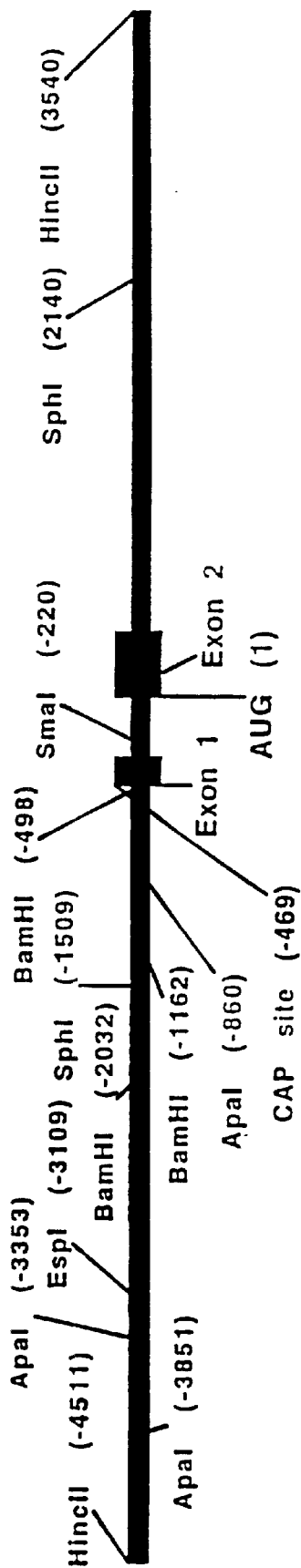
FIG. 9 is a diagrammatic representation of the approximately 8 kb HincII fragment encompassing the 5' flanking region, exons 1 and 2, and the sequences downstream of exon 2 of the human DNase I gene. The HincII fragment is depicted by the solid line, while exons 1 and 2 are represented by solid rectangular boxes. The nucleotide positions of the ApaI, BamHI, HincII, EspI, SphI and SmaI recognition sequences are indicated. Nucleotides are numbered starting at the AUG initiation codon. The nucleotide positions which reside upstream of exon 2 are based on the DNA sequence presented in FIGS. 10 and 11.

Based on restriction enzyme digestion and Southern blot analysis using probe A, two of the phage (4c and 14a) contain a common HincII fragment of approximately 8 kb which encompasses exon 1, intron 1, exon 2, coding and non-coding sequences corresponding to intron 2 and downstream DNase I exons, as well as approximately 4 kb of non-transcribed DNA lying upstream of DNase I exon I. This fragment was isolated from one genomic clone (4c) and subcloned into pBSIISK+ (Stratagene Inc., La Jolla, Calif.) for further analysis. Restriction enzyme mapping of the resultant clone, pBS/4C.2Hinc2, was used to generate the restriction map shown in FIG. 9. The nucleotide sequence of the non-transcribed DNase I 5' region lying upstream of the 5' end of the known cDNA sequence is shown in FIG. 10 (SEQ ID NO: 17). The nucleotide sequence lying downstream of the 5' end of the known cDNA sequence, including exon 1, intron 1 and part of exon 2 is shown in FIG. 11 (SEQ ID NO: 18). Comparison of the cloned genomic sequence presented here, with the published cDNA sequence (Shak, S. et al., *Proc. Natl. Acad. Sci. USA* 87:9188–9192 (1990)) reveals that the 5' end of the DNase I gene consists of a non-coding exon (exon 1) of 142 bp and a second exon (exon 2) which is at least 341 bp. Exon 2 encodes a 22 amino acid signal sequence and a portion of the mature DNase I peptide, beginning with an AUG translational initiation codon which lies 1 bp downstream of the 5' end of exon 2. Exons 1 and 2 are separated by intron 1 which is 336 bp in length.

Example

Figure 12:
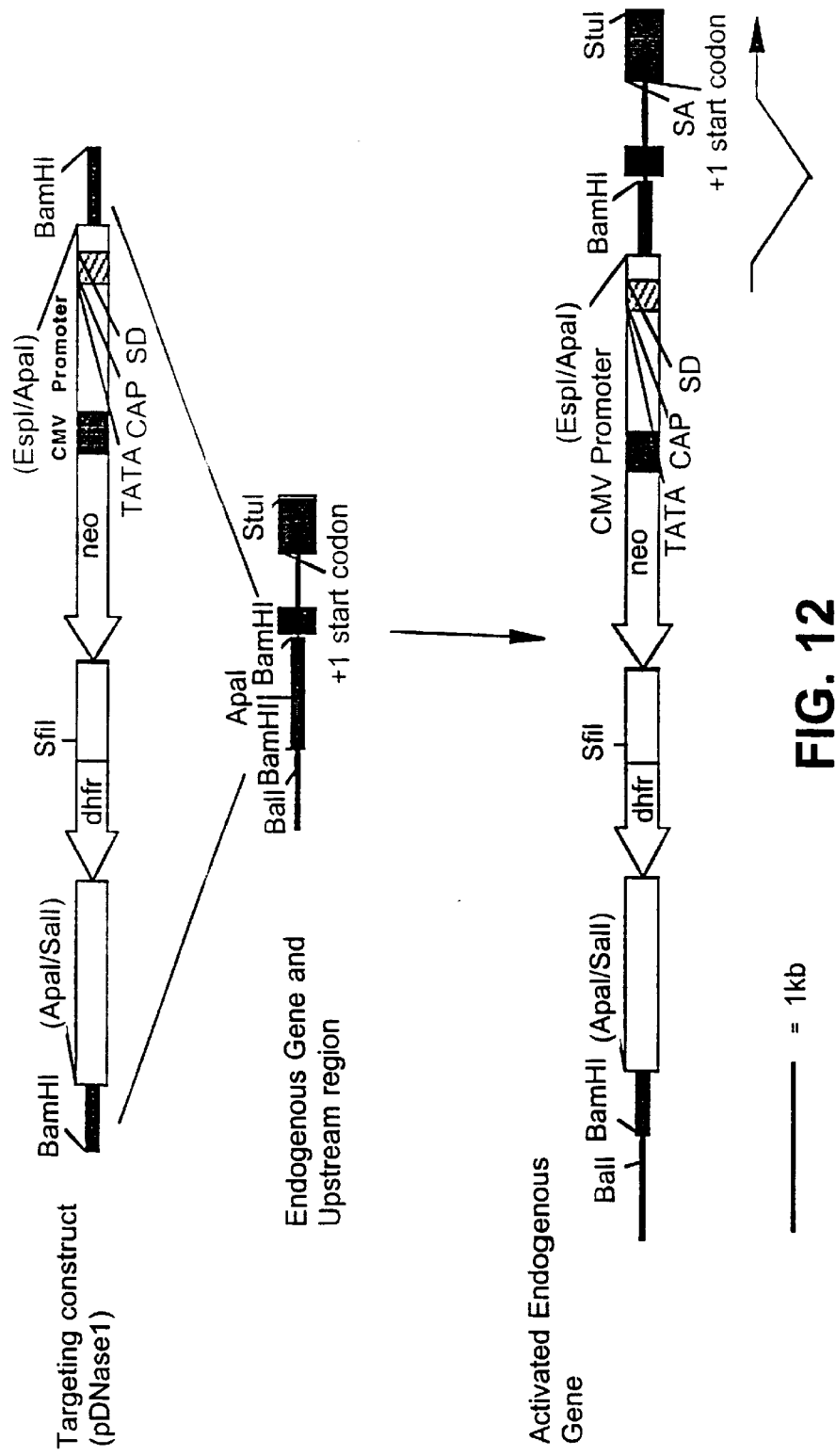
FIG. 12 shows a strategy for activation of the human DNase I gene by homologous recombination. The targeting fragment is a 4633 bp BamHI fragment from pDNaseI which contains; 283 bp of 5' targeting sequence from position –1162 (BamHI site) to –860 (ApaI site), an amplifiable dhfr expression unit, neo gene, CMV IE promoter, a CAP site, a non-codon exon, an unpaired splice-donor site and 363 bp of 3' targeting sequence from position –860 (EspI site) to –468 (BamHI site). The dhfr expression unit and the neo gene are depicted by open arrows, the orientation of the arrows represent the direction of transcription. The positions of the CMV promoter, TATA box, CAP site and splice donor sequence (SD) are indicated. Activation of the DNase I gene is achieved by integration of the targeting fragment into the genome of the recipient cells by homologous recombination. The targeted gene product is depicted in the lower panel of the figure. The mRNA precursor which includes a non-coding 5' exon, a chimeric intron and exon 2 of the DNase gene, is represented by the thin arrow.

Construction of Targeting Plasmids for Activation and Amplification of the DNase I Gene The activation of the DNase I gene can be accomplished by the strategy outlined in FIG. 12. In this strategy, a targeting fragment is introduced into the genome of recipient cells for insertion of a regulatory region, a non-coding exon and a functional unpaired splice-donor site upstream of the DNase I coding region. Specifically, the targeting construct from which this fragment is derived (pDNase1), is designed to include a 5' targeting sequence homologous to sequences upstream of the DNase I gene, a selectable marker gene, an amplifiable marker gene, a regulatory region, a CAP site, a non-coding exon, an unpaired splice-donor site, and a 3' targeting sequence corresponding to sequences downstream of the 5' targeting sequence but upstream of DNase I exon 1. According to this strategy, integration of the targeting construct by homologous recombination generates recombinant cells producing an mRNA precursor which includes the non-coding exon introduced upstream of the DNase I gene, the 3' targeting sequence, any sequences between the 3' targeting sequence and exon 2 of the DNase I gene, and the remaining exons, introns and 3' untranslated regions of the DNase I gene (FIG. 12). Splicing of this transcript results in the fusion of the exogenous non-coding exon to exon 2 of the endogenous DNase I gene. DNase I is produced by translation of the mature mRNA. According to this strategy, both the 5' and 3' targeting sequences are upstream of the endogenous target gene. The size of the chimeric intron in the targeting construct, which is dictated by the position of the regulatory region relative to the coding sequence, may be varied to optimize the function of the regulatory region.

Plasmid pCND1, which contains the activation cassette, is constructed as follows: A 1555 bp (size includes a 9 bp synthetic HindIII recognition site at the 5' end of oligo 5.2) fragment is amplified using oligos 5.1 and 5.2. The amplified fragment encompasses the CMV IE promoter, CMV IE exon 1 (non-coding exon) and 827 bp of CMV IE intron 1, beginning at nucleotide 172,783 and ending at nucleotide 174,328 of EMBL sequence X17403 ((Human cytomegalovirus strain AD169). (The source of the CMV IE gene is not critical, and CMV IE promoter-based plasmids or wild-type CMV DNA may be used.) Oligo 5.1 (21 bp, SEQ ID NO: 19) hybridizes to the CMV IE promoter at –598 relative to the CAP site (EMBL sequence X17403). Oligo 5.2 (32 bp, SEQ ID NO: 20) contains 23 nucleotides which hybridize to the CMV IE promoter at +946 relative to the CAP site, the additional 9 bp at the 5' end of the oligo create a synthetic HindIII recognition sequence. The 1555 bp PCR product is digested with HindIII and the resultant 1551 bp fragment is purified and used in the ligation described below. Next, the neomycin phosphotransferase (neo) gene is isolated from plasmid pBSneo for use as a selectable marker for the isolation of stably transfected human cells. The neo gene in plasmid pBSneo was obtained by BamHI and XhoI digestion of pMC1neo-polyA (Thomas, K. R. and Capecchi, M. R. *Cell* 51:503–512 (1987)). Plasmid pMC1neo-polyA was digested with BamHI and made blunt ended with the Klenow fragment of *E. coli* DNA polymerase I. The resulting DNA was digested with XhoI, and the blunt-ended BamHI-XhoI fragment was cloned into HincII and XhoI digested plasmid pBSIISK⁺. For isolation of the neo gene harbored on pBSneo, plasmid pBSneo is digested with XhoI and made blunt-ended by treatment with the Klenow fragment of *E. coli* DNA polymerase I. The resulting DNA is digested with HindIII and an 1165 bp fragment containing the neo expression unit is gel purified. The 1165 bp neo fragment and the 1551 bp CMV promoter, fragment are ligated, the ligation products are digested with HindIII and the 2716 bp HindIII fragment, resulting from blunt-end ligation of the two fragments, is gel purified. The 2716 bp HindIII product is ligated to HindIII digested plasmid pBSIISK⁺ (Stratagene Inc., La Jolla, Calif.) and electroporated into *E. coli*. Colonies containing inserts in the HindIII site of pBSIISK⁺ are analyzed by restriction enzyme analysis to confirm the orientation of the insert. One recombinant plasmid in which the CMV promoter is oriented such that the oligo 5.2 sequences (+946 relative to the CMV IE CAP site) are proximal to the SalI recognition sequence in the pBSIISK⁺ polylinker, is identified and designated pCN1.
Oligo 5.1 (SEQ ID NO: 19)
5' GACATTGATT ATTGACTAGT T
Oligo 5.2 (SEQ ID NO: 20)
5' TTTAAGCTTC TGCAGAAAAG ACCCATGGAA AG Next, the dhfr expression unit is inserted at a ClaI site which is located at the 3' end of the neo gene of pCN1. The dhfr expression unit is obtained by EcoRI and SalI digestion of plasmid pF8CIS9080 (Eaton et al., *Biochemistry* 25:8343–8347 (1986)). The resultant 2 kb fragment is purified from the digest and made blunt with the Klenow fragment of *E. coli* DNA polymerase I. A ClaI linker (5' CCATCGATGG (NEB 1088; New England Biolabs, Beverly, Mass.) is ligated to the blunt-end dhfr fragment and the ligation products are digested with ClaI. pCN1 is digested with ClaI, and the ClaI dhfr containing fragment is ligated into ClaI site of pCN1. An aliquot of the ligation reaction is electroporated into *E. coli* and colonies harboring inserts in a ClaI site of pCN1 are analyzed by restriction enzyme analysis to determine the site of insertion and the orientation of the insert. A plasmid with the dhfr expression unit at the 3' end of the neo gene and with the same transcriptional orientation as that of the neo gene is identified and designated pCND1.

Plasmid pDNase1 is constructed as follows: Based on the restriction map of the upstream region of the DNase I gene (FIG. 9), a 664 bp BamHI fragment (–1161 to –498 in FIG. 8) can be isolated from subclone pBS/4C.2Hinc2. This fragment is ligated to BamHI digested plasmid pBSIISK⁺ dApaI (modification of pBSIISK⁺; Stratagene Inc., La Jolla, Calif.) in which the ApaI recognition sequence in the polylinker is destroyed. pBSIISK⁺dApaI is constructed by digesting pBSIISK⁺ with ApaI, conversion of the cohesive-ends to blunt-ends with T4 DNA polymerase and ligation to generate the circular plasmid. Following ligation of the 664 bp BamHI fragment into pBSIISK⁺dApaI, the ligation products are electroporated into *E. coli* cells to generate pBS- DNase1. The sequences contained in this fragment reside upstream of DNase I exon 1, position −1162 to −498 with respect to the AUG translational initiation codon (nucleotide +1). The activation cassette which contains the CMV immediate-early (IE) promoter region, the CMV IE CAP site, a non-coding exon, an unpaired splice donor site, the neomycin phosphotransferase (neo) selectable marker gene and dhfr expression unit (to select for amplification in targeted human cells) is cloned into the unique ApaI site of the 664 bp BamHI fragment (DNase I upstream region) in pBS-DNase1 (see FIG. 12). Specifically, plasmid pCND1 which contains the activation cassette, is digested with SalI which cuts downstream of the dhfr expression unit and EspI which cuts 242 bp downstream of the CMV IE CAP site. A 3,955 bp SalI-EspI fragment containing the activation cassette is purified from this digest and the cohesive-ends are made blunt by treatment with the Klenow fragment of *E. coli* DNA polymerase I. This fragment is ligated to plasmid pBS-DNase1, which has been digested with ApaI and made blunt-ended by treatment with T4 DNA polymerase I, and electroporated into *E. coli*. Colonies containing inserts of the activation cassette inserted at the blunt-ended ApaI site of pBS-DNase 1 are analyzed by restriction enzyme analysis to confirm the orientation of the insert. One recombinant plasmid in which the CMV promoter is oriented such that the direction of transcription is towards DNase I exon 1 is identified and designated pDNase1.

Plasmid pDNase1 is digested with BamHI for transfection into human cells. Transfection of primary, secondary, or immortalized human cells and isolation of homologously recombinant cells expressing DNase I may be accomplished using the methods described in U.S. Ser. No. 08/243,391 and incorporated herein by reference. Homologously recombinant cells may be identified by PCR screening strategy as exemplified therein and in published methods available to one skilled in the art (see, for example, Kim, H-S and Smithies, O., *Nucl. Acids Res.* 16:8887–8903 (1988)). The identification of cells expressing DNase I may also be accomplished using a variety of assays based on the structure or properties of DNase I. For example, DNase I may be functionally identified by an in vitro enzyme assay (cf. Kunitz, *J. Gen. Physiol.* 33: 349 (1950); McDonald, *Meth. Enzymol.* 2:437 (1955)) or by the use of anti-DNase I antibodies in an ELISA assay.

The isolation of cells containing amplified copies of the amplifiable marker gene and the activated DNase I locus is performed as described in U.S. Ser. No.: 07/985,586 incorporated herein by reference.

Example 6

Cloning of the Human β-Interferon Gene and Identification of the 5' Flanking Sequences The human β-interferon gene was isolated from a human genomic DNA library. The library (Clontech, Palo Alto, Calif.; Cat. #HL1006d) was constructed by cloning MboI partially digested male leukocyte DNA into the BamHI site of the bacteriophage lambda vector EMBL3. For library screening, a DNA probe was isolated by PCR amplification of human genomic DNA using oligonucleotides 6.1 and 6.2
Oligo 6.1 (SEQ ID NO: 21)
5' TGCTCTGGCA CAACAGGTAG
Oligo 6.2 (SEQ ID NO: 22)
5' CATAGATGGT CAATGCGGC
These primers were designed based on the published β-interferon mRNA sequence (May, L. T. and Sehgal, P. B., *J. Interferon Res.* 5:521–526 (1985)). The amplified probe (probe A; 290 bp) was labeled with $^{32}$P-dCTP by PCR and used to screen a bacteriophage lambda genomic DNA library. The filters were hybridized for 16 hours at 68° C. in 125 mM $Na_2HPO_4$ (pH 7.2), 250 mM NaCl, 10% PEG 8000, 7% SDS, 1 mM EDTA. Filters were washed two times in 500 ml of 20 mm $Na_2HPO_4$ (pH 7.2), 5% SDS, 1 mM EDTA, followed by 4 washes in 500 ml of 20 mM $Na_2HPO_4$ (pH 7.2), 1% SDS, 1 mM EDTA. The wash buffers were preheated to 56° C. and washing was performed at room temperature on a rotary shaker for approximately 5 minutes per wash. The hybridization signals were visualized by autoradiography at −80° C. with an intensifying screen. In this experiment, approximately $1\times10^6$ phage were screened and 6 positive signals were obtained. Bacteriophage plaques corresponding to the positive signals were plated at low density and subjected to a second round of screening using probe A. Five of the phage (designated 1a, 2a, 2b, 11a, and 12a) gave positive hybridization signals following the secondary screening and were retained for further analysis. DNA was isolated from the plaque purified phage following amplification and subsequent purification by cesium chloride gradient ultra centrifugation (Yamamoto, K. R. et al., *Virology* 40:734 (1970)). Library screening, plaque purification of recombinant bacteriophage and isolation of bacteriophage DNA was performed using standard methods (Ausubel et al., *Current Protocols in Molecular Biology*. Wiley, New York, N.Y. (1987)).

Figure 13:
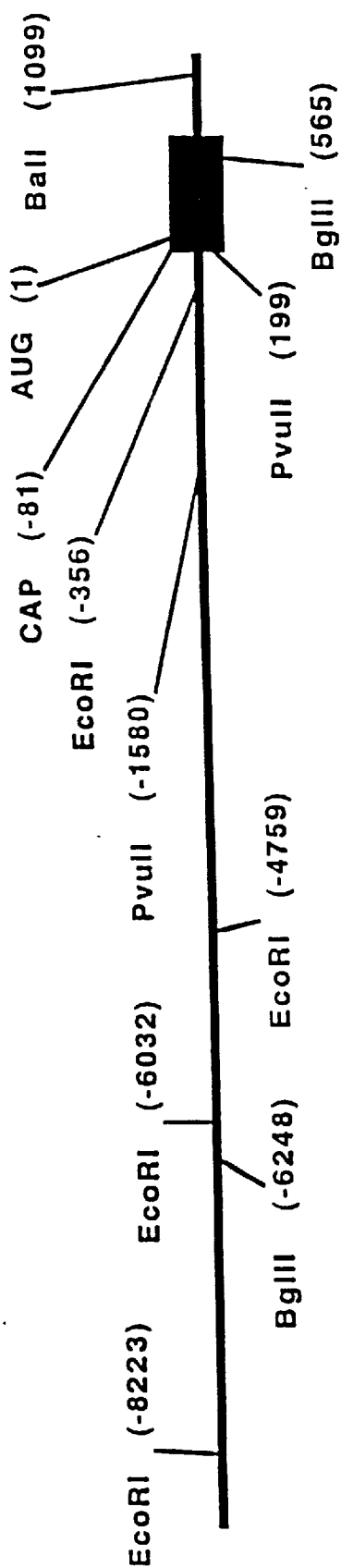
FIG. 13 is a diagrammatic representation of 9,939 bp encompassing the 5' flanking region, coding sequence and the 3' untranslated region of the human β-interferon gene. The 5' and 3' flanking regions are depicted by the solid line and the transcribed region is represented by the solid box. The nucleotide positions of the BalI, BglII, EcoRI and PvuII recognition sequences are indicated. Nucleotides are numbered starting at the β-interferon ATG translational initiation codon (see FIG. 15).

Based on restriction enzyme digestion and Southern blot analysis using probe A, all five of the phage (1a, 2a, 2b, 11a, and 12a) were shown to contain a common HindIII fragment of approximately 10 kb which encompasses the entire sequence coding for β-interferon (561 bp), 666 bp of 3' untranslated sequence and approximately 9 kb of non-transcribed DNA lying upstream of the β-interferon gene. This fragment was isolated from one genomic clone (1a) and subcloned into pBSIISK$^+$ (Stratagene Inc., La Jolla, Calif.) for further analysis. The resultant clones, pBS-H3/Bint.11-3 and pBS-H3/Bint.11-21, harbor the 10 kb HindIII fragment in opposite orientations with respect to the plasmid backbone. Restriction enzyme mapping was used to generate the restriction map shown in FIG. 13. The nucleotide sequence of 8,355 bp of DNA lying upstream of the previously reported sequence (Genbank entry HUMIFNB1F) is shown in FIG. 14 (SEQ ID NO: 23). The nucleotide sequence corresponding to 356 bp of DNA upstream of the β-interferon coding region, the β-interferon coding region, and 666 bp of 3' untranslated sequence is shown in FIG. 15 (SEQ ID NO: 24). Comparison of the cloned genomic sequence presented here, with the published cDNA sequence (May, L. T. and Sehgal, P. B., *J. Interferon Res.* 5:521–526 (1985)) confirms that the β-interferon gene consists of a 561 bp coding region SEQ ID NO:30 which is co-linear with its cognate mRNA (lacks introns). The β-interferon gene encodes a 21 amino acid signal sequence and a 120 amino acid mature peptide, beginning with an AUG translational initiation codon which lies 82 bp downstream of the CAP site.

Example 7

Figure 16:
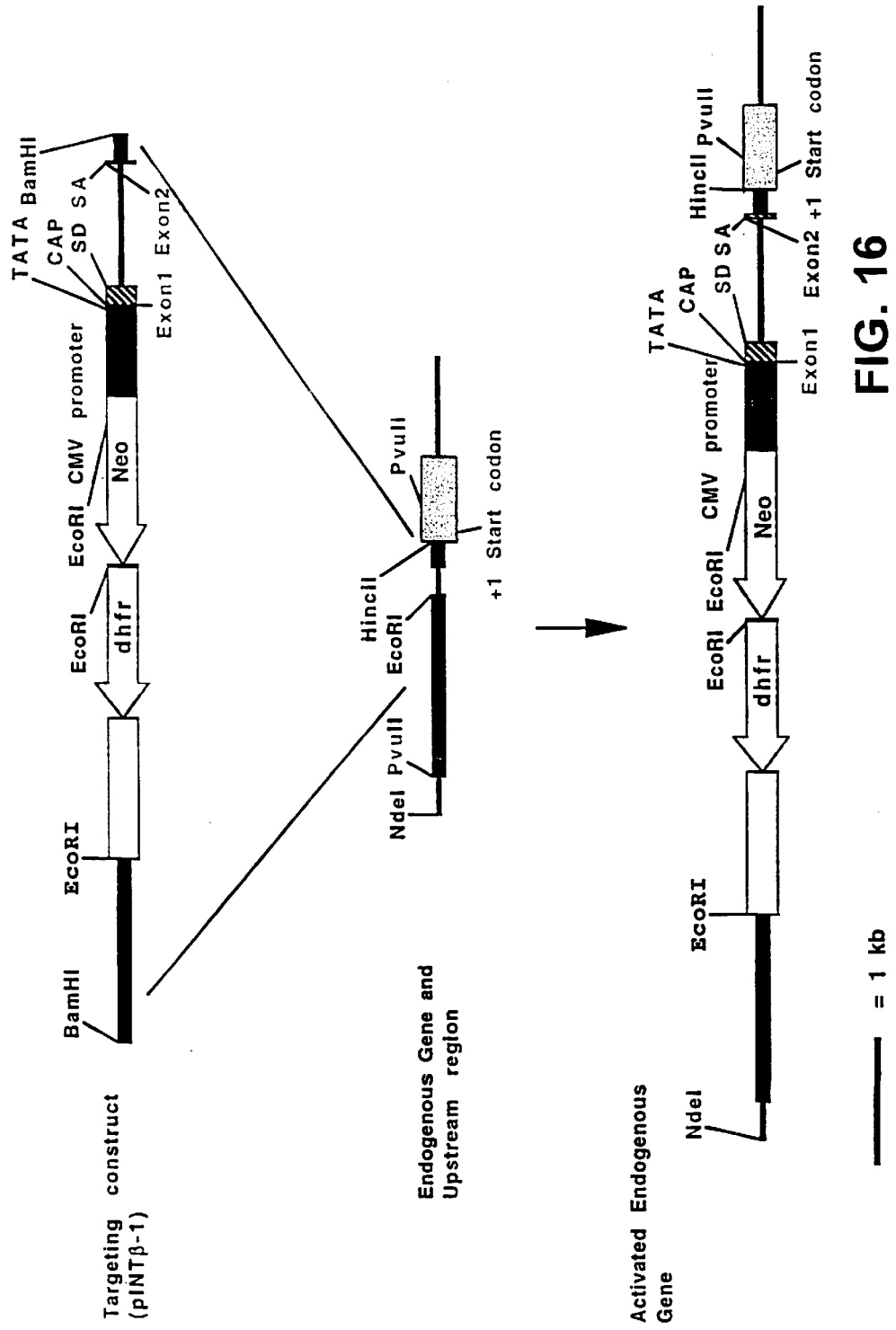
FIG. 16 depicts the strategy for activation of the human β-interferon gene by homologous recombination using targeting construct pIFNb-1 as described in Example 7. The positions of the TATA box, CAP site, dhfr and neo markers, the exogenous CMV promoter, and the β-interferon 5' flanking region and coding sequence are indicated. Thick lines: targeting sequences; thin lines: intron, β-interferon 5' and 3' non-coding sequences; solid box: CMV promoter; shaded box: endogenous β-interferon transcribed region; cross-hatched box: non-coding CMV exon 1 and the chimeric exon 2. The splice-donor site (SD) of the exogenous exon and the splice-acceptor site (SA) flanking the chimeric exon 2 are indicated. Recognition sites for BamHI, EcoRI, HincII, NdeI and PvuII which are relevant to the construction of the targeting construct are marked.

Construction of Targeting Plasmids for Activation and Amplification of the β-Interferon Gene The activation of the β-interferon gene can be accomplished by the strategy outlined in FIG. 16. In this strategy, a targeting fragment is introduced into the genome of recipient cells for replacement of the endogenous β-interferon regulatory region with an exogenous regulatory region, a non-coding exon, an intron, and chimeric exon sequences consisting of sequences from a noncoding exon (derived from exon 2 of the CMV IE gene) and sequences from the β-interferon 5' noncoding region. Specifically, the targeting construct from which this fragment is derived (pIFNβ-1) is designed to include a 5' targeting sequence homologous to sequences upstream of the β-interferon gene, a selectable marker gene, an amplifiable marker gene, a regulatory region, a CAP site, a non-coding exon, an intron, chimeric exon sequences consisting of CMV IE exon 2 sequences and β-interferon 5' noncoding DNA, and a 3' targeting sequence homologous to DNA upstream of the β-interferon coding region. According to this strategy, integration of the targeting construct by homologous recombination generates recombinant cells producing an mRNA precursor which includes the non-coding exon introduced upstream of the β-interferon gene, an intron, the chimeric exon which fuses CMV IE exon sequences to β-interferon 5' noncoding sequences and the entire β-interferon coding region, and 3' untranslated regions of the β-interferon gene (FIG. 16). The chimeric exon consists of 17 bp of CMV IE exon 2 (position 172,782 to 172,766 of EMBL sequence X17403) joined to the 5' flanking region of the β-interferon gene (position −173 with respect to the AUG translational initiation codon). Splicing of this transcript results in the fusion of the exogenous non-coding exon to exon 2 which includes the complete coding sequence of the endogenous β-interferon gene. β-interferon is produced by translation of the mature mRNA. According to this strategy, the 5' targeting sequence is upstream of the endogenous target gene and the 3' targeting sequence is in the β-interferon 5' noncoding region. The position of the regulatory region relative to the 5' flanking sequence, may be varied (e.g. by altering the size of the intron in the targeting construct) to optimize the function of the regulatory region.

Plasmid pIFNβ-1 is constructed as follows: A 182 bp fragment (size includes a 9 bp synthetic BamHI recognition site at the 5' end of Oligo 7.1) is amplified from pBS-H3/Bint.11-3 using oligos 7.1 and 7.2. The amplified fragment serves as the 3' targeting sequence (FIG. 16). Oligo 7.1 (21 bp, SEQ ID NO: 25) hybridizes to the β-interferon 5' non-transcribed region at position −173 with respect to the β-interferon AUG translational initiation codon (FIG. 15). Oligo 7.2 (30 bp, SEQ ID NO: 26) contains 21 nucleotides which hybridize to the β-interferon 5' untranslated region at position −1 relative to the AUG translational start codon (see FIG. 16), with the additional 9 bp at the 5' end of the oligo creating a synthetic BamHI recognition sequence. The 182 bp PCR product is purified and used in the ligation described below. Next, a 1571 bp (size includes an 8 bp synthetic SmaI recognition sequence at the 5' end of oligo 7.3) fragment is amplified using oligos 7.3 and 7.4. The amplified fragment encompasses the CMV IE promoter, CMV IE exon 1 (non-coding exon), CMV IE intron 1 and 17 bp of CMV IE exon 2, beginning at nucleotide 174,328 and ending at nucleotide 172,766 of EMBL sequence X17403 (Human cytomegalovirus strain AD 169). (The source of the CMV IE gene is not critical, and CMV IE promoter-based plasmids or wild type CMV DNA may be used). Oligo 7.3 (29 bp, SEQ ID NO: 27) contains 21 nucleotides which hybridize to the CMV IE promoter at −598 relative to the CAP site (EMBL sequence X17403), the 5' end of the oligo also contains a 8 bp synthetic SmaI recognition sequence. Oligo 7.4 (21 bp, SEQ ID NO: 28) hybridizes to the CMV IE promoter at +965 relative to the CAP site. The 1571 bp PCR product containing the CMV IE promoter, CMV IE exon 1, CMV IE intron 1 and 23 bp of CMV IE exon 2, is gel purified and ligated to the 182 bp fragment containing the β-interferon 5' flanking region. The ligation products are digested with BamHI and SmaI, and the 1742 bp SmaI-BamHI fragment, resulting from ligation of β-interferon sequences (position −173 with respect to the AUG translational initiation codon) to CMV IE sequences (−598 relative to the CMV IE CAP site), is gel purified. The 1742 bp SmaI-BamHI fragment is ligated to BamHI and SmaI digested plasmid pBSIISK+ (Stratagene Inc., La Jolla, Calif.) and electroporated into E. coli. Colonies containing inserts in PBSIISK+ are analyzed by restriction enzyme analysis to confirm the structure of the insert. One recombinant plasmid is identified and designated pBS-CB.

Oligo 7.1 (SEQ ID NO: 25)
5' TGACATAGGA AAACTGAAAG G
Oligo 7.2 (SEQ ID NO: 26)
5' TTTGGATCCG TTGACAACAC GAACAGTGTC G
Oligo 7.3 (SEQ ID NO: 27)
5' TTTCCCGGGA CATTGATTAT TGACTAGTT
Oligo 7.4 (SEQ ID NO: 28)
5° CGTGTCAAGG ACGGTGACTG C The neomycin phosphotransferase (neo) gene is isolated from plasmid pBSneo for use as a selectable marker for the isolation of stably transfected human cells. The neo gene in plasmid pBSneo was obtained by BamHI and XhoI digestion of pMC1neo-polyA (Thomas, K. R. and Capecchi, M. R., *Cell* 51:503–512 (1987)). Plasmid pMC1neo-polyA was digested with BamHI and made blunt ended with the Klenow fragment of *E. coli* DNA polymerase I. The resulting DNA was digested with XhoI, and the blunt-ended BamHI-XhoI fragment was cloned into HincII and XhoI digested plasmid PBSIISK+. For isolation of the neo gene harbored on pBSneo, plasmid pBSneo is digested with XhoI and made blunt-ended by treatment with the Klenow fragment of *E. coli* DNA polymerase I. The resulting DNA is digested with HindIII and a 1165 bp fragment containing the neo expression unit is gel purified. The 1165 bp fragment is ligated to SmaI and HindIII digested plasmid pBS-CB and electroporated into *E. coli*. Colonies containing inserts in pBS-CB are analyzed by restriction enzyme analysis to confirm the orientation of the insert. One recombinant plasmid is identified and designated pBS-CBN.

Next, the dhfr expression unit is inserted at the ClaI site which is located at the 3' end of the neo gene of pBS-CBN. The dhfr expression unit is obtained by EcoRI and SalI digestion of plasmid pF8CIS9080 (Eaton et al., *Biochemistry* 25:8343–8347 (1986)). The resultant 2 kb fragment is purified from the digest and made blunt with the Klenow fragment of *E. coli* DNA polymerase I. A ClaI linker (5' CCATCGATGG; NEB 1088, New England Biolabs, Beverly, Mass.) is ligated to the blunt-end dhfr fragment, the ligation products are digested with ClaI and purified. The ClaI dhfr containing fragment is ligated into ClaI digested plasmid pBS-CBN. An aliquot of the ligation reaction is electroporated into *E. coli* and colonies harboring inserts in a ClaI site of pBS-CBN are analyzed by restriction enzyme analysis to determine the site of insertion and the orientation of the insert. A plasmid with the dhfr expression unit at the 3' end of the neo gene and with the same transcriptional orientation as that of the neo gene is identified and designated pBS-CBND.

Finally, the targeting construct is constructed by insertion of the 5' targeting sequence (FIG. 16) in the unique SalI site located at the 3' end of the dhfr expression unit in plasmid pBS-CBND. To obtain the 5' targeting sequence, the plasmid pBS-H3/Bint.11-3 is digested with EcoRI and PvuII and the resultant 1.2 kb fragment is purified, ligated to EcoRI-SmaI digested plasmid pBSIISK⁺ (Stratagene Inc., La, Jolla, Calif.) and electroporated into *E. coli*. Colonies containing inserts in pBSIISK⁺ are analyzed by restriction enzyme analysis, and one plasmid containing the insert is retained and designated pBS-BI5. Plasmid pBS-BI5 is digested with SpeI and EcoRV and made blunt-ended with the Klenow fragment of DNA polymerase I. The resulting 1.2 kb fragment is ligated to SalI digested plasmid pBS-CBND, which has been made blunt-ended with the Klenow fragment of *E. coli* DNA polymerase I. An aliquot of the blunt-end ligation reaction is electroporated into *E. coli* and colonies harboring inserts in the SalI site of pBS-CBND are analyzed by restriction enzyme analysis to determine the orientation of the insert. A plasmid with the EcoRI site at the 3' end of the dhfr expression unit is identified and designated pIFNβ-1.

Plasmid pIFNβ-1 is digested with BamHI for transfection into human cells. Transfection of primary, secondary, or immortalized human cells and isolation of homologously recombinant cells expressing β-interferon may be accomplished using the methods described in U.S. Ser. No. 08/243,391 and incorporated herein by reference. Homologously recombinant cells may be identified by PCR screening strategy as exemplified therein and in published methods available to one skilled in the art (see, for example, Kim, H-S and Smithies, O., *Nucl. Acids Res.* 16:8887–8903 (1988)). The identification of cells expressing β-interferon may also be accomplished using a variety of assays based on the structure or properties of β-interferon. For example, β-interferon may be identified by an in vitro reverse passive hemagglutination assay (Accurate Chemical Corp., Westbury, N.Y.), stimulation of superoxide anion production by mouse peritoneal macrophages (Colligan, J. E. et al. *Current Protocols in Immunology*, Wiley, New York, N.Y. (1994), or by using anti-β-interferon antibodies in an ELISA assay.

The isolation of cells containing amplified copies of the amplifiable marker gene and the activated β-interferon locus is performed as described in U.S. Ser. No. 07/985,586 incorporated herein by reference.

EQUIVALENTS

Those skilled in the art will recognize, or be able to ascertain using not more than routine experimentation, many equivalents to the specific embodiments of the invention described herein. Such equivalents are intended to be encompassed by the following claims.

What is claimed is:

1. A DNA construct which alters the expression of a targeted gene in a cell when the DNA construct is homologously recombined with a target site within the chromosomal DNA of the cell, the DNA construct comprising:

(a) a targeting sequence homologous to the target site;
(b) an exogenous regulatory sequence;
(c) an exon; and
(d) an unpaired splice-donor site at the 3' end of the exon; wherein following homologous recombination of the targeting sequence with the target site, the chromosomal DNA of the cell comprises the construct-derived exon in addition to all endogenous exons of the targeted gene.

2. The DNA construct of claim 1, wherein the DNA construct is linear.

3. The DNA construct of claim 1, wherein the exon sequence does not overlap with the targeting sequence.

4. The DNA construct of claim 1, wherein (a), (b), (c), and (d) are oriented such that, upon homologous recombination of the targeting sequence with the target site, the exogenous regulatory sequence controls expression of the targeted gene to produce a transcript comprising RNA corresponding to the construct-derived exon, construct-derived splice-donor site, and coding sequence of the targeted gene, wherein the RNA corresponding to the construct-derived splice-donor site of the transcript directs splicing to a splice-acceptor site in the transcript which corresponds to a site within the targeted gene.

5. The DNA construct of claim 4, wherein the splice-acceptor site of the transcript corresponds to the splice-acceptor site of the second exon of the targeted gene.

6. A DNA construct which alters the expression of a targeted gene in a cell when the DNA construct is homologously recombined with a target site within the chromosomal DNA of the cell, the DNA construct comprising:

(a) a targeting sequence homologous to the target site;
(b) an exogenous regulatory sequence;
(c) an exon; and
(d) an unpaired splice-donor site at the 3' end of the exon, wherein following homologous recombination of the targeting sequence with the target site, (b)–(d) are positioned upstream of the endogenous transcription initiation site of the targeted gene.

7. The DNA construct of claim 6, wherein (a), (b), (c), and (d) are oriented such that, upon homologous recombination of the targeting sequence with the target site, the exogenous regulatory sequence controls expression of the targeted gene to produce a transcript comprising RNA corresponding to the construct-derived exon, construct-derived splice-donor site, and coding sequence of the targeted gene, wherein the construct-derived splice-donor site of the transcript directs splicing to a splice-acceptor site in the transcript which corresponds to a site within the targeted gene.

8. The DNA construct of claim 7, wherein the splice-acceptor site of the transcript corresponds to the splice-acceptor site of the second exon of the targeted gene.

9. The DNA construct of claim 8, wherein the exon of the construct comprises coding sequence which, upon splicing of the construct-derived splice-donor site with the endogenous splice-acceptor site, is in-frame with coding sequence of the targeted gene.

10. The DNA construct of claim 9, wherein the exon of the construct comprises coding sequence that is the same as the coding sequence of the first exon of the targeted gene.

11. The DNA construct of claim 9, wherein the coding sequence of the exon of the construct is different from the coding sequence of the first exon of the targeted gene.

12. The DNA construct of claim 6, wherein the exon sequence does not overlap with the targeting sequence.

13. The DNA construct of claim 6, wherein the exon comprises a CAP site.

14. The DNA construct of claim 13, wherein the exon further comprises the nucleotide sequence ATG.

15. The DNA construct of claim 6, wherein the target site is upstream of an endogenous regulatory sequence of the targeted gene.

16. The DNA construct of claim 15, wherein the construct further comprises a second targeting sequence homologous to a sequence upstream of an endogenous regulatory sequence of the targeted gene.

17. The DNA construct of claim 6, wherein the targeted gene encodes a therapeutic protein.

18. The DNA construct of claim 6, wherein the targeted gene encodes a hormone, a cytokine, an antigen, an antibody, an enzyme, a clotting factor, a transport protein, a receptor, a regulatory protein, a structural protein, or a transcription factor.

19. The DNA construct of claim 6, wherein the targeted gene encodes a protein selected from the group consisting of calcitonin, insulin, insulinotropin, insulin-like growth factors, parathyroid hormone, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, superoxide dismutase, tissue plasminogen activator, urokinase, antithrombin III, DNase, tyrosine hydroxylase, blood clotting factor V, blood clotting factor VII, blood clotting factor VIII, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, and soluble CD4.

20. The DNA construct of claim 6, wherein the targeted gene encodes growth hormone.

21. The DNA construct of claim 6, wherein the targeted gene encodes blood clotting factor IX.

22. The DNA construct of claim 6, wherein the targeted gene encodes α-galactosidase.

23. The DNA construct of claim 6, wherein the targeted gene encodes glucocerebrosidase.

24. The DNA construct of claim 6, wherein the targeted gene encodes erythropoietin.

25. The DNA construct of claim 24, wherein the erythropoietin is human erythropoietin.

26. The DNA construct of claim 24, wherein the exon comprises coding sequence which is the same as the coding sequence of the first exon of the erythropoietin gene.

27. The DNA construct of claim 24, wherein the exon comprises coding sequence which is different from the coding sequence of the first exon of the erythropoietin gene.

28. The DNA construct of claim 24, wherein the exon comprises coding sequence which is the same as the coding sequence of the first exon of a growth hormone gene.

29. The DNA construct of claim 28, wherein the growth hormone gene encodes human growth hormone (hGH).

30. The DNA construct of claim 6, wherein the exogenous regulatory sequence is a promoter, an enhancer, a scaffold-attachment region, or a transcription factor binding site.

31. The DNA construct of claim 30, further comprising a second exogenous regulatory sequence.

32. The DNA construct of claim 30, wherein the exogenous regulatory sequence is a regulatory sequence of an adenovirus gene, a regulatory sequence of an SV-40 gene or a regulatory sequence of a cytomegalovirus gene.

33. The DNA construct of claim 30, wherein the exogenous regulatory sequence is a regulatory sequence of a mouse metallothionein-I gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

34. The DNA construct of claim 6, further comprising a gene.

35. The DNA construct of claim 6, further comprising one or more selectable marker genes.

36. The DNA construct of claim 6, further comprising an amplifiable marker gene.

37. A method of altering the expression of a targeted gene in a cell comprising the steps of:
  (a) providing a DNA construct comprising:
    (i) a targeting sequence;
    (ii) an exogenous regulatory sequence;
    (iii) an exon; and
    (iv) an unpaired splice-donor site at the 3' end of the exon,
  (b) providing a cell, the genome of which comprises
    (i) a target site homologous to the targeting sequence, and
    (ii) a targeted gene having an endogenous regulatory region;
  (c) transfecting the cell with the DNA construct, thereby producing a transfected cell;
  (d) maintaining the transfected cell under conditions appropriate for homologous recombination, thereby producing a homologously recombinant cell the genome of which comprises the exogenous regulatory sequence, the construct-derived exon, and the construct-derived splice-donor site, in addition to all endogenous exons of the targeted gene; and
  (e) maintaining the homologously recombinant cell under conditions appropriate for transcription under the control of the exogenous regulatory sequence, to produce a transcript of the construct-derived exon, the targeted gene, and any sequence lying between the construct-derived exon and the targeted gene, wherein the RNA of the transcript corresponding to the construct-derived splice-donor site directs splicing to a splice-acceptor site in the transcript which corresponds to a site within the targeted gene.

38. The method of claim 37, wherein the DNA construct is linear.

39. The method of claim 37, wherein the exon sequence does not overlap with the targeting sequence.

40. The method of claim 37, wherein the splice-acceptor site of the transcript corresponds to the splice-acceptor site of the second endogenous exon of the targeted gene.

41. The method of claim 37, further comprising the steps of:
(f) maintaining the homologously recombinant cell under conditions appropriate for splicing and translation of the transcript; and
(g) confirming that a translation product of the transcript was produced.

42. A method of altering the expression of a gene in a cell comprising the steps of:
(a) providing a cell, the genome of which comprises
(i) a targeted gene having an endogenous regulatory region;
(ii) a target site;
(b) providing a DNA construct comprising:
(i) a targeting sequence homologous to the target site;
(ii) an exogenous regulatory sequence;
(iii) an exon; and
(iv) an unpaired splice-donor site at the 3' end of the exon,
(c) transfecting the cell with the DNA construct, thereby producing a transfected cell;
(d) maintaining the transfected cell under conditions appropriate for homologous recombination, thereby producing a homologously recombinant cell the genome of which contains the exogenous regulatory sequence, the construct-derived exon, and the construct-derived splice-donor site, all upstream of the endogenous transcription initiation site of the targeted gene; and
(e) maintaining the homologously recombinant cell under conditions appropriate for transcription under the control of the exogenous regulatory sequence, to produce a transcript of the construct-derived exon, the targeted gene, and any sequence lying between the construct-derived exon and the targeted gene.

43. The method of claim 42, wherein the splice-acceptor site of the transcript corresponds to the splice-acceptor site of the second exon of the targeted gene.

44. The method of claim 42, wherein the exon comprises a CAP site.

45. The method of claim 44, wherein the exon further comprises the nucleotide sequence ATG.

46. The method of claim 42, wherein the target site is upstream of an endogenous regulatory region of the targeted gene.

47. The method of claim 42, wherein the DNA construct further comprises a second targeting sequence homologous to a sequence upstream of an endogenous regulatory sequence of the targeted gene.

48. The method of claim 42, wherein the cell is a human cell.

49. The method of claim 42, wherein the targeted gene encodes a therapeutic protein.

50. The method of claim 42, wherein the targeted gene encodes a hormone, a cytokine, an antigen, an antibody, an enzyme, a clotting factor, a transport protein, a receptor, a regulatory protein, a structural protein, or a transcription factor.

51. The method of claim 42, wherein the targeted gene encodes a protein selected from the group consisting of calcitonin, insulin, insulinotropin, insulin-like growth factors, parathyroid hormone, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, superoxide dismutase, tissue plasminogen activator, urokinase, antithrombin III, DNase, tyrosine hydroxylase, blood clotting factor V, blood clotting factor VII, blood clotting factor VIII, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, and soluble CD4.

52. The method of claim 42, wherein the targeted gene encodes growth hormone.

53. The method of claim 42, wherein the targeted gene encodes blood clotting factor IX.

54. The method of claim 42, wherein the targeted gene encodes α-galactosidase.

55. The method of claim 42, wherein the targeted gene encodes glucocerebrosidase.

56. The method of claim 42, wherein the targeted gene encodes erythropoietin.

57. The method of claim 56, wherein the erythropoietin is human erythropoietin.

58. The method of claim 56, wherein the construct-derived exon comprises coding sequence which is the same as the coding sequence of the first exon of erythropoietin.

59. The method of claim 56, wherein the construct-derived exon comprises coding sequence which is different from the coding sequence of the first exon of erythropoietin.

60. The method of claim 59, wherein the construct-derived exon comprises coding sequence that is the same as the coding sequence of the first exon of human growth hormone.

61. The method of claim 60, wherein the growth hormone is human growth hormone.

62. The method of claim 42, wherein the exogenous regulatory sequence is a promoter, an enhancer, a scaffold-attachment region, or a transcription factor binding site.

63. The method of claim 62, wherein the DNA construct further comprises a second regulatory sequence.

64. The method of claim 62, wherein the exogenous regulatory sequence is a regulatory sequence of an adenovirus gene, a regulatory sequence of an SV-40 gene, or a regulatory sequence of a cytomegalovirus gene.

65. The method of claim 62, wherein the exogenous regulatory sequence is a regulatory sequence of a mouse metallothionein-I gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

66. The method of claim 42 further comprising the steps of:
(f) maintaining the homologously recombinant cell under conditions appropriate for splicing and translation of the transcript; and
(g) confirming that a translation product of the transcript was produced.

67. The method of claim 66 in which the targeted gene encodes erythropoietin.

68. A cultured vertebrate cell the genome of which bears a transcription unit comprising an exogenous regulatory sequence, an exogenous exon, and a splice-donor site at the 3' end of the exogenous exon, the splice-donor site being operatively linked to the endogenous splice-acceptor site of the second endogenous exon of an endogenous gene, wherein the genome comprises the exogenous exon in addition to all endogenous exons of the endogenous gene.

69. The cell of claim 68, wherein the exogenous exon comprises a CAP site.

70. The cell of claim 69, wherein the exogenous exon further comprises the nucleotide sequence ATG.

71. The cell of claim 68, wherein the exogenous exon comprises a coding sequence in-frame with what prior to homologous recombination was the second exon of the endogenous gene.

72. The cell of claim 71, wherein the coding sequence of the exogenous exon encodes the same amino acid sequence as that encoded by the first exon of erythropoietin.

73. The cell of claim 71, wherein the coding sequence of the exogenous exon is different from the coding sequence of the first exon of erythropoietin.

74. The cell of claim 71, wherein the coding sequence of the exogenous exon encodes the same amino acid sequence as that encoded by the first exon of human growth hormone.

75. The cell of claim 68, wherein what prior to homologous recombination was the first endogenous exon of the endogenous gene is deleted.

76. The cell of claim 68, wherein the endogenous gene encodes a hormone, a cytokine, an antigen, an antibody, an enzyme, a clotting factor, a transport protein, a receptor, a regulatory protein, a structural protein, or a transcription factor.

77. The cell of claim 68, wherein the endogenous gene encodes a protein selected from the group consisting of calcitonin, insulin, insulinotropin, insulin-like growth factors, parathyroid hormone, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, superoxide dismutase, tissue plasminogen activator, urokinase, antithrombin III, DNase, tyrosine hydroxylase, blood clotting factor V, blood clotting factor VII, blood clotting factor VIII, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, and soluble CD4.

78. The cell of claim 68, wherein the endogenous gene encodes growth hormone.

79. The cell of claim 68, wherein the endogenous gene encodes blood clotting factor IX.

80. The cell of claim 68, wherein the endogenous gene encodes α-galactosidase.

81. The cell of claim 68, wherein the endogenous gene encodes glucocerebrosidase.

82. The cell of claim 68, wherein the endogenous gene encodes erythropoietin.

83. The cell of claim 68, wherein the coding sequence of the exogenous exon is the same as the coding sequence of the first exon of the endogenous gene.

84. The cell of claim 68, wherein the coding sequence of the exogenous exon is different from the coding sequence of the first exon of the endogenous gene.

85. The cell of claim 68, wherein the exogenous regulatory sequence, exogenous exon and splice-donor site are upstream of the coding sequence of the endogenous gene.

86. The cell of claim 68, wherein the cell expresses a therapeutic protein.

87. The cell of claim 86, wherein the cell expresses erythropoietin.

88. The cell of claim 68, wherein the cell expresses a fusion protein comprising a first amino acid sequence encoded by the exogenous exon and a second amino acid sequence encoded by a portion of the endogenous gene.

89. The cell of claim 88, wherein the endogenous gene encodes erythropoietin.

90. The cell of claim 89, wherein the fusion protein comprises amino acids 1–3 of human growth hormone signal peptide.

91. The cell of claim 89, wherein the erythropoietin is human erythropoietin.

92. The cell of claim 68, wherein the cell is a primary or secondary cell of vertebrate origin.

93. The cell of claim 92, wherein the cell is a primary or secondary mammalian cell.

94. The cell of claim 92, wherein the cell is a primary or secondary human cell.

95. The cell of claim 68, wherein the cell is an immortalized mammalian cell.

96. The cell of claim 68, wherein the cell is an immortalized human cell.

97. The cell of claim 68, wherein the cell is selected from the group consisting of: HeLa cells and derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 2426 cells, U-937 cells, Bowes Melanoma cells, WI-38VA13 subline 2R4 cells, and MOLT-4 cells.

98. The cell of claim 68, wherein the cell is an HT1080 cell.

99. The cell of claim 68, wherein the exogenous regulatory sequence is a promoter, an enhancer, a scaffold-attachment region or a transcription factor binding site.

100. The cell of claim 99, wherein the exogenous regulatory sequence is a promoter.

101. The cell of claim 99, wherein the exogenous regulatory sequence is a regulatory sequence of an adenovirus gene, a regulatory sequence of an SV-40 gene, or a regulatory sequence of a cytomegalovirus gene.

102. The cell of claim 99, wherein the exogenous regulatory sequence is a regulatory sequence of a mouse metallothionein gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

103. A cultured vertebrate cell the genome of which bears a transcription unit comprising an exogenous regulatory sequence, an exogenous exon and a splice-donor site at the 3' end of the exogenous exon, all located upstream of the transcription initiation site of an endogenous gene in a chromosome of the cell, the splice-donor site being operatively linked to the endogenous splice-acceptor site of the second endogenous exon of the endogenous gene.

104. A DNA construct which alters the expression of an targeted gene in a cell when the DNA construct is homologously recombined with a target site within the chromosomal DNA of the cell, the DNA construct comprising:

(a) a targeting sequence homologous to the target site;

(b) an exogenous regulatory sequence;

(c) an exon;

(d) a splice-donor site;
(e) an intron; and
(f) a splice-acceptor site;
wherein upon homologous recombination, (b)–(f) are present in the chromosomal DNA of the cell in addition to all exons of the targeted gene, and the exogenous regulatory sequence controls transcription of (c)–(f) as well as part or all of the targeted gene.

105. The DNA construct of claim 104, wherein the target site is upstream of an endogenous regulatory sequence of the targeted gene.

106. The DNA construct of claim 104, wherein the construct further comprises a second targeting sequence homologous to a sequence upstream of an endogenous regulatory sequence of the targeted gene.

107. The DNA construct of claim 104, wherein the targeted gene encodes a therapeutic protein.

108. The DNA construct of claim 104, wherein the targeted gene encodes a hormone, a cytokine, an antigen, an antibody, an enzyme, a clotting factor, a transport protein, a receptor, a regulatory protein, a structural protein, or a transcription factor.

109. The DNA construct of claim 104, wherein the targeted gene encodes a protein selected from the group consisting of calcitonin, insulin, insulinotropin, insulin-like growth factors, parathyroid hormone, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, glucocerebrosidase, superoxide dismutase, tissue plasminogen activator, urokinase, antithrombin III, DNase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, soluble CD4, erythropoietin, and growth hormone.

110. The DNA construct of claim 104, wherein the targeted gene encodes α-galactosidase.

111. The DNA construct of claim 104, wherein the targeted gene encodes α-interferon.

112. The DNA construct of claim 104, wherein the exogenous regulatory sequence is a promoter, an enhancer, a scaffold-attachment region, or a transcription factor binding site.

113. The DNA construct of claim 112, further comprising a second regulatory sequence.

114. The DNA construct of claim 112, wherein the exogenous regulatory sequence is a regulatory sequence of an adenovirus gene, a regulatory sequence of an SV-40 gene, or a regulatory sequence of a cytomegalovirus gene.

115. The DNA construct of claim 112, wherein the regulatory sequence is a regulatory sequence of a mouse metallothionein-I gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

116. The DNA construct of claim 104, further comprising a gene.

117. The DNA construct of claim 104, further comprising one or more selectable marker genes.

118. The DNA construct of claim 117, further comprising an amplifiable marker gene.

119. A method of altering the expression of a targeted gene in a cell, comprising the steps of:
(a) transfecting the cell with a DNA construct, the DNA construct comprising:
(i) a targeting sequence;
(ii) an exogenous regulatory sequence;
(iii) an exon;
(iv) a splice-donor site;
(v) an intron; and
(vi) a splice-acceptor site,
to generate a transfected cell;
(b) maintaining the transfected cell under conditions appropriate for homologous recombination, thereby producing a homologously recombinant cell the chromosomal DNA of which comprises the construct-derived exon and intron in addition to the endogenous coding sequence of the targeted gene; and
(c) maintaining the homologously recombinant cell under conditions appropriate for transcription of (iii)–(vi) and the targeted gene under the control of the exogenous regulatory sequence, thereby producing a transcript.

120. The method of claim 119, wherein the size of the intron is selected to maximize expression of the targeted gene under the control of the exogenous regulatory sequence.

121. The method of claim 119, wherein the exon comprises a CAP site.

122. The method of claim 121, wherein the exon comprises the nucleotide sequence ATG.

123. A fusion protein produced by the method of claim 122 and containing a first amino acid sequence encoded by the construct-derived exon and a second amino acid sequence encoded by the entire targeted gene.

124. The method of claim 119, wherein the targeting sequence is homologous to a sequence upstream of an endogenous regulatory sequence of the targeted gene.

125. The method of claim 119, wherein the construct further comprises a second targeting sequence homologous to a sequence upstream of an endogenous regulatory sequence of the targeted gene.

126. The method of claim 119, wherein the cell is a human cell.

127. The method of claim 119, wherein the targeted gene encodes a therapeutic protein.

128. The method of claim 119, wherein the targeted gene encodes a hormone, a cytokine, an antigen, an antibody, an enzyme, a clotting factor, a transport protein, a receptor, a regulatory protein, a structural protein, or a transcription factor.

129. The method of claim 119, wherein the targeted gene encodes a protein selected from the group consisting of calcitonin, insulin, insulinotropin, insulin-like growth factors, parathyroid hormone, β-interferon, γ-interferon, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, glucocerebrosidase, superoxide dismutase, tissue plasminogen activator, urokinase, antithrombin III, DNase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, a globin, low density lipoprotein receptor, IL-2 receptor, IL-2 receptor antagonists, alpha-1 antitrypsin, immune response modifiers, soluble CD4, erythropoietin, and growth hormone.

130. The method of claim 119, wherein the targeted gene encodes α-galactosidase.

131. The method of claim 119, wherein the targeted gene encodes α-interferon.

132. The method of claim 119, wherein the exogenous regulatory sequence is a promoter, an enhancer, a scaffold-attachment region, or a transcription factor binding site.

133. The method of claim 132, wherein the construct further comprises a second regulatory sequence.

134. The method of claim 132, wherein the exogenous regulatory sequence is a regulatory sequence of an adenovirus gene, a regulatory sequence of an SV-40 gene, or a regulatory sequence of a cytomegalovirus gene.

135. The method of claim 132, wherein the exogenous regulatory sequence is a regulatory sequence of a mouse metallothionein-I gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

136. The method of claim 119, further comprising the steps of:
   (f) maintaining the homologously recombinant cell under conditions appropriate for splicing and translation of the transcript; and
   (g) confirming that a translation product of the transcript was produced.

137. The method of claim 136 in which the targeted gene encodes α-interferon.

138. The method of claim 136 in which the targeted gene encodes α-galactosidase.

139. A cultured vertebrate cell having incorporated therein a transcription unit comprising an exogenous regulatory sequence, an exogenous exon, a splice-donor site, an intron, and a splice-acceptor site, wherein the exogenous regulatory sequence is positioned to control transcription of the exogenous exon, splice-donor site, intron, and splice-acceptor site, in addition to all endogenous exons of an endogenous gene.

140. The cell of claim 139, wherein the exogenous exon comprises a CAP site.

141. The cell of claim 139, wherein the exogenous regulatory sequence, exogenous exon and splice-donor site are upstream of the coding sequence of the endogenous gene.

142. The cell of claim 139, wherein an endogenous regulatory sequence of the endogenous gene is deleted.

143. The cell of claim 139, wherein the first endogenous exon of the endogenous gene is deleted.

144. The cell of claim 139, wherein the endogenous gene encodes a hormone, a cytokine, an antigen, an antibody, an enzyme, a clotting factor, a transport protein, a receptor, a regulatory protein, a structural protein, or a transcription factor.

145. The cell of claim 139, wherein the endogenous gene encodes a protein selected from the group consisting of erythropoietin, calcitonin, growth hormone, insulin, insulinotropin, an insulin-like growth factor, parathyroid hormone, β-interferon, γ-interferon, nerve growth factors, FSHβ, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-granulocyte, CSF-macrophage, CSF-granulocyte/macrophage, immunoglobulins, catalytic antibodies, protein kinase C, glucocerebrosidase, superoxide dismutase, tissue plasminogen activator, urokinase, antithrombin III, DNase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, soluble CD4, growth hormone, and erythropoietin.

146. The cell of claim 139, wherein the endogenous gene encodes α-interferon.

147. The cell of claim 139, wherein the endogenous gene encodes α-galactosidase.

148. The cell of claim 139, wherein the cell is a primary or secondary cell of vertebrate origin.

149. The cell of claim 148, wherein the cell is a primary or secondary mammalian cell.

150. The cell of claim 148, wherein the cell is a primary or secondary human cell.

151. The cell of claim 148, wherein the cell is an immortalized mammalian cell.

152. The cell of claim 148, wherein the cell is an immortalized human cell.

153. The cell of claim 139, wherein the cell is selected from the group consisting of: HeLa cells and derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 2426 cells, U-937 cells, Bowes Melanoma cells, WI-38VA13 subline 2R4 cells, and MOLT-4 cells.

154. The cell of claim 139, wherein the cell is an HT1080 cell.

155. The cell of claim 139, wherein the cell expresses a therapeutic protein.

156. The cell of claim 139, wherein the cell expresses α-interferon.

157. The cell of claim 139, wherein the cell expresses α-galactosidase.

158. The cell of claim 139, wherein the exogenous regulatory sequence is a promoter, an enhancer, a scaffold-attachment region, or a transcription factor binding site.

159. The cell of claim 158, wherein the exogenous regulatory sequence is a promoter.

160. The cell of claim 158, wherein the exogenous regulatory sequence is a regulatory sequence of an adenovirus gene, a regulatory sequence of an SV-40 gene, or a regulatory sequence of a cytomegalovirus gene.

161. The cell of claim 158, wherein the exogenous regulatory sequence is a regulatory sequence of a mouse metallothionein gene, a regulatory sequence of a collagen gene, a regulatory sequence of an actin gene, a regulatory sequence of an immunoglobulin gene, a regulatory sequence of an HMG-CoA reductase gene, or a regulatory sequence of an EF-1α gene.

162. The method of making a homologously recombinant cell wherein the expression of a targeted gene is altered, comprising the steps of:
   (a) transfecting a cell with a DNA construct, the construct comprising:
      (i) a targeting sequence homologous to a target site in the chromosomal DNA of the cell;
      (ii) an exogenous regulatory sequence;
      (iii) an exon;
      (iv) a splice-donor site;
      (v) an intron; and
      (vi) a splice-acceptor site,
      to generate a transfected cell; and
   (b) maintaining the transfected cell under conditions appropriate for homologous recombination, thereby producing a homologously recombinant cell the chromosomal DNA of which comprises the construct-derived exon and intron in addition to the endogenous sequence of the targeted gene, wherein the exogenous regulatory sequence controls expression of a transcript comprising RNA corresponding to (iii)–(vi) and part or all of the targeted gene.

163. A homologously recombinant cell produced by the method of claim 162.

164. A method of altering the expression of a targeted gene in a cell, comprising the steps of:
(a) transfecting a cell with a DNA construct, the construct comprising:
(i) a targeting sequence;
(ii) an exogenous regulatory sequence;
(iii) an exon;
(iv) a splice-donor site;
(v) an intron; and
(vi) a splice-acceptor site,
thereby producing a transfected cell, wherein the targeting sequence directs the integration of elements (ii)–(vi) into genomic DNA of the cell such that the regulatory sequence is positioned to direct transcription of a sequence comprising (iii)–(vi) and sequence of the targeted gene;
(b) maintaining the transfected cell under conditions appropriate for homologous recombination, thereby producing a homologously recombinant cell; and
(c) maintaining the homologously recombinant cell under conditions appropriate for expression under the control of the regulatory sequence.

165. A method for expressing an erythropoietin gene in the genome of a mammalian cell, comprising transfecting the cell with a construct comprising
(a) a targeting sequence,
(b) an exogenous regulatory sequence,
(c) an exon; and
(d) an unpaired splice-donor site at the 3' end of the exon, wherein the targeting sequence directs the integration of (b)–(d) into the chromosomal DNA of the cell upstream and within 30 kb of the endogenous ATG initiation codon of the erythropoietin gene such that the exogenous regulatory sequence directs expression of a transcript comprising sequence corresponding to the construct-derived exon and all endogenous exons of the erythropoietin gene.

166. The method of claim 165, wherein the targeting sequence is homologous to a sequence located between about 5 kilobases and about 30 kilobases upstream of the ATG initiation codon of the erythropoietin gene.

167. The method of claim 165, wherein the mammalian cell is a human cell.

168. A cultured vertebrate cell which expresses erythropoietin, the genome of said cell having incorporated therein a transcription unit comprising an exogenous regulatory region, an exogenous exon, and an exogenous splice-donor site, wherein transcription under the control of the exogenous regulatory region produces a transcript comprising RNA corresponding to the exogenous exon, the exogenous splice-donor site, and all endogenous exons of an endogenous erythropoietin gene, wherein the RNA corresponding to the splice-donor site directs splicing to a splice-acceptor site of the transcript which corresponds to a site within the endogenous erythropoietin gene.

169. The cultured vertebrate cell of claim 168, wherein the splice-acceptor site of the transcript corresponds to the splice-acceptor site of the second exon of the erythropoietin gene.

170. A cultured vertebrate cell comprising the dhfr gene, the neo gene, the CMV immediate early promoter, intron 1 of the CMV immediate early gene, hGH exon 1 and an unpaired splice-donor site inserted at a position upstream of the ATG initiation codon of an endogenous erythropoietin gene, such that after transcription driven by the CMV promoter, the hGH exon 1 portion of the transcript is spliced to the portion of the transcript transcribed from exon 2 of the erythropoietin gene.

171. The cultured vertebrate cell of claim 170 produced by the integration of DNA from pREPO18.

172. A DNA construct which alters expression of an endogenous GM-CSF (colony stimulating factor-granulocyte/macrophage) gene in a cell when the DNA construct is homologously recombined with a target site within or upstream of a GM-CSF gene in the chromosomal DNA of the cell, the construct comprising:
(a) a targeting sequence homologous with the target site;
(b) an exogenous regulatory sequence;
(c) an exon; and
(d) an unpaired splice-donor site at the 3' end of the exon; wherein following homologous recombination of the targeting sequence with the target site, the exogenous regulatory sequence controls expression of a transcript comprising RNA corresponding to the construct-derived exon in addition to all endogenous exons of the GM-CSF gene.

173. The DNA construct of claim 172, wherein (a)–(d) are oriented such that, upon integration of the construct into chromosomal DNA of the cell at the target site, (b)–(d) are integrated upstream of exon 1 of the endogenous GM-CSF gene, and a transcript produced under the control of the exogenous regulatory sequence of (b) contains a splice-donor site
(i) that corresponds to the splice-donor site of (d), and
(ii) is spliced to an endogenous splice-acceptor site of the second endogenous exon of the GM-CSF gene.

174. The DNA construct of claim 173, wherein the construct-derived exon of the transcript comprises coding sequence which, upon splicing of the construct-derived splice-donor site of the transcript with the endogenous splice-acceptor site of the transcript, is in-frame with the RNA corresponding to the coding sequence of the GM-CSF gene.

175. The DNA construct of claim 174, wherein the coding sequence of the construct-derived exon encodes the same amino acid sequence as encoded by the first endogenous exon of the GM-CSF gene.

176. The DNA construct of claim 174, wherein the coding sequence of the construct-derived exon is different from the coding sequence of the first endogenous exon of the GM-CSF gene.

177. The DNA construct of claim 172, wherein the exogenous regulatory sequence comprises a promoter.

178. The DNA construct of claim 172, further comprising a DNA sequence encoding a selectable marker.

179. The DNA construct of claim 172, further comprising an amplifiable marker gene.

180. The DNA construct of claim 172, wherein the construct-derived exon comprises a CAP site.

181. The DNA construct of claim 180, wherein the construct-derived exon further comprises the nucleotide sequence ATG.

182. The DNA construct of claim 172, wherein the targeting sequence is homologous to a sequence within the GM-CSF gene.

183. The DNA construct of claim 172, wherein the targeting sequence is homologous to a sequence upstream of the coding region of the GM-CSF gene.

184. The DNA construct of claim 172, wherein the targeting sequence is homologous to a sequence upstream of an endogenous regulatory region of the GM-CSF gene.

185. The DNA construct of claim 172, further comprising a second targeting sequence homologous to a second target site within or upstream of the endogenous GM-CSF coding sequence.

186. The DNA construct of claim 172, wherein the construct-derived exon encodes the first 50 amino acids of the GM-CSF precursor protein.

187. The DNA construct of claim 172, wherein the construct-derived exon encodes a sequence comprising a functional signal peptide.

188. A method of producing a homologously recombinant cell wherein the expression of a GM-CSF gene is altered, comprising the steps of:
   (a) providing a cell, the genome of which contains an endogenous GM-CSF gene;
   (b) transfecting the cell with a DNA construct, the construct comprising
      (i) a targeting sequence homologous with a target site within or upstream of the endogenous GM-CSF gene;
      (ii) an exogenous regulatory sequence;
      (iii) an exon; and
      (iv) an unpaired splice-donor site at the 3' end of the exon,
      thereby producing a transfected cell; and
   (c) maintaining the transfected cell under conditions appropriate for homologous recombination, thereby producing a homologously recombinant cell in which the exogenous regulatory sequence controls expression of a transcript comprising RNA corresponding to the construct-derived exon, the construct-derived splice-donor site, and all endogenous exons of the GM-CSF gene.

189. The method of claim 188, wherein the cell is of vertebrate origin.

190. The method of claim 189, wherein the cell is a primary or secondary mammalian cell.

191. The method of claim 189, wherein the cell is a primary or secondary human cell.

192. The method of claim 189, wherein the cell is an immortalized mammalian cell.

193. The method of claim 189, wherein the cell is an immortalized human cell.

194. The method of claim 188, wherein the cell is selected from the group consisting of: HeLa cells and derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 2426 cells, U-937 cells, Bowes Melanoma cells, WI-38VA13 subline 2R4 cells, and MOLT-4 cells.

195. The method of claim 188, wherein the cell is an HT1080 cell.

196. A homologously recombinant cell produced by the method of claim 188.

197. The cell of claim 68, wherein the exogenous regulatory sequence, exogenous exon and splice-donor site are upstream of an endogenous regulatory sequence of the endogenous gene.

198. The cell of claim 68, wherein what prior to homologous recombination was an endogenous regulatory sequence of the endogenous gene is deleted.

199. A method for producing GM-CSF, comprising the steps of:
   (a) transfecting a cell, the chromosomal DNA of which contains an endogenous GM-CSF gene, with a DNA construct comprising
      (i) a targeting sequence homologous with a target site within or upstream of the endogenous GM-CSF gene;
      (ii) an exogenous regulatory sequence;
      (iii) an exon; and
      (iv) an unpaired splice-donor site at the 3' end of the exon,
      thereby producing a transfected cell;
   (b) maintaining the transfected cell under conditions appropriate for homologous recombination to occur, thereby producing a homologously recombinant cell in the genomic DNA of which (a)(ii)–(iv) are positioned upstream of the endogenous transcription initiation site of the GM-CSF gene, and the exogenous regulatory sequence controls expression of a transcript comprising RNA corresponding to (a)(iii)–(iv) and the GM-CSF gene; and
   (c) maintaining the homologously recombinant cell produced in step (b) under conditions appropriate for the production of GM-CSF under the control of the exogenous regulatory sequence.

200. A DNA construct which alters the expression of an endogenous G-CSF (colony stimulating factor-granulocyte) gene in a cell when the DNA construct is homologously recombined with a target site within or upstream of the coding region of the G-CSF gene in the chromosomal DNA of the cell, said construct comprising:
   (a) a targeting sequence homologous with the target site;
   (b) an exogenous regulatory sequence;
   (c) an exon; and
   (d) an unpaired splice-donor site at the 3' end of the exon;
wherein following homologous recombination of the targeting sequence with the target site, the exogenous regulatory sequence controls expression of a transcript comprising RNA corresponding to the construct-derived exon in addition to all endogenous exons of the G-CSF gene.

201. The DNA construct of claim 200, wherein (a)–(d) are oriented such that, upon integration of the construct into chromosomal DNA of the cell at the target site, (b)–(d) are integrated upstream of exon 1 of the endogenous G-CSF gene and the transcript contains a splice-donor site that
   (i) corresponds to the splice-donor site of (d), and
   (ii) is spliced to an endogenous splice-acceptor site of the second endogenous exon of the G-CSF gene.

202. The DNA construct of claim 201, wherein the construct-derived exon of the transcript comprises coding sequence which, upon splicing of the construct-derived splice-donor site of the transcript with the endogenous splice-acceptor site of the transcript, is in-frame with RNA corresponding to the coding sequence of the G-CSF gene.

203. The DNA construct of claim 202, wherein the coding sequence of the construct-derived exon encodes the same amino acid sequence as that encoded by the coding sequence of the first endogenous exon of the G-CSF gene.

204. The DNA construct of claim 202, wherein the coding sequence of the construct-derived exon is different from the coding sequence of the first endogenous exon of the G-CSF gene.

205. The DNA construct of claim 200, wherein the exogenous regulatory sequence comprises a promoter.

206. The DNA construct of claim 200, further comprising a selectable marker gene.

207. The DNA construct of claim 206, further comprising an amplifiable marker gene.

208. The DNA construct of claim 200, wherein the construct-derived exon comprises a CAP site.

209. The DNA construct of claim 208, wherein the construct-derived exon further comprises the nucleotide sequence ATG.

210. The DNA construct of claim 200, wherein the target site is within the coding region of the G-CSF gene.

211. The DNA construct of claim 200 wherein the target site is upstream of the coding region of the G-CSF gene.

212. The DNA construct of claim 200, wherein the target site is upstream of an endogenous regulatory region of the G-CSF gene.

213. The DNA construct of claim 200 further comprising a second targeting sequence homologous to a second target site within or upstream of the endogenous G-CSF coding sequence.

214. The DNA construct of claim 200 wherein the construct-derived exon encodes an amino acid sequence which is identical to the first 13 amino acid residues of the G-CSF signal peptide.

215. The DNA construct of claim 200, wherein the construct-derived exon encodes an amino acid sequence which is functionally equivalent to the first 13 amino acids of the G-CSF signal peptide.

216. A method of producing a homologously recombinant cell wherein the expression of a G-CSF gene is altered, comprising the steps of:
(a) providing a cell, the genome of which contains an endogenous G-CSF gene;
(b) transfecting the cell with a DNA construct comprising
  (i) a targeting sequence homologous with a target site within or upstream of the endogenous G-CSF gene;
  (ii) an exogenous regulatory sequence;
  (iii) an exon; and
  (iv) an unpaired splice-donor site at the 3' end of the exon,
thereby producing a transfected cell; and
(c) maintaining the transfected cell under conditions appropriate for homologous recombination, thereby producing a homologously recombinant cell in which the exogenous regulatory sequence controls expression of a transcript comprising RNA corresponding to the construct-derived exon, construct-derived splice-donor site, and all endogenous exons of the G-CSF gene.

217. The method of claim 216, wherein the cell is of vertebrate origin.

218. The method of claim 217, wherein the cell is a primary or secondary mammalian cell.

219. The method of claim 217, wherein the cell is a primary or secondary human cell.

220. The method of claim 217, wherein the cell is an immortalized mammalian cell.

221. The method of claim 217, wherein the cell is an immortalized human cell.

222. The method of claim 216, wherein the cell is selected from the group consisting of: HeLa cells and derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 2426 cells, U-937 cells, Bowes Melanoma cells, WI-38VA13 subline 2R4 cells, and MOLT-4 cells.

223. The method of claim 216, wherein the cell is an HT1080 cell.

224. A homologously recombinant cell produced by the method of claim 216.

225. A cultured vertebrate cell which expresses G-CSF, the genome of the cell having incorporated therein a transcription unit comprising an exogenous regulatory region, an exogenous exon, and an exogenous splice-donor site at the 3' end of the exogenous exon, wherein transcription under the control of the exogenous regulatory region produces a transcript comprising RNA corresponding to the exogenous exon, the exogenous splice-donor site, and all of the endogenous exons of an endogenous G-CSF gene, wherein the RNA corresponding to the splice-donor site directs splicing to a splice-acceptor site of the transcript which corresponds to a site within the endogenous G-CSF gene.

226. The cell of claim 225, wherein the exogenous splice-donor site is operatively linked to the endogenous splice-acceptor site of the second exon of the G-CSF gene.

227. A method for producing G-CSF, comprising the steps of:
(a) transfecting a cell, the chromosomal DNA of which contains an endogenous G-CSF gene, with a DNA construct comprising,
  (i) a targeting sequence homologous with a target site within or upstream of the endogenous G-CSF gene;
  (ii) an exogenous regulatory sequence;
  (iii) an exon; and
  (iv) an unpaired splice-donor site at the 3' end of the exon,
thereby producing a transfected cell;
(b) maintaining the transfected cell under conditions appropriate for homologous recombination, thereby producing a homologously recombinant cell in the genomic DNA of which (a)(ii)–(iv) are positioned upstream of the endogenous transcription initiation site of the G-CSF gene, and the exogenous regulatory sequence controls expression of a transcript comprising RNA corresponding to (a)(iii)–(iv) and the G-CSF gene; and
(c) maintaining the homologously recombinant cell produced in step (b) under conditions appropriate for the production of G-CSF under the control of the exogenous regulatory sequence.

228. A DNA construct which alters the expression of an FSHβ (follicle stimulating hormone-β) gene in a cell when the DNA construct is homologously recombined with a target site within or upstream of an FSHβ gene in the chromosomal DNA of the cell, the construct comprising:
(a) a targeting sequence homologous with the target site;
(b) an exogenous regulatory sequence;
(c) an exon; and
(d) an unpaired splice-donor site at the 3' end of the exon, wherein following homologous recombination of the targeting sequence with the target site, the exogenous regulatory sequence controls expression of a transcript comprising RNA corresponding to the construct-derived exon in addition to all endogenous exons of the FSHβ gene.

229. The DNA construct of claim 228, wherein (a)–(d) are oriented such that, upon integration of the construct into chromosomal DNA of the cell at the target site, (b)–(d) are integrated within or upstream of intron 1 of the endogenous FSHβ gene, and a transcript produced under the control of the exogenous regulatory sequence of (b) contains a splice-donor site
(i) that corresponds to the splice-donor site of (d), and
(ii) is spliced to an endogenous splice-acceptor site of the second endogenous exon of the FSHβ gene.

230. The DNA construct of claim 229, wherein the exogenous regulatory sequence comprises a promoter.

231. The DNA construct of claim 229, further comprises a selectable marker gene.

232. The DNA construct of claim 229, further comprising an amplifiable marker gene.

233. The DNA construct of claim 229, wherein the exon comprises a CAP site.

234. The DNA construct of claim 229, wherein the construct-derived exon is the same as the first exon of the FSHβ gene.

235. The DNA construct of claim 229, wherein the construct-derived exon is different from the first exon of the FSHβ gene.

236. The DNA construct of claim 229, wherein the target site is upstream of an endogenous regulatory region of the FSHβ gene.

237. The DNA construct of claim 229, further comprising a second targeting sequence homologous to a second target site within or upstream of the endogenous FSHβ gene.

238. A DNA construct which alters the expression of an FSHβ (follicle stimulating hormone-β) gene in a cell when the DNA construct is homologously recombined with a target site within or upstream of the first intron of an FSHβ gene in the chromosomal DNA of the cell, the construct comprising:
(a) a targeting sequence homologous with the target site;
(b) an exogenous regulatory sequence;
(c) an exon; and
(d) an unpaired splice-donor site at the 3' end of the exon, wherein following homologous recombination of the targeting sequence with the target site, the exogenous regulatory sequence controls expression of a transcript comprising RNA corresponding to the construct-derived exon in addition to all endogenous exons of the FSHβ gene.

239. A method of producing a homologously recombinant cell wherein the expression of an FSHβ gene is altered, comprising the steps of:
(a) providing a cell, the genome of which contains an endogenous FSHβ gene;
(b) transfecting the cell with a DNA construct comprising,
(i) a targeting sequence homologous with a target site within or upstream of the endogenous FSHβ gene;
(ii) an exogenous regulatory sequence;
(iii) an exon; and
(iv) an unpaired splice-donor site at the 3' end of the exon,
thereby producing a transfected cell; and
(c) maintaining the transfected cell under conditions appropriate for homologous recombination, thereby producing a homologously recombinant cell in which the exogenous regulatory sequence controls expression of a transcript comprising RNA corresponding to the construct-derived exon, the construct-derived splice-donor site, and all of the endogenous exons of the FSHβ gene.

240. The method of claim 239, wherein the cell is of vertebrate origin.

241. The method of claim 240, wherein the cell is a primary or secondary mammalian cell.

242. The method of claim 240, wherein the cell is a primary or secondary human cell.

243. The method of claim 240, wherein the cell is an immortalized mammalian cell.

244. The method of claim 240, wherein the cell is an immortalized human cell.

245. The method of claim 244, wherein the cell is selected from the group consisting of: HeLa cells and derivatives of HeLa cells, MCF-7 breast cancer cells, K-562 leukemia cells, KB carcinoma cells, 2780AD ovarian carcinoma cells, Raji cells, Jurkat cells, Namalwa cells, HL-60 cells, Daudi cells, RPMI 2426 cells, U-937 cells, Bowes Melanoma cells, WI-38VA13 subline 2R4 cells, and MOLT-4 cells.

246. The method of claim 244, wherein the cell is an HT1080 cell.

247. A homologously recombinant cell produced by the method of claim 239.

248. An isolated DNA molecule comprising a sequence selected from the group consisting of SEQ ID NO:3 and a fragment of SEQ ID NO:3 which selectively promotes homologous recombination with genomic DNA upstream of a thrombopoietin gene.

249. A method for producing FSHβ, comprising the steps of:
(a) transfecting a cell, the chromosomal DNA of which contains an endogenous FSHβ gene, with a DNA construct comprising
(i) a targeting sequence homologous with a target site within or upstream of the endogenous FSHβ gene;
(ii) an exogenous regulatory sequence;
(iii) an exon; and
(iv) an unpaired splice-donor site at the 3' end of the exon,
thereby producing a transfected cell;
(b) maintaining the transfected cell under conditions appropriate for homologous recombination, thereby producing a homologously recombinant cell in the genomic DNA of which (a)(ii)–(iv) are positioned upstream of the endogenous transcription initiation site of the FSHβ gene, and the exogenous regulatory sequence controls expression of a transcript comprising RNA corresponding to (a)(iii)–(iv) and the FSHβ gene; and
(c) maintaining the homologously recombinant cell produced in step (b) under conditions appropriate for the production of FSHβ under the control of the exogenous regulatory sequence.

250. The method of claim 249, wherein the cell as obtained expresses human glycoprotein α-subunit.

251. The method of claim 249, wherein the cell expresses an human glycoprotein α-subunit gene under the control of an exogenous promoter.

252. A DNA construct which alters the expression of a gene encoding thrombopoietin when inserted by homologous recombination into chromosomal DNA of a cell, said construct comprising:
(a) a targeting sequence homologous with a target site upstream of the endogenous thrombopoietin gene;
(b) a regulatory sequence;
(c) a non-coding exon; and
(d) an unpaired splice-donor site at the 3' end of the exon, wherein, following homologous recombination of the targeting sequence with the target site, exogenous regulatory sequence controls expression of a transcript comprising RNA corresponding to the construct-derived exon in addition to all endogenous exons of the thrombopoietin gene.

253. The DNA construct of claim 252, wherein the regulatory sequence comprises a promoter.

254. The DNA construct of claim 252, further comprising a selectable marker gene.

255. The DNA construct of claim 252, further comprising an amplifiable marker gene.

256. The DNA construct of claim 252, further comprising a second targeting sequence comprising DNA which selectively promotes homologous recombination with genomic DNA upstream of the thrombopoietin gene.

257. The DNA construct of claim 252 wherein the targeting sequence is selected from the group consisting of SEQ ID NO:3, SEQ ID NO:4, fragments of SEQ ID NO:3 which selectively promote homologous recombination with genomic DNA upstream of the thrombopoietin gene and fragments of SEQ ID NO:4 which selectively promote homologous recombination with genomic DNA upstream of the thrombopoietin gene.

258. The DNA construct of claim 257 wherein the targeting sequence is fragment of SEQ ID NO:3 and is at least about 20 nucleotides.

259. The DNA construct of claim 257 wherein the targeting sequence is a fragment of SEQ ID NO:4 and is at least about 20 nucleotides.

260. The DNA construct of claim 257 wherein the targeting sequence is at least about 20 nucleotides and is a sequence between about nucleotides −1815 to −145, 14 to 245, or 374 to 570 of FIG. 5 (SEQ ID NO:4).

261. A method for producing thrombopoietin, comprising the steps of:
   (a) transfecting a cell containing the thrombopoietin gene with the DNA construct of claim 252;
   (b) maintaining the transfected cell under conditions appropriate for homologous recombination to occur; and
   (c) maintaining the homologously recombinant cell produced in step (b) under conditions appropriate for the expression of thrombopoietin under the control of the exogenous regulatory sequence.

262. An isolated DNA molecule comprising a sequence which is selected from the group consisting of about nucleotides −1815 to −145 of FIG. 5 (SEQ ID NO:4), about nucleotides 14 to 245 of FIG. 5 (SEQ ID NO:4), and about nucleotides 374 to 570 of FIG. 5 (SEQ ID NO:4), and which selectively promotes homologous recombination with genomic DNA within or upstream of a thrombopoietin gene.

263. A DNA construct which alters the expression of a gene encoding thrombopoietin when inserted by homologous recombination into chromosomal DNA of the cell, said construct comprising:
   (a) a targeting sequence homologous with a target site within or upstream of the endogenous thrombopoietin coding region;
   (b) a regulatory sequence;
   (c) a non-coding exon; and
   (d) an unpaired splice-donor site at the 3' end of the exon, wherein, following homologous recombination of the targeting sequence with the target site, the regulatory sequence of (b), the non-coding exon of (c), and the unpaired splice-donor site of (d) are integrated upstream of the first exon of the thrombopoietin gene and upon expression under the control of the regulatory sequence, a transcript is produced in which sequence corresponding to the construct-derived splice-donor site is spliced to sequence corresponding to the splice-acceptor site of the second endogenous exon of the thrombopoietin gene.

264. The DNA construct of claim 263, further comprising a selectable marker gene.

265. The DNA construct of claim 263, further comprising an amplifiable marker gene.

266. The DNA construct of claim 263, further comprising a second targeting sequence comprising DNA which selectively promotes homologous recombination with genomic DNA upstream of the thrombopoietin gene.

267. The DNA construct of claim 263, wherein the targeting sequence is selected from the group consisting of SEQ ID NO:3, SEQ ID NO:4, fragments of SEQ ID NO:3 which selectively promote homologous recombination with genomic DNA upstream of the thrombopoietin gene and fragments of SEQ ID NO:4 which selectively promote homologous recombination with genomic DNA upstream of the thrombopoietin gene.

268. The DNA construct of claim 267, wherein the targeting sequence is a fragment of SEQ ID NO:4 and is at least about 30 nucleotides.

269. A method of producing a homologously recombinant cell wherein the expression of a thrombopoietin gene is altered, comprising the steps of:
   (a) transfecting a cell containing the thrombopoietin gene with a DNA construct comprising
      (i) a targeting sequence homologous with a target site within or upstream of the thrombopoietin gene;
      (ii) an exogenous regulatory sequence;
      (iii) a non-coding exon; and
      (iv) an unpaired splice-donor site at the 3' end of the exon,
   thereby producing a transfected cell, and
   (b) maintaining the transfected cell under conditions appropriate for homologous recombination, thereby producing a homologously recombinant cell in which the exogenous regulatory sequence controls expression of a transcript comprising the construct-derived exon, the construct-derived splice-donor site, and all endogenous exons of the thrombopoietin gene.

270. A homologously recombinant cell produced by the method of claim 269.

271. A cultured vertebrate cell which expresses thrombopoietin, said cell having incorporated therein a transcription unit which comprises an exogenous regulatory sequence, an exogenous non-coding exon, and an exogenous splice-donor site, the splice-donor site being operatively linked to the endogenous splice-acceptor site of the second endogenous exon of he thrombopoietin gene, wherein the cell comprises the exogenous non-coding exon in addition to all endogenous exons of the thrombopoietin gene.

272. The cell of claim 271, wherein the exogenous splice-donor site is operatively linked to the endogenous splice-acceptor site of the second exon of the thrombopoietin gene.

273. A method for producing thrombopoietin comprising maintaining the cell of claim 271 under conditions appropriate for the expression of thrombopoietin under the control of the exogenous regulatory sequence.

274. A DNA construct which alters the expression of a gene encoding DNase I when inserted by homologous recombination into chromosomal DNA of the cell, said construct comprising:
   (a) a targeting sequence homologous with a target site within or upstream of the DNase I gene;
   (b) an exogenous regulatory sequence;
   (c) an exon; and
   (d) an unpaired splice-donor site at the 3' end of the exon, wherein following homologous recombination of the targeting sequence with the target site, the exogenous regulatory sequence controls expression of a transcript comprising RNA corresponding to the construct-derived exon in addition to all endogenous exons of the DNase I gene.

275. The DNA construct of claim 274, wherein the regulatory sequence comprises a promoter.

276. The DNA construct of claim 274, further comprising a selectable marker gene.

277. The DNA construct of claim 274, further comprising an amplifiable marker gene.

278. The DNA construct of claim 274, further comprising a second targeting sequence comprising DNA which hybridizes to genomic DNA within or upstream of the DNase I gene.

279. The DNA construct of claim 274 wherein the targeting sequence is selected from the group consisting of SEQ ID NO:17, SEQ ID NO: 18, fragments of SEQ ID NO:17 which selectively promote homologous recombination with genomic DNA upstream of the DNase I gene and fragments of SEQ ID NO:18 which selectively promote homologous recombination with genomic DNA within or upstream of the DNase I gene.

280. The DNA construct of claim 279 wherein the targeting sequence is a fragment of SEQ ID NO:17 and is at least about 20 nucleotides.

281. The DNA construct of claim 279 wherein the targeting sequence is a fragment of SEQ ID NO:18 and is at least about 20 nucleotides.

282. The DNA construct of claim 279 wherein the targeting sequence is at least about 20 base pairs and is a sequence between about nucleotides −328 to −2 of FIG. 11 (SEQ ID NO:18).

283. An isolated DNA molecule comprising a sequence selected from the group consisting of SEQ ID NO:17 and a fragment of SEQ ID NO:17 which selectively promotes homologous recombination with genomic DNA upstream of a DNase I gene.

284. An isolated DNA molecule of at least about 20 nucleotides which selectively promotes homologous recombination with genomic DNA within or upstream of the DNase I gene, the DNA molecule comprising a sequence selected from the group consisting of a sequence between about nucleotides −328 to −2 of FIG. 11 (SEQ ID NO:18) and a sequence which hybridizes to a sequence between about nucleotides −328 to −2 of FIG. 11 (SEQ ID NO:18).

285. A method of producing a homologously recombinant cell wherein the expression of a DNase I gene is altered, comprising the steps of:
 (a) transfecting a cell containing the DNase I gene with a DNA construct comprising
  (i) a targeting sequence homologous with a target site within or upstream of the DNase I gene;
  (ii) an exogenous regulatory sequence;
  (iii) an exon; and
  (iv) an unpaired splice-donor site at the 3' end of the exon; and
 (b) maintaining the transfected cell under conditions appropriate for homologous recombination, thereby producing a homologously recombinant cell in which the exogenous regulatory sequence controls expression of a transcript comprising the construct-derived exon, the construct-derived splice-donor site, and all of the endogenous exons of the DNase I gene.

286. A homologously recombinant cell produced by the method of claim 285.

287. A cultured vertebrate cell which expresses DNase I, the genome of the cell having incorporated therein a transcription unit comprising an exogenous regulatory region, an exogenous exon, and an exogenous splice-donor site at the 3' end of the exogenous exon, wherein transcription under the control of the exogenous regulatory region produces a transcript comprising RNA corresponding to the exogenous exon, the exogenous splice-donor site, and all of the endogenous exons of an endogenous DNase I gene, wherein the RNA corresponding to the splice-donor site directs splicing to a splice-acceptor site of the transcript which corresponds to a site within the endogenous DNase I gene.

288. The cell of claim 287, wherein the splice-acceptor site of transcript corresponds to the splice-acceptor site of the second exon of the DNase I gene.

289. A method for producing DNase I comprising maintaining the cell of claim 289 under conditions appropriate for the production of DNase I under the control of the exogenous regulatory region.

290. A method for producing DNase I, comprising the steps of:
 (a) transfecting a cell, the chromosomal DNA of which contains an endogenous DNase I gene, with a DNA construct comprising
  (i) a targeting sequence homologous with a target site within or upstream of the DNase I gene;
  (ii) an exogenous regulatory sequence;
  (iii) an exon; and
  (iv) an unpaired splice-donor site at the 3' end of the exon,
  thereby creating a transfected cell;
 (b) maintaining the transfected cell under conditions appropriate for homologous recombination, thereby producing a homologously recombinant cell in the genomic DNA of which (a)(ii)–(iv) are positioned upstream of the endogenous transcription initiation site of the DNase I gene, and the exogenous regulatory sequence controls expression of a transcript comprising RNA corresponding to (a)(iii)–(iv) and all of the endogenous exons of the DNase I gene; and
 (c) maintaining the homologously recombinant cell produced in step (b) under conditions appropriate for the production of DNase I under the control of the exogenous regulatory sequence.

291. A DNA construct which alters the expression of a β-interferon gene in a cell when the DNA construct is homologously recombined with a target site within the chromosomal DNA of the cell, the construct comprising:
 (a) a targeting sequence homologous with a target site within or upstream of the β-interferon coding region;
 (b) an exogenous regulatory sequence;
 (c) an exon;
 (d) a splice-donor site;
 (e) an intron; and
 (f) a splice-acceptor site,
 wherein, upon integration of the construct into chromosomal DNA by homologous recombination at the target site, the regulatory sequence of (b) controls expression of a transcript comprising sequence corresponding to the exon of (c), the splice-donor site of (d), the intron of (e), the splice-acceptor site of (f), and part or all of the β-interferon coding region.

292. The DNA construct of claim 291, wherein the regulatory sequence comprises a promoter.

293. The DNA construct of claim 291, further comprising a selectable marker gene.

294. The DNA construct of claim 291, further comprising an amplifiable marker gene.

295. The DNA construct of claim 291, further comprising a second targeting sequence comprising DNA which hybridizes to genomic DNA within or upstream of the β-interferon coding region.

296. The DNA construct of claim 291, wherein the targeting sequence is selected from the group consisting of SEQ ID NO:23, SEQ ID NO:24, fragments of SEQ ID NO:23 which selectively promote homologous recombination with genomic DNA upstream of the β-interferon gene, and fragments of SEQ ID NO:23 which selectively promote homologous recombination with genomic DNA upstream of the β-interferon gene.

297. The DNA construct of claim 296, wherein the targeting sequence is a fragment of SEQ ID NO:24 and is at least about 20 nucleotides.

298. The DNA construct of claim 296, wherein the targeting sequence is a fragment of SEQ ID NO:23 and is at least about 20 nucleotides.

299. An isolated DNA molecule of at least about 20 nucleotides having a sequence selected from the group consisting of SEQ ID NO:23, a fragment of SEQ ID NO:23, and a sequence which hybridizes to the complement of SEQ ID NO:23 and which selectively promotes homologous recombination with a target site upstream of a β-interferon coding sequence.

300. A method of producing a homologously recombinant cell wherein the expression of a β-interferon gene is altered, comprising the steps of:
(a) transfecting a cell containing the β-interferon gene with a DNA construct comprising
    (i) a targeting sequence homologous to a target site within or upstream of the β-interferon coding sequence;
    (ii) an exogenous regulatory sequence;
    (iii) an exon;
    (iv) a splice-donor site;
    (v) an intron; and
    (vi) a splice-acceptor site,
    thereby producing a transfected cell; and
(b) maintaining the transfected cell under conditions appropriate for homologous recombination, thereby producing a homologously recombinant cell in which the regulatory sequence controls expression of a transcript comprising sequence corresponding to (a)(iii)–(vi) and part or all of the β-interferon gene.

301. A homologously recombinant cell produced by the method of claim 300.

302. A cultured vertebrate cell which expresses β-interferon, the genomic DNA of the cell comprising an exogenous regulatory region positioned to control expression of an exogenous exon, an exogenous splice-donor site, an exogenous intron, an exogenous splice-acceptor site, and part or all of an endogenous β-interferon gene.

303. A method for producing β-interferon, comprising the step of maintaining the cell of claim 302 under conditions appropriate for the production of β-interferon.

304. A method for producing β-interferon comprising the steps of:
(a) transfecting a cell containing a β-interferon gene with a DNA construct comprising
    (i) a targeting sequence homologous to a target site within or upstream of the β-interferon gene;
    (ii) an exogenous regulatory sequence;
    (iii) an exon;
    (iv) a splice-donor site;
    (v) an intron; and
    (vi) a splice-acceptor site,
    thereby producing a transfected cell;
(b) maintaining the transfected cell under conditions appropriate for homologous recombination in which the exogenous regulatory sequence is positioned to control expression of a transcript comprising RNA corresponding to (a)(iii)–(vi) and part or all of the β interferon gene, thereby producing a homologously recombinant cell; and
(c) maintaining the homologously recombinant cell produced in step (b) under conditions appropriate for the expression of β-interferon under the control of the exogenous regulatory sequence.

305. A method for altering expression of a targeted gene, comprising the steps of:
(a) providing a cell, the genome of which comprises
    (i) a targeted gene; and
    (ii) a target site within or upstream of the targeted gene;
(b) providing a DNA construct comprising:
    (i) a targeting sequence homologous to the target site, and
    (ii) an actin promoter from a mammalian gene;
(c) transfecting the cell with the DNA construct, thereby producing a transfected cell; and
(d) maintaining the transfected cell under conditions appropriate for homologous recombination, thereby producing a homologously recombinant cell the genome of which contains the construct-derived actin promoter positioned to regulate transcription of the targeted gene, the targeted gene encoding a protein other than actin; and
(e) maintaining the homologously recombinant cell under conditions appropriate for transcription of the targeted gene under the control of the actin promoter.

306. A cultured vertebrate cell having incorporated therein a transcription unit comprising an exogenous actin promoter positioned to control transcription of an endogenous gene other than an actin gene in the chromosomal DNA of the cell.

307. A method of altering expression of a targeted gene, comprising the steps of:
(a) providing a cell, the genome of which comprises
    (i) a targeted endogenous gene; and
    (ii) a target site within or upstream of the targeted gene;
(b) providing a DNA construct comprising:
    (i) a targeting sequence homologous to the target site, and
    (ii) a collagen promoter from a mammalian gene;
(c) transfecting the cell with the DNA construct, thereby producing a transfected cell; and
(d) maintaining the transfected cell under conditions appropriate for homologous recombination, thereby producing a homologously recombinant cell the genome of which contains the collagen promoter positioned to control transcription of the targeted gene, the targeted gene encoding a protein other than a collagen; and
(e) maintaining the homologously recombinant cell under conditions appropriate for transcription of the targeted gene under the control of the collagen promoter.

308. A cultured vertebrate cell having incorporated therein a transcription unit, wherein the transcription unit comprising an exogenous collagen promoter positioned to control transcription of an endogenous gene other than a collagen gene in the chromosomal DNA of the cell.

309. A method of altering the expression of a targeted gene in the chromosomal DNA of a cell, comprising the steps of:
(a) transfecting the cell with a DNA construct comprising:
    (i) a targeting sequence homologous with genomic DNA within or upstream of the coding region of the targeted gene;
    (ii) a non-viral promoter;
    (iii) an exon; and (iv) an unpaired splice-donor site at the 3' end of the exon, thereby producing a transfected cell;

(b) maintaining the transfected cell under conditions appropriate for homologous recombination, thereby producing a homologously recombinant cell the genome of which comprises the non-viral promoter, the construct-derived exon, and the construct-derived splice-donor site, in addition to all endogenous exons of the targeted gene; and (c) maintaining the homologously recombinant cell under conditions appropriate for expression of the targeted gene under the control of the non-viral promoter.

310. The method of claim 309, wherein the non-viral promoter is an actin promoter.

311. The method of claim 309, wherein the non-viral promoter is a collagen promoter.

312. A method of making a protein by altering the expression of a targeted gene that encodes the protein in a cell, comprising the steps of:

(a) transfecting the cell with a DNA construct, the DNA construct comprising:
(i) a targeting sequence homologous with genomic DNA within or upstream of the coding region of the targeted gene; and
(ii) a non-viral promoter which is not homologous to the endogenous promoter of the targeted gene, thereby producing a transfected cell;

(b) maintaining the transfected cell under conditions appropriate for homologous recombination, thereby producing a homologously recombinant cell in which the non-viral promoter is positioned to control expression of the targeted gene; and (c) maintaining the homologously recombinant cell under conditions appropriate for expression of the protein under the control of the non-viral promoter.

313. The method of claim 312, wherein the non-viral promoter is an actin promoter.

314. The method of claim 312, wherein the non-viral promoter is a collagen promoter.

315. An HT1080 cell into the genome of which is incorporated a transcription unit comprising an exogenous regulatory sequence positioned to control expression of a sequence comprising an endogenous gene, wherein the expression of the endogenous gene is altered compared to expression of the endogenous gene in an HT1080 cell lacking the transcription unit.

316. An RPMI 8226 cell into the genome of which is incorporated a transcription unit comprising an exogenous regulatory sequence positioned to control expression of a sequence comprising an endogenous gene, wherein the expression of the endogenous gene is altered compared to expression of the endogenous gene in an RPMI 8226 cell lacking the transcription unit.

317. A U-937 cell into the genome of which is incorporated a transcription unit comprising an exogenous regulatory sequence positioned to control expression of a sequence comprising an endogenous gene, wherein the expression of the endogenous gene is altered compared to expression of the endogenous gene in an RPMI 8226 cell lacking the transcription unit.

318. A WI-38VA13 subline 2R4 cell into the genome of which is incorporated a transcription unit comprising an exogenous regulatory sequence positioned to control expression of a sequence comprising an endogenous gene, wherein the expression of the endogenous gene is altered compared to expression of the endogenous gene in an WI-38VA13 subline 2R4 cell lacking the transcription unit.

319. A heterohybridoma cell into the genome of which is incorporated a transcription unit comprising an exogenous regulatory sequence positioned to control expression of a sequence comprising an endogenous gene, wherein the expression of the endogenous gene is altered compared to expression of the endogenous gene in a heterohybridoma cell lacking the transcription unit.

320. A linear DNA construct which alters the expression of a targeted gene in a cell when the DNA construct is homologously recombined with a target site within the chromosomal DNA of the cell, the DNA construct comprising:

(a) a targeting sequence homologous to the target site, and
(b) an exogenous regulatory sequence, wherein each end of the DNA construct has an exonuclease-generated, single-stranded overhang.

321. The construct of claim 320, wherein each of the single-stranded overhangs is a 3' overhang.

322. The construct of claim 320, wherein each of the single-stranded overhangs is a 5' overhang.

323. The construct of claim 320, wherein each of the single-stranded overhangs is between about 100 and about 1000 nucleotides in length.

324. A method of producing a protein comprising:

(a) providing an HT1080 cell containing DNA comprising an exogenous regulatory region which controls expression of a sequence encoding the protein,
(b) culturing the cell under conditions appropriate for production of the protein, thereby producing the protein, and
(c) confirming that the protein was produced.

325. The method of claim 324, further comprising the step of:

(d) isolating the protein from the cell.

326. The method of claim 325, wherein the protein is selected from the group consisting of calcitonin, insulin, insulinotropin, insulin-like growth factors, parathyroid hormone, γ-interferon, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, immunoglobulins, catalytic antibodies, protein kinase C, superoxide dismutase, tissue plasminogen activator, urokinase, antithrombin III, DNase, tyrosine hydroxylase, blood clotting factor V, blood clotting factor VII, blood clotting factor VIII, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, and soluble CD4.

327. The method of claim 325, wherein the protein is erythropoietin.

328. The method of claim 325, wherein the protein is growth hormone.

329. The method of claim 325, wherein the protein is α-interferon.

330. The method of claim 325, wherein the protein is β-interferon.

331. The method of claim 325, wherein the protein is α-galactosidase.

332. The method of claim 325, wherein the protein is glucocerebrosidase.

333. The method of claim 325, wherein the protein is FSHβ.

334. The method of claim 325, wherein the protein is G-CSF.

335. The method of claim 325, wherein the protein is GM-CSF.

336. The method of claim 325, wherein the protein is thrombopoietin.

337. The method of claim 325, wherein the protein is DNase I.

338. The method of claim 325, wherein the protein is blood clotting factor VIII.

339. The method of claim 325, wherein the protein is blood clotting factor IX.

340. The method of claim 324, wherein the sequence encoding the protein is an endogenous HT1080 coding sequence.

341. The method of claim 324, wherein the sequence encoding the protein is an exogenous coding sequence.

342. The method of claim 324, wherein the protein is selected from the group consisting of calcitonin, insulin, insulinotropin, insulin-like growth factors, parathyroid hormone, α-interferon, β-interferon, γ-interferon, nerve growth factors, TGF-β, tumor necrosis factor, glucagon, bone growth factor-2, bone growth factor-7, TSH-β, interleukin 1, interleukin 2, interleukin 3, interleukin 6, interleukin 11, interleukin 12, CSF-macrophage, CSF-granulocyte, CSF-granulocyte/macrophage, immunoglobulins, catalytic antibodies, protein kinase C, superoxide dismutase, tissue plasminogen activator, urokinase, antithrombin III, DNase, tyrosine hydroxylase, blood clotting factor V, blood clotting factor VII, blood clotting factor VIII, blood clotting factor IX, blood clotting factor X, blood clotting factor XIII, apolipoprotein E, apolipoprotein A-I, globins, low density lipoprotein receptor, IL-2 receptor, IL-2 receptor antagonists, alpha-1 antitrypsin, immune response modifiers, soluble CD4, erythropoietin, FSHβ, growth hormone, α-galactosidase, and glucocerebrosidase.

343. The method of claim 324, wherein a DNA comprising the exogenous regulatory region and the sequence encoding the protein was introduced into a predecessor of the HT1080 cell by transfection.

344. A purified preparation of glucocerebrosidase produced by a method comprising:
(a) providing a genetically engineered human cell into the genome of which is incorporated a DNA comprising an exogenous regulatory sequence positioned to control expression of a glucocerebrosidase gene, wherein said expression under the control of the exogenous regulatory sequence is altered compared to expression of glucocerebrosidase in a human cell lacking the DNA;
(b) culturing the genetically engineered cell under conditions appropriate for production of glucocerebrosidase under the control of the exogenous regulatory sequence; and
(c) isolating the glucocerebrosidase from the genetically engineered cell, thereby producing a purified preparation of glucocerebrosidase.

345. The preparation of claim 344, wherein the human cell is an HT1080 cell.

346. A composition comprising the preparation of claim 345 and a pharmaceutically acceptable carrier.

347. A composition comprising the preparation of claim 344 and a pharmaceutically acceptable carrier.

348. A fusion protein comprising amino acids 1–3 of human growth hormone signal peptide and amino acids 5–165 of human erythropoietin.

349. The fusion protein of claim 348, consisting of amino acids 1–3 of the human growth hormone signal peptide and amino acids 5–165 of human erythropoietin.

350. A fusion protein consisting of a first sequence consisting of amino acids 1–3 of human growth hormone signal peptide fused to a second sequence which is not part of human growth hormone signal peptide.

351. The fusion protein of claim 350, wherein the second sequence consists of part of erythropoietin.

352. A cultured vertebrate cell having incorporated therein a transcription unit, wherein the transcription unit comprises an exogenous non-viral promoter positioned to control expression of an endogenous gene in the chromosomal DNA of the cell, provided that the exogenous non-viral promoter alters expression of the endogenous gene compared to expression under the control of the endogenous promoter of the endogenous gene.

353. A cultured vertebrate cell which expresses a GM-CSF, the genome of said cell having incorporated therein a transcription unit comprising an exogenous regulatory sequence, an exogenous exon, and an exogenous splice-donor site, wherein transcription under the control of the exogenous regulatory sequence produces a transcript comprising RNA corresponding to the exogenous exon, the exogenous splice-donor site, and all of the endogenous exons of an endogenous GM-CSF gene, wherein the RNA corresponding to the splice-donor site directs splicing to a splice-acceptor site of the transcript which corresponds to a site within the endogenous GM-CSF gene.

354. The cell of claim 353, wherein the splice-acceptor site of the transcript corresponds to the splice-acceptor site of the second exon of the GM-CSF gene.

355. A cultured vertebrate cell which expresses FSHβ, the genome of the cell having incorporated therein a transcription unit comprising an exogenous regulatory region, an exogenous exon, and an exogenous splice-donor site at the 3' end of the exogenous exon, wherein transcription under the control of the exogenous regulatory region produces a transcript comprising RNA corresponding to the exogenous exon, the exogenous splice-donor site, and all of the endogenous exons of an endogenous FSHβ gene, wherein the RNA corresponding to the splice-donor site directs splicing to a splice-acceptor site of the transcript which corresponds to a site within the endogenous FSHβ gene.

356. The cell of claim 355 wherein the exogenous splice-donor site is operatively linked to the endogenous splice-acceptor site of the second exon of the FSHβ gene.

* * * * *

```
SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

AATTGCTCCT CGTGGTCATG CTTCT                                                   25

(2) INFORMATION FOR SEQ ID NO:2:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

CTGTGAAGGA CATGGGAGTC A                                                       21

(2) INFORMATION FOR SEQ ID NO:3:

(i) SEQUENCE CHARACTERISTICS:
         (A) LENGTH: 4488 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO:3:

```
TCTAGAGTCA GGATGGCACT GAAGGTCTCT GGGGAAGGGA CGATGATGAG AGCCCGTCAG      60

AAACCCTCCC CCCTTTCCTG GGTGATAGAG AAGACTCAGA ACTTCACGCC CGGGGCTCTT     120

TGCTCCCTAC CTGCAGCCAG GGCCCGGTGC GATGAGAGCC CCCAGACCTC CCTGAAGGGT     180

GAGTGAGTGT CACAAGTGCC ACATGCAGCT GTTCTGCCCT AAGGAGCCGC AGAGACAACC     240

GAGGCACTGC CCGCCACACC CCACAGACCT GGAGCAGAGA GACAAGAAGG CCCTACGCTC     300

AGACACTGTG CAGGCTAGGC CAATTAGGAT GCCCAGGCAG GGCTTATGAA AAAGGAACAT     360

GGAAAGGAAC CTCCAGGGTG CCCTAGGAAG CTTAAGAAAG AACGCTGGAG CCAGATGCTT     420

GGGTTCCAAT CCTGGCTGCA CCACTTCCTA GCTGTGTGAC CTTGAATCAA ATCACATTAT     480

CCTACTGAGC CTCAGTTCCC CCTTCTGTAA AATGGGCATC ATAATGTCAG TGCCTTCCTC     540

CCACTGGGCT GTGGTGAGGA CCACGGGAGG CAATGCAGAG CATGCTCTCG GCACAGTGCC     600

CAGACTGGGC AAGTGCTATA ATGGCATCA TCTCACCAGG CCTATCTTGG GTTGRGTGGG      660

CTGCAGGGTG CTCAAACAGG ACACTGCCAT TGGAGTCTGA GAAGCGGATC CTGGTAGGGC     720

GGTCCAGCCT GGGAATGAGA GGTCGGGTGA GGCCGGACTG AGCCAAAAGC AGCCCCTCCC     780

AGCTCTCCCA GTTTCCCTCC SGGCCCCGGC AGCGTGACCC CTCCTTGCTC CTTCCCCTTT     840

CTCACCGCCT GTAGGAGATA GAGAAGCGGA GGCTAGAGCG CCAGCAGCGA GACTCGGCTC     900

GTGCCACCGC CTGCGACCTC GGCCCTGTCA GCAGCGCCAC GAAGTCTGGG ACGGGAGGAA     960

GATGGCCTGA GCACTGTCAA ACGCCGCTTT GGTGGCCCAG CCTCAACCAC AACCCCGCTG    1020

TTCGCCAGCC CCCTACCCGT GTGGCCGTCA CCACGGGCCC GCTCCTCAGC GCCTGGCTCC    1080

CCGCGGTCGC TATAACTGCG ATGCTCCGGG TCCCGCGGAT ACACGAAGGA CAGGCCGCTC    1140

GGCTGCCGCT CCGAACTGCT GCGCTCTGCG GSGGGGGGGT AAGAACACGG GCTTCAGCTG    1200

GCCATGGGAA AGGCCAGTCC GACGCCCCAT CCAAGTGGCC CGGGACCTAG TATCGTGGCC    1260

CTGCCTCCCT CCCCGCAGCG GAGCAAGACT TACCCTGGGG GCAGGTCTGG CAGCAGTGTC    1320

CCGGCAGCTG GCGCGGCTGC CCACAGGCCG GGGTTGGGCA CTCTGGTTTG ATGTTCTTGC    1380

AGCTGACCCT GCCAGGCCCC TGGTACGGCG ACCCCACTGA GGCTGCTCCC GGAAAAGGCG    1440

GGAAACCCAA GTGAGTGCAA GATGCCAACT GATGAGACCC CCCAGGCAA GGATGTCCCG     1500

CAGAGTCAGC CAGCTCTGCC ACTTACAAGC TGCGTGACCC TAGACAAGCT ACTTCATCTC    1560

TCTGGGCCTC AAGGTCCCTG TCTGGAAAAT GGGGATAATA ATACTCTCTA TCTAGCAAGG    1620

CTGCCATGAG AGTTAGATGA GCAGGGAACG AAACGGAGTT GGCACAGAGC CTCACACAGA    1680

GTGGGCGATC AGTAACAGCA CCTAAGAATT GGAGGGGCTG ATTCCCCTTC CTCCACCAGA    1740

AAAATATCCC CAACATCTGC CGACTGGGCT CCTTCTCAGC AGCTCCGAGT CCACTCCGAC    1800

GCCCGCGCGA CCCGGCCGTC CCCACCCGCC AGCCCGGGCC GGCCGCGGGG TGCACTCACC    1860

GCCTCGCAGG CCACAGCACG CAGCGCATCA CCCCGAATGG CTCCCCTAGG TCCGGGTGCC    1920

ACGTCTCGTC CAAGGCATAG ACCTTCCCGC CGAAGTGCAG CCTGCGGGAC GGGCTTGGCT    1980

GGAGGCGCTG CCCAGCTCGC GCCGTGTGCC GCCCCGGGGG CTGCCCGCGG GTCCCGGGTC    2040

CCAGGCACCG CGCCCTTCTG CCCCCGCCCA CCCTCCGGGC CGCCCGCCGC GCCGAGCCAC    2100

CTGCGCCCCG CGCCCCTCCT CCGGCTCGGC TGACTCGCCC CGAGCCCGAC TCCCCGCCCG    2160

CCTCCCCCGG GCGCCCACCT ACCCTGCTGC CCGAACGGGC AGCGGCTCCT TCTCAGAACG    2220

GATGGGCAGC ACGGGGCTC TCGGGCCGCG CGGGGCGGGA GCCGAGCAGC AGCAGCCCGA     2280

GGAGCAGCAG CGGGGCCGGC GGGGCCGGGA GGGCHCGGCA TGACGCGAAC GGGACAGCTG    2340
```

```
GGGAGGAGGG AGGGAGGAGG GCGCGGGAGC GGGCGGAGGG AGGGAGGCGG GAGTGCGGAG      2400

GGCGGAGGGC CGGGCCGGGG GCGGTGCGGC GGGAGGGGGC CGGGGCCGGG GCCGGGGCCG      2460

GGGCAGTGCC CGCGAGGGGC TCGTCGGGCG GCCGCAGAGT CGGCGCCGGG CCGGGCGGGG      2520

CGGGAGGAGC GGCCGGGAGG AGCGCGGGCG GGCGGGCGCT GACCCGGGCC GTACGCGGCT      2580

CTACTGCCCC GGGCGCCGGC TCCGGCCCGT TTTATGCCCC GCGCCCGACG CCCCGGCCGG      2640

GGGCCTCCTC CTCAGCAAAC GGGGCGGCGG CGGCGGCTCG GCGAGGGGCC GCTGAGCCCG      2700

GGGGGTCCGA CCCAGCAGCA GCGGCCCGGA TCGCGGGTGG GGGAGGGGAG GGAGGGCTGG      2760

GACCGGGCAG GGGAGGAGGG AGGGGCGGGA GGGGAAGGGG GAGCGGGGGA GGGGGAGGGG      2820

AGGGACCAGG GGGCGCGAAG AGGGGGAGGA GAGGCGGCCC GGAGCCCCCG CTGCTGGCGG      2880

CCACAGGGCG GCTGGACCAG GAGGTCGGTG TCCAGCCCAG GAAGGGAGCC TCAGGCTAGG      2940

GAGGGGCAGA GGCTTACCTG AGGCCTGGAC CGCTCTGTGA GCGAGGCCCG GTTCCGCCCG      3000

AAGGATAAAC TTGTCTTTAA AGATACACGT ACAGGAAAGG TCCATCAGCC GATCTCCCCC      3060

TGCCTGGGCC CACAGCGCCC CCCAAACCCT CACCACCCTC TCTCACTGCC TAGCCTGCCT      3120

CCCTACCTTC TCTCTGAGGT CGCTCCTCWT TCTTGTGTTA CCCAGRACAG GGACCTAGCC      3180

AGAAACCGGC AGCATTCCCC CTTCTGTGGA GTGACAGTAT CTCCCTCTCA TTGTAACTTA      3240

TCCTCAGGCG CATTCGACAG TCCCCTCTTG CTTTCTCACC CCCTTCCTTC ACCCAAGGGA      3300

CCCTCTGCCT CTCCAGCCCA CTCCCAGCCT CCTTTCTCTT GGTTCCCTGG TCATGCCTGC      3360

CTCCCTGTCT CCTGTCTCTC CCTCCCACAC ACACCCACTA TCCTCCCAGC TATCCCAGCA      3420

CCCTCCTTCC TAATCTTGGG AGACATCTCG TCTGGCTGGA CGGGAAAATT CCAGGATCTA      3480

GGCCACACTT CTCAGCAGAC ATGCCCATCC TTGGGGAGGA GGAACAGGAG AGAGCCTGAG      3540

GAAGTTCTGG GGGACAGGGG GATGATGGGA TCAAGGTCAG GCCAGGAAGC CCCTGAGGAC      3600

AGAGACTGTG GGGAGACTTG GGACTGGGAA GAAAGCAAAG GAGCTAGAGC CAGGGCCAAA      3660

GGAAAAGGGG GGCCAGCAGG GWGGTATTTG CGGGGGAGGT CCAGCAGCTG TCTTTCCTAA      3720

GACAGGGACA CATGGGCCTG GTTATTCCTC TTGTCACATG TGGAACGGTA GGAGATGGAA      3780

GACGGAGACA GAACAAGCAA AGGAGGGCCC TGGGCACAGA GGTCTGTGTG TGTAGCCATC      3840

TAAGCCACTG GACCCCAGCA GACGAGCACC TAAGCTCAGG CTTAACCAGT GCACGTGTGC      3900

GCACATACTG TGCCCCGCAC CTGACGTCCA CTCAACCCGT CCAAACCCTT TCCCCATAAC      3960

ACCAACCCAT AACAGGAGAT TTCTCTCATG TGGGCAATAT CCGTGTTCCC ACTTCGAAAG      4020

GGGGAATGAC AAGATAGGAC TCCCTAGGGG ATTACAGAAA GAAAAGCAGG AAAGCAAGCA      4080

TCCTGTTGGA TTTCAGCAGC AGGTATGATG TCCAGGGAAA AGAAATTTGG ATAGCCAGGG      4140

AGTGAAAACC CCACCAATCT TAAACAAGAC CTCTGTGCTT CTTCCCCAGC AACACAAATG      4200

TCCTGCCAGA TTCCTCCTGG AAAAAACTTC TGCTCCTGTC CCCCTCCAGG TCCAGGTTGC      4260

CCATGTCCAG GAAAGATGG ATCCCCCTCA TCCAAATCTT CTCCGTGTGT GCTGTGGGTG      4320

GAGTGAGTRG WARCCCTGGT CCAGGCAGGG VGCTCCAGGG AAGAGCAAGG CGTCACTTCC      4380

GGGSGCCTTC ACCAGTGTCT GGTGGCTCCC TTCTCTGATT GGGCAGAAGT GGCCCAGGCA      4440

GAGCGTATGA CCTGCTGCTG TGGAGGGGCT GTGCCCCACC GCCACATG                  4488
```

(2) INFORMATION FOR SEQ ID NO:4:

(i) SEQUENCE CHARACTERISTICS:
        (A) LENGTH: 2455 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:4:

```
TCTTCCTACC CATCTGCTCC CCAGAGGGCT GCCTGCTGTG CACTTGGGTC CTGGAGCCCT      60

TCTCCACCCG GTGAGTGGCC AGCAGGGTGT GGGGTTATGT GAGGGTAGAA AGGACAGCAA     120

AGAGAAATGG GCTCCCAGCT GGGGGAGGGG CAGGCAAACT GGAACCTACA GGCACTGACC     180

TTTGTCGAGA AGAGTGTAGC CTTCCCAGAA TGGGAGGAGC AGGGCAGAGC AGGGGTAGGG     240

GGTGGGGTGC TGKTTTCCTG AGGGACTGAT CACTTACTTG GTGGAATACA GCACAGCCCT     300

GGCTGGCCCT AAGGAAAGGG GACATGAGCC CAGGGAGAAA ATAAGAGAGG GAGCTGCACT     360

TAGGGCTTAG CAAACACAGT AGTAAGATGG ACACAGCCCC AATCCCCATT CTTAGCTGGT     420

CATTCCTCGT TAGCTTAAGG TTCTGAATCT GGTGCTGGGG AAGCTGGGCC AGGCAAGCCA     480

GGGCGCAAGG AGAGGGTAAT GGGAGGAGGG CCCACTCATG TTGACAGACC TACAGGAAAT     540

CCCAATATTG AATCAGGTGC AAGCCTCTTT GCACAACTTG TGAAAGGAGG AGGAAGCCAT     600

GTGGGGGTC CTGTGAAGGA ACCGGAAGGG GTTCTGCCAA GGGGCAGGG AGGCAGGTGT       660

GAGCTATGAG ACAGATATGT TAGTGGGCGC CTAAGACAAG GTAAGCCCCT AAGGTGGGCA     720

TCACCCAGCA GGTGCCCGTT CCTGGGCAGC TGGTTTCAGG AAGGAAGTCC CAGAACTGTT     780

AGCCCATCTC TTGGCCTCAG ATAATGGAGT ATTTCAGGAC TTGGAGTCCA GAGAAAAGCT     840

CCAGTGGCTT TATGTGTGGG GGTAGATAGG GAAAGAATAG AGGTTAATTT CTCCCATACC     900

GCCTTTTAAT CCTGACCTCT AGTGGTCCCA GTTACAGCTT TGTGCAGTTC CCCTCCCCAG     960

CCCCACTCCC CACCGCAGAA GTTACCCCTC AACATATTGC GCCCGTTTGC CAGTTCCTCA    1020

CCCAGGCCCT GCATCCCATT TTCCACTCTC TTCTCCAGGC TGAAGCCACA ATACTTTCCT    1080

TCTCTATCCC CATCCCAGAT TTTCTCTGAC CTAACAACCA AGGTTGCTCA GAATTTAAGG    1140

CTAATTAAGA TATGTGTGTA TACATATCAT GTCCTGCTGC TCTCAGCAGG GGTAGGTGGC    1200

ACCAAATCCA TGTCCGATTC ACTGAGGAGT CCTGACAAAA AGGAGACACC ATATGCTTTC    1260

TTGCTTTCTT TCTTTCTTTC TTTCTTTCTT TTTTTTTTTT GAGACGGAGT TTCACTCTTA    1320

TTGCCCAGGC TGGAGTGCAA TGGTGCGATC TCGGCTCACC ACAACCTCCG CCTCCCAGGT    1380

ACAAGCGATT CTCCTGTCTC AGCCTCCCAA GTAGCTTGGA TTACAGGCAT GAACCACCAC    1440

ACCCTGCTAG TTTTTTTGTA TTTCGTAGAG CCGGGGTTTC ACCATGTTAG TGAGGCTGGT    1500

GGCGAACTCC TGACCTCAGG TGATCCACCC GCCTTGGACT CCCAAAGTGC TGGGATTACA    1560

GGCATGAGCC ACTGCACCCG GCACACCATA TGCTTTCATC ACAAGRAAAT GTGAGAGAAT    1620

TCAGGGCTTT GGCAGTTCCA GGCTGGTCAG CATCTCAAGC CCTCCCCAGC ATCTGTTCAC    1680

CCTGCCAGGC AGTCTCTTCC TAGAAACTTG GTTAAATGTT CACTCTTCTT GCTACTTTCA    1740

GGATAGATTC TTCACCCTTG GTCCGCCTTT GCCCCACCCT ACTCTGCCCA GAAGTGCAAG    1800

AGCCTAAGCC GCCTCCATGG CCCCAGGAAG GATTCAGGGG AGAGGCCCCA AACAGGGAGC    1860

CACGCCAGCC AGACACCCCG GCCAGAATGG AGCTGACTGG TGAGAACACA CCTGAGGGGC    1920

TAGGGCCATA TGGAAACATG ACAGAAGGGG AGAGAGAAAG GAGACACGCT GCAGGGGCA     1980

GGAAGCTGGG GGAACCCATT CTCCCAAAAA TAAGGGGTCT GAGGGGTGGA TTCCCTGGGT    2040

TTCAGGTCTG GGTCCTGAAT GGGAATTCCT GGAATACCAG CTGACAATGA TTTCCTCCTC    2100

ATCTTTCAAC CTCACCTCTC CTCATCTAAG AATTGCTCCT CGTGGTCATG CTTCTCCTAA    2160
```

```
CTGCAAGGCT AACGCTGTCC AGCCCGGCTC CTCCTGCTTG TGACCTCCGA GTCCTCAGTA      2220

AACTGCTTCG TGACTCCCAT GTCCTTCACA GCAGACTGGT GAGAACTCCC AACATTATCC      2280

CCTTTATCCG CGTAACTGGT AAGACACCCA TACTCCCAGG AAGACACCAT CACTTCCTCT      2340

AACTCCTTGA CCCAATGACT ATTCTTCCCA TATTGTCCCC ACCTACTGAT CACACTCTCT      2400

GACAAGGATT ATTCTTCACA ATACAGCCCG CATTTAAAAG CTCTCGTCTA GAACT          2455
```

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TTTTGCGGCC GCTCGAGGAC ATTGATTATT GACTAGT                              37
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTTTGCGGCC GCCGGTACTT ACGTCACTCT TGGCAC                               36
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TTTTCTCGAG GACATTGATT ATTGACTAGT                                      30
```

(2) INFORMATION FOR SEQ ID NO:8:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CATGGGTCTT TTCTGCAGTC ACCGTCCTTG CTACCCATCT GCTCCCCAGA GGGCTGCCTG      60
```

(2) INFORMATION FOR SEQ ID NO:9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CAGGCAGCCC TCTGGGGAGC AGATGGGTAG CAAGGACGGT GACTGCAGAA AAGACCCATG        60

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TTTTGGGCCC TCCTCCCATT ACCCTCT                                           27

(2) INFORMATION FOR SEQ ID NO:11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

TTTTCTCGAG GACATTGATT ATTGACTAGT                                        30

(2) INFORMATION FOR SEQ ID NO:12:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

CGCGGATTCC CCGTGCCAAG CCTAGCGGCA ATGGCTACAG GTGAGAACAC ACCTGAGGGG        60

CTAGGGCCA                                                               69

(2) INFORMATION FOR SEQ ID NO:13:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

TGGCCCTAGC CCCTCAGGTG TGTTCTCACC TGTAGCCATT GCCGCTAGGC TTGGCACGGG        60

GAATCCGCG                                                               69

(2) INFORMATION FOR SEQ ID NO:14:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

| | |
|---|---|
| TTTTGAATTC CCATTCAGGA CCCAGACCTG AAACCCAGGG AATCC | 45 |

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

| | |
|---|---|
| TGCCTTGAAG TGCTTCTTCA | 20 |

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

| | |
|---|---|
| CCTCAGAGAT GACGAGAATG C | 21 |

(2) INFORMATION FOR SEQ ID NO:17:

(i) SEQUENCE CHARACTERISTICS:
        (A) LENGTH: 4042 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

| | |
|---|---|
| GTCAACCTTC ACAGTAATTG CTTGTTCAGT GACTGCCACA ACCCAGCCTG GCAGAGAGAG | 60 |
| GGAAGATACC CTATAAAGCA AGGTAACGTT AATGTTGAGA CCATGAATGG CCTTGAGCAG | 120 |
| AGCAGAGTAT CATTGCTTCC TTCAAAATTC AGAAGGATCT GATGGTGCTC TGTGAGTTCA | 180 |
| TGGGGGTGCC TCCGTGCAGG TTGAAACCAC AGCTGTCGTC CTTCCGCTTT CCCTCTTGAT | 240 |
| CAGTAGAAGG GTACCCTCCC TGGCCTGCAC GTCGCTGGGT CACACAACAC TGGCTGTCGT | 300 |
| TGCACAAAGC CACGGCCACC AGCGTTCCTT TGAGGCCATT TGTTTCCAGC CATGGTGCCT | 360 |
| ATAGGATTTT TCCTTTATCC TGTAATTTCA GCCAAATCAG AGCATGTGAC CTGGCTTAGA | 420 |
| TGTCAATATA ATTGTTGTTA TGTGCTCTTT TCCCTTCCTG TGTCTGTGAC AGGTTTAATT | 480 |
| TAACCTGAGA AGGCTGCAGA TCCTCGGGGG TTGGTGTAAA AACACCTCAT CCTGATCTGA | 540 |
| GAAGGCGGTC AGCTTTTCTC CTCGTTGCCG TTGGCTGCCA GCACCCATTC TCTGTGGATG | 600 |
| TGAAAATCCC AGAAGGGCTG GCTTCCTTC TTGGCATTCC CCAGGCCTAT CTCCAGAGTG | 660 |
| GGGCCCAGCA TGGGAGGATT GTACCCCACT CACTCCCCTG ATGTGGGGCT GGACCTACA | 720 |
| GCTCGACAGC ACCCATGGAA TGTGGGCAGA AGCGACAGCA GCCAACGTCC GCCTTGGCCT | 780 |
| TAGGGCGGCA CGTGTTCTGC TTGTGCCCTG GGAGCCTCCA CCTTCCACAC TGTGGGAAGA | 840 |
| GGGTGCCCAG GGAGCTGCAG TCTCTCCAGC CCAGCCCCAG GACGAGGCCC AGGCAGCAGA | 900 |

```
GCCACCCCAG CAGACCTGGC AGTGTGAGAG AAATGCATGT GTATACACTG AGTTTGCAGG      960

TGGCTGTTAC ATGGCAGCAT TGACTGACAC AGACAGAAAA GAGATCCACG AGGGAGAAGT     1020

GAGAGTGCTG GAGACTCCAA CAAGCCACAG GCTGCAGGGG CAGGATGGCT TCTTAGAAGG     1080

TGAATGATTG TTCTGGGAAT CTATCAGAGG AAGACATAGA GGCTCCAGAC GGTTGAAGGC     1140

CCAACAGTGA TCCCAGACGG GCCCCATGTC AGACCAGGCT CCTCCAGGGC TGTCGCTGCC     1200

CTCACCAAAG CCCGTCCTGA GGGCAGCCAC ACAGCAGGCA GCACTCGCCA TTTGTACAAG     1260

CGAGGCCCAA GTTCCAGCCT TCCTTCTGGC AGGTAGAGGA AGCAGGGGCA CTATGCCTGG     1320

GAGTTCCTGA AAGCAGATGG GGCAGCATTT GGTCAAGAGC CAGGAGGGGA TGACAGACCA     1380

GAGGGGAACC CTCGTCCCAC GTGCTGAGCA CACGTAGGGG GTTGGGCACT TGCTCTGTGA     1440

GCTATAATTG GTGTCCCTGT GCCCCGCCGG AAGCTGCACC AGGCAGTTTC TTGGTGGAGG     1500

ACAGTGGCCG CCCTCTAGCT TTACTCCCTT CCCCGTGATG GGTCGCTGTC AGATGTGTGT     1560

CCAGGAAAGG CAAACACCAA AGGCAGAGGA CTAGTCCCTA CACCGAATAC TCCGGTGGCC     1620

TTGCTTGGGG GCTGGGTTTT GACGTGCTGG AGGCTGTCCT AGACTTAGAG ATTAAAAACA     1680

GGGAAGAACC ATTGCTGAAA CCTTTGGAAA AGCCTGCAAT GGCCTCTGGC AGCCTGAGGA     1740

GTGGTGGTGT TTCCATCTGG TAGACGCCGT CTCAATAGGA GGGACAGATG AGTGCACCAG     1800

TGCTGCCAGC CAGAGGCGTC TGTTGGCGTG TCTTTATGGA ATGGGGTGCC AGTCTTGTGG     1860

AGGGTGGTTT ACCTTCCTGT TTCTAGTCCC CACTGGGCCT GCCTTCTGCT TCATGCCAGC     1920

TGGCCAGACC GAGCACTTTC CTGACTTTCG ACCTTGGCCC CTGCTGACTC TTGCCGTTGA     1980

GGCCTCCTGC AGACCCCATT TGTATTCATT TCCTGCAGTT CTCATACCTG AATCCCGCCT     2040

GGACTTCTGC CAACCGTTCC AGGCCCTCCT CCCAGGGGGA CCACAGATGC TACGTGCAGG     2100

GCTGTCCTTG GAGGGCCAGC ACAGCCCCTT CCAAGTGGGC AAGACCCAGG GGTGGCTCAA     2160

AAGATAGCTG TGCCCTAGCC CTGGAACCTC TGAATGTTGA TTTTTGTAGC AAAAAAGGAC     2220

TTGCAGATGT GAGTAAAGGC TGTTGAGATA AGGACATCCT CCCTGCTCTC TGGGAGGACC     2280

CCAAATGCAG GTGCACAGAT CTTAAGAAGA AGAGGCAGAG ACTGGGGTGA TGCAGCCACA     2340

ACTAAGGAAA GCCAAGGATT GCTGGCAGCC TGCAGAAACT GGAGGGCAAG GAGCATCCCC     2400

CAACCGCCCG GAGCCTCCAG GAGGCGCAAG GTCCTACTGA CTCCCTGACT TCAGACGTCC     2460

AGTCTCCGGA ATTTTGAGAG GATCCATTTC TGTTATTTTA AGCAACCAAA CTTGTGGTAG     2520

TTTCACCAGT CTCAGGAAAT GAATACGAAT GGAAAGTCAA AGATTCCAAG AAATGAGTGG     2580

CGGGGTGCGG TGGCTCACAC TTGTAATCCC AGCATTTGCG GGAAGATTGC TTGGGCTCAG     2640

GACTTGGAGA CCTTGTGTCT GTGAGAAACT TAAAAAATAG GCTGGGTGCG ATCGTCACGC     2700

CTGTAATCCC AGCACTTTGG GAGGCCGAGG CAGGCGGATC ACAAGGTCAC GAGTTTGAGA     2760

CCAGTGTGAC CAACATGGTG AAACCCTGTC TCTACTAAAA ATACAAAAAT TAGCCGGGTG     2820

TGGTGGTGCG TGCCTGTAAT CCCAGCTACT CGGGAGGCTG AGGCAGAAGA ATTGCTTGAA     2880

CCCAGGAAGC AGAGGTTGCA GTGAGCCGAG ATAGTATTAC TGCACTCCAG CTGGGCAGC      2940

AGAGCAAGAT TCCGCCTCAA AAAAAAAAA AAAAAAAAA AAAAAAAAA CTGAGCATGG        3000

TAGCATGCAC CTGTGGTCCT CGTACGCCGG AGGATTGCCT GAAGCCAGGA GTTCAAGACC     3060

AGTCTGGACA AAAGAGCAAG ACCCCATCTC TACCAAAAAA ATTTAAAAAT TAGCCAGGCA     3120

TGGTGCCGTA CCCATAGTCT TAGCTACTCA GGAGGCTGAG GAGGGAGGAT TATCTGAGCC     3180

TGGCGGTTGA GGCTATAATG AGCCATGATT TGGCCACTGC ACTCCAGCCT GGCAACACA     3240

GTGTGAGACC CTGTCTCAAA AACAATAAAA ACCCAAAACA AAAGAACCAA GAAATTACTG     3300
```

```
GACCTGAGCC TGGCCTTTAG CTGCTGCCCT GCCCTKTGAC TGGTCACTCG GATCCCTGGG        3360

CCTAAACACA CAGCCTATTG TCTACCTCAA GAAGGCTCCC CACTGCTTGG CTGGCAATTG        3420

GGGTGGCTTT GCAGGCCCCA CCTGTCCTGG CCCCACGGCG CTGGTGCTGC AGGCCCCCAC        3480

CACTGCTTGT TCCGAGCTCC CCAGCCTCCT GCAGAGTTGC CTGCACCTGA TGGCGATGAA        3540

TCAGGAAGGC AGGCGTGTCC TGGGCCACAG AGCAGTCATG CTGTCAGCCA CCAGGGGGCT        3600

CCATTTGCAA CTTTGGATGT GGCTTTGGCC TCTTTGTCCA AAGTGACCTT GGGGCCCCCA        3660

GACAAGAGAC AGGGAGACTG GAGCCCAGCC CCACCCTCCC GCACATACCT GGCCCATCCC        3720

TGCCCTATCC TGGAAGATGG GGGCCACCAC ACGTRCAAGG GACACGGGAT AGGAACCTTT        3780

GGCCTTGTTA TCAGACATTT TAAAACTAAG TGCAAACGTG ATTATCAGGT GCAGTTTTTA        3840

CAGCAGCAAG AAACCTGTGC TTACAGAAAG AAACACGTGC TAGCAACCCA CCTATGCGGA        3900

AAGCCACACA GAGCCATTGT TTTCTGCACT CTCAGGTGAC GGCTCACATT TGCCCCAGGG        3960

AAGGTCACAG CTGCCTGAAC TTTTAAAACT CCCAGACACG CACTGCCTGT GCAGGATCCG        4020

GAGCCCAGCA GCACTGCCAG GG                                                4042

(2) INFORMATION FOR SEQ ID NO:18:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 471..810

(xi) SEQUENCE DESCRIPTION: SEQ ID NO:18:

CCTTGAAGTG CTTCTTCAGA GACCTTTCTT CATAGACTAC TTTTTTTTCT TTAAGCAGCA          60

AAAGGAGAAA ATTGTCATCA AAGGATATTC CAGATTCTTG ACAGCATTCT CGTCATCTCT         120

GAGGACATCA CCATCATCTC AGGTGAGCAC CAGGTGGAGT GCCTCTGGGT GACTGGCCGG         180

TTTGGAGCAG GGAGGGAGGC TTAGAGTCTC ATCCTCCAGC AGCGAGTGAG GCGGAGGCTC         240

CAGCGTCCTC CCGGGCGGGT TTTCTGGTGG ATGGAGGAGT GACTCGGGGT CCTCTACGTG         300

GTGCCAGCTG TTTGGCTTTC TGGACGTTGT AGGAAAGGGT TTCCCCCGCC TGCGTCCCCC         360

TGACCTTGAG CTCCACCAGC CCTGCCAGCC TGGGCTCCAG AAGGCTGGAG TGCTGTGGCA         420

GGGATGACGT CTCACTTCTG TTATGTCTCT GTGCCCTGTG CTCTCCCAGG ATG AGG            476
                                                         Met Arg
                                                           1

GGC ATG AAG CTG CTG GGG GCG CTG CTG GCA CTG GCG GCC CTA CTG CAG           524
Gly Met Lys Leu Leu Gly Ala Leu Leu Ala Leu Ala Ala Leu Leu Gln
      5                  10                  15

GGG GCC GTG TCC CTG AAG ATC GCA GCC TTC AAC ATC CAG ACA TTT GGG           572
Gly Ala Val Ser Leu Lys Ile Ala Ala Phe Asn Ile Gln Thr Phe Gly
 20                  25                  30

GAG ACC AAG ATG TCC AAT GCC ACC CTC GTC AGC TAC ATT GTG CAG ATC           620
Glu Thr Lys Met Ser Asn Ala Thr Leu Val Ser Tyr Ile Val Gln Ile
 35                  40                  45                  50

CTG AGC CGC TAT GAC ATC GCC CTG GTC CAG GAG GTC AGA GAC AGC CAC           668
Leu Ser Arg Tyr Asp Ile Ala Leu Val Gln Glu Val Arg Asp Ser His
              55                  60                  65

CTG ACT GCC GTG GGG AAG CTG CTG GAC AAC CTC AAT CAG GAT GCA CCA           716
```

```
Leu Thr Ala Val Gly Lys Leu Leu Asp Asn Leu Asn Gln Asp Ala Pro
            70                  75                  80
GAC ACC TAT CAC TAC GTG GTC AGT GAG CCA CTG GGA CGG AAC AGC TAT        764
Asp Thr Tyr His Tyr Val Val Ser Glu Pro Leu Gly Arg Asn Ser Tyr
            85                  90                  95

AAG GAG CGC TAC CTG TTC GTG TAC AGG CCT GAC CAG GTG TCT GCG G          810
Lys Glu Arg Tyr Leu Phe Val Tyr Arg Pro Asp Gln Val Ser Ala
            100                 105                 110
```

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
GACATTGATT ATTGACTAGT T                                                 21
```

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
TTTAAGCTTC TGCAGAAAAG ACCCATGGAA AG                                     32
```

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
TGCTCTGGCA CAACAGGTAG                                                   20
```

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
CATAGATGGT CAATGCGGC                                                    19
```

(2) INFORMATION FOR SEQ ID NO:23:

(i) SEQUENCE CHARACTERISTICS:
        (A) LENGTH: 8355 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
AGCTTCTGCT TTAGGAAAGT AGAAAAATAA GAGCAAATTA AATCCAAGGT AAGTAAAAAA      60

AAAAAAAAAA AAAAAAAGAA ATAAAAATTA GAGCAGAAAT CAATAAAATT GAAGACAGTA     120

AATCAATAAA GAAAATCAAC ATAAAAAGTC TGGTTCTTGA AAAGATATAT AAAATTGATA     180

AGCATCTACC TAGGATAATT AAGGAAAAAA GACAGAGGAC ACAGATTACT AATATCAAAC     240

ATAAAAGCGG GAACATCACT GCAAATTTTA TAGGCATTGA AAGCGTAATA AAAGAATACT     300

ATAAACTATT CTATAACTAC AAATTTGATA AGTAAATAGA ATGAACCAAT TCCTTGAAAG     360

ACATAATCTG AAAATGTAA AAAGAAGAAA TAAACAATCT GAATAGCCTA TATCTATTAA      420

ATAAATTGAA TCAGTAATTA ATAACCTCTC AAAACAGGAA GCACAATGCC CAGATGGGTT     480

CACTAGTGAA TTCTATCAAA TATTTAAAGA AAAAAAAATT GTATCAACTT TCTACAATCT     540

CTTTCAGAAG ACAGAAGCAG AGGGAATACT TCCTAAATCA TTCAACTAGG CCAGCATTAC     600

CTTAATACCG GAACTAGAAA ATGACATTAC AAGAAAAGAA AACAACAGAC CAATATCTCT     660

CATGAACAAA GATACAAACA TTTTCAACAA AATATTAGCA AAAAGAATCC AAGAATGTAT     720

CAAAAAATAT ACACCACAAC CAAGTAGAAT TTATTCCAGA TATGTAAGGG TGGTTCAACG     780

TTTGAAAATC AATTAACGTA ATTTGTCCCA TCAACAGGTT AAAGAAGAAA ATCACATGGT     840

CATATTGATA GACACAGAAA AAGCATTTGA CAAAATTTAA CACCCATTCA TGATGCAATC     900

TCTCAGTAAA CTAGGAATAG AGGAAAACTT CCTCAGCTTG AATGTACCTT CCTCTCAATT     960

TTGCTATGAA CCTGAAACTC CTCTTAAAAA ATAAAGTTTT TCATTTAAAA AGAAAACAAA    1020

AAACATGGAG GAGCGTTGAT GTATCTCATT TTAGACCAAT CAGCTATGGA TAGTTAGGCG    1080

ACAGCACAGA TAGCTGCTGT ACTTCTGTTT CTGGCAATGT TCCAGACTAC ATTTAAAAAA    1140

TTTTTAATTA TAGACTTGTA CTTAATGTTC AAGAAAAATA TGAAAATGCT TTGCCGTGTT    1200

AATGCTACTC TTTTTTAAAA AAAACTAAAG TTCAAACTTT ATTTATATTT CATTAGTTTT    1260

TTAGCTACTG TTCTTTTTCT GTTCTGGGAT CTCATTCAGA ATGCCACATT ACATATAATT    1320

CTCATGTCTC CTTGGGTTCC TCTTAGTTTT GACAGTTCCT CAGACTTTTC TTATTTTTGA    1380

TGACCTTGAC AGTTTTGAGG AGTACTGGTT AGATATAGGG TAATGGTTTT TAAAGTATAT    1440

TTGTCATGAT TTATACTGGG TAAGGGTTTG GGAGGAAGCC ATGGGTAAGT ACTGTTCTCA    1500

TCACATCATA TCAAGTTATA TACCATCAAT ATTGCCACAG ATGTTACTTA GCCTTTTAAT    1560

ATTTCTCTAA TTTAGTGTAT ATGCAATGAT AGTTCTCTGA TTTCTGAGAT TGAGTTTCTC    1620

ATGTGTAATG ATTATTTAGA GTTTCTCTTT CATCTGTTCA AATTTTGTCT AGTTTTATTT    1680

TTTACTGATT TGTAAGACTT CTTTTTATAA TCTGCATATT ACAATTCTCT TTACTGGGGG    1740

TGTTGCAAAT ATTTTCTGTC ATTCTATGGC CTGACTTTTC TTAATGGTTT TTTAATTTTA    1800

AAAATAAGTC TTAATATTCA TGCAATCTAA TTAACAATCT TTTCTTTGTG GTTAGGACTT    1860

TGAGTCATAA GAAATTTTTC TCTACACTGA AGTCATGATG GCATGCTTCT ATATTATTTT    1920

CTAAAAGATT TAAAGTTTTG CCTTCTCCAT TTAGACTTAT AATTCACTGG AATTTTTTG     1980

TGTGTATGGT ATGACATATG GGTTCCCTTT TATTTTTTAC ATATAAATAT ATTTCCCTGT    2040

TTTTCTAAAA AAGAAAAAGA TCATCATTTT CCCATTGTAA AATGCCATAT TTTTTTCATA    2100

GGTCACTTAC ATATATCAAT GGGTCTGTTT CTGAGCTCTA CTCTATTTAT CAGCCTCACT    2160

GTCTATCCCC ACACATCTCA TGCTTTGCTC TAAATCTTGA TATTTAGTGG AACATTCTTT    2220
```

```
CCCATTTTGT TCTACAAGAA TATTTTTGTT ATTGTCTTTT GGGCTTCTAT ATACATTTTA    2280

GAATGAGGTT GGCAAGTTAA CAAACAGCTT TTTTGGGGTG AACATATTGA CTACAAATTT    2340

ATGTGAAAAG AAAGTATACC TTCACAATAT TAAGTCTTTT AGTTCATGAA TATAGTATGT    2400

CTCTCCGTTT CTGCATTAAC TTAGACATTC ATTAATTTCT CTCACAATTT ATAAGTTTAT    2460

TTAGATCTTC ATTCATTTAA ATCTTCACTA ACCTCTCATT TACAATTTGT AAGTTTTCTG    2520

GGTAACAGTC TTGCACTTCT TTGCCTAGAT TTATTTCCAA GTAGATTATT TTCATACATC    2580

GTCTATGGTG TCATTTTTAA AATGTAATTT TTCACCTTTT TATTGCTAAA GAGAGATGAC    2640

TGATTGTTAA TATTGATCTT GTGCGTGGCG ACCTTGCTGA ATTCTAATCG TTTATCTATA    2700

AATTCTTTTG TATTTTGAAT GTAAACAATT AGATCATCTG CATATAATTT TTAAAATCTG    2760

ATAAGTCAAC AAGAGATTGA ACAGGCTCT TCACAAAGAA AATATCCAAA TGGTCAATAA    2820

ACATATGAAA AGATGCTGAA ACTTGTTAAT AATCAGAGAG ATGCAAATTA AACTATAATG    2880

AAGTATTATT GTACAACAAT AGAATGACTG AAATTAAAAA GACTGACAAT ATCAAAGTTG    2940

GCAAGAGTCT GATACAACTG GAACTTCTCA AACACTGTTA GTAAGAATGT AAATTGGTAC    3000

AAACATTTGG GAAGTCATTA CAATATTATC TGCTAAATCT GAACATATAC ATATTCTATG    3060

AGCCAGTTAC TTCATTCTAG GCATATACCC AAAAGAAGTA TGTACTATTG TGCAGTAAAA    3120

AATACAGACA AGGAATTTCA TAGGAGCATT AATTATCATG GCAAATATTT TAAAAAATTA    3180

TTAGTAGTAG AAGGGATAAA ACATTGTGGT ATACTTCTAA ATAGGGTAAA ACACATTAAT    3240

GTAAATTAAT AAACTATACA CACAAGATAG ACGAATTTCG CAGACATTCT GTTGAGGGTA    3300

AGAAGACCAT TTATACAAAG CTCAAAAACA GACAGAATCT AGAGTGTTAA AAGACTGCAT    3360

GGTAGTGACT TTGGGAGAAG AAAGTAGTGA CGAGAGAGAG GAGAGAGAAT AATGATTGCG    3420

AGGTGCTATA GTCTGAAGGT TTGTGTCCCC CAAATTTCAC ATGTTAAAAC CTAATCCCCA    3480

ATGCAATCAT TTTAAGAAGT GGGTCCTTTA GTGGATAATT AGGTAATGGA ACAAGAGCCC    3540

TAACAAATGG GATTGGTGCC TTATAAAAGA AGCCTGAGCC TGAGGGACCT TGTTTCCCGC    3600

TTCTACCATA TGAGAATGCA ATGAGAAGGC ACAAAGCAAA GAGCAAGCCC TCATCAGACA    3660

CTGAATCTGC TAGGGCCTTA GTCTTGGCTT TTCCAACCTC CAGAACTATA AAAAGAAATG    3720

CTTGTTGTTT AAAAGGCATT CAGTCTATCG GTGTTTTGTT AGAGCAGCCC CAAGAGACTT    3780

AAGAGGGAAC AAGAGGGCGA TTTCTGTTGT GTTGATAATG TTTAGTTTGT GGTTACAAAG    3840

AGTGCAGACG TTTTTATTTT ATAACAATTC ATTGAGCTAT ATCTTAAGAT GTATGCGTAA    3900

TTTTCTATGT ATATTATTGT TTTATAAACT TTTTCTTAAA AGAGGAAATG GGAATTCTCC    3960

CTTTTATGTA TTAATCTCTT ATGAAAGAGT TTGTTGGCTT CCCAAGATAT TTCTGAAAGA    4020

TTGCTTTTGG CTTCATTTAT GTTCTGCCAC TGCTTATGCA CCTCTCAATA ACTCTTCATC    4080

TTGTATAATT TATCATTCTT TGATAGGGAC CCTCTTCCTT GAAAAATAAT TGAAGATATA    4140

AGGAGGAGGA AGAGAAGACA ACTAAATGTT TATTTCTAGA TACATAGTAG TCTGCATAGA    4200

TAATTATATT CAAAAGAGGA GGACAAATTG GCTCCTATCT CTGAAATTTA TAGAAAAGCA    4260

TTTCCACATT AAAGTGATTT CAAATGACTA GAAATGTCAT TCAAGTTTTA CTTTCTAAAT    4320

GTCACTCTGT CTCTCCAAAC CTCATTAACC ACAAGGAACT GGTGCAGGGA CTGGAAGTAG    4380

TTTTCTCATA CAACGGAAAG TTAACGAGGG GAGGAAAGGA TGTGTGCAAA AATAACGTCC    4440

ACAGAAGGGA CAAATAACAA AGGGAAAGAT GACAGGAAAG GGTTCGGGCA CTAACCCTTA    4500

CAATGCAGAT ACACACTGGG CTGGTCTAAG AAATAGGGTT CCCTGGTAGA CAGAAGGTTA    4560

AATAAATTTT CCTGGTTATT CTGATACAAC TCTAATAAAA GAAGAGAAAT GAAGCTAAAA    4620
```

```
CTTAAAATGA TGTATTTAAA AGGAAGAAAT TTTAACCCAT TCATAGGTGA GCTTCTGCCA    4680

AGATTACTAC TAATCCTCAG GAGAAGGGGT AGAGGAGAAA CTCCATAAAG GCAACTGGAA    4740

GTGGAGTATT AGGAAGCACC TCAAGAACAC AATAGCAGGA AGTAGCTAGA GAACAAAGAG    4800

AAGAAAACCA GAAAAAAAAA ATCCCTTTTT ATTTTTCTGT TTCCATTCCT TTGGCTCCAT    4860

TTCCACAGCT ATGGCCTTTA TTTTCACCCT CCACAGCCAT GAGAGCCTCT GGGCAGGAGT    4920

TCTCCTCGCC TCTCCCTGTT CCAATCACCT CTAACATTTC TGCCTATTGT TCTGCCCAGG    4980

GAAAAAACTC CAGTCTCTTC TCTGTCAAAG ACCTCTTGAA TTAAGTCCAA ATGCTACACT    5040

CTGGCATTCA AGACTCGTAA TACAGCTCAA CCTGACTTTT CCACCCTCAG CCTCCTTGAT    5100

TCCTAAAATG AAGCCTGTCC ACAATTGAAG CTCCTTGTCT TTGCTCCTGC AAATTTGTTC    5160

ATTCTCCTGG CTGTGTTTGT GCTGGTCTCT GTCTATCTAG AGCTGTGGAT ATCATGGTAT    5220

CTATTGTCTA TCATGCTAGC CATGAACCAC ATGTGGCTGG TGAGCATTTT ATATGGTACT    5280

AGTCTAAATT GACATCTACT GTGAGTGTAA AAATGTGCAT TATGTTTTGA AGACTGTACA    5340

CAAAATTTAA TTATCTCATG AATAATTTTA GATTGGTTAT ATGTTGAAAT TATAATATTT    5400

TGGATATACT ATGCTAAATA AAACATATTA TTAAAATTAA CTTCACCTGT TTCTTTTCCT    5460

CTTTCAATAT GGCTACTAGA GCTTTTTAAA TTGCATTATG TGACTTTATT GGACAGTACC    5520

GATTGAATGC CCTCAACCAC ATCACCTCAC CACAGCCACC TCTACCTGTA GTGATCATAC    5580

CACTTCTTTA GGCACACTGC CTGCATTAAG GGCAATGAAT GCCTTTTCAT CTTCTCCACT    5640

AGATGTAGTT TCTTTTTTCT TTGAGAGCCA TCATCACCAT CATGGTTGAC ACCATGAACC    5700

TATCTGAAGA TGTCAGCCAT AGACTGCTTG ATATTCTACA GGAAAGATCA CAGTTTTAAG    5760

TGCAATCTAC CCATGTTATT AGCAGTGTGT ATCTTTCACA CATTACACAG CCTCTCTAAG    5820

CCTCATTTCT CTCCTCTGTA AGATGGGGAT GATAATAACC CATCTCAAAT GTTTACTATG    5880

AGGATTATTC AAAGAATGGC AAATAGCAAG TGCTTAATAA ATGATAACTA GTACTACCGC    5940

CACTACTGTT GTTTTTATTG TATTAGATTA TGAACTCTCT AAGGACCATT TCCGGATGGA    6000

GGATAAGAGA CCATTTGATG TGGGCAGTGA TGAGGCCTTC TGTTGCACCT GGAAAGGTCA    6060

ACTATATACA AGCCTGCAAG TCATTCTATA GGAGCAGGCC CCAGTGACCA GACTCTATAG    6120

ACTGTCTCCT CTTTCCTGAG AGGGACAGCC ATCTCTAGGT TGACTAACCT CTGAAGCTCC    6180

TTGCATTGGC TTTTGTGCTA TGAGCCATGG ATGATTCCAG ACTAATCCGA GAATGCTCGT    6240

CAAAACCCCA AGGAATTACT CAAATACTGA CATAACAGAC ATTTTTGAGT GGAAGAGCCG    6300

AGTTTTTTTT AATATTCTGA AACTCATTGT TTTTAAAATG CATGAGATGG CCAAGGTCTT    6360

GCTAAGAGCT GGCCTGCAAA GCGAAAGGCA GAGAGAATGA AACCCATAGA GAGGCAGAAT    6420

AACCAGAAAG GTTGGGACTC GTTTATTTTA TAATGTAAAT TAGTCTATTA TGAAACAATA    6480

CTTGTTTACT GGTGGAAAAT TGGAAAATAC AAAGAATAAA AGGAGGAAAA AAATCACTCT    6540

TTAGTTTCAC AAGCCAAATC AAGCCACTAT TAAAATGGTG GTTTACTTCC TTTTATTAAT    6600

TTTCTGTACA TATTTTTGCA TAATCATGTT GTATGTACAA TTTTATGTTC TATTTTTCAA    6660

TATTAACTGG TGTCTTTCAA ATTTCCTAAT GACAAAAATA ATATATGCTC ATAATAGAAC    6720

ATTTAAATG CAAATAAAAC AAAATAAATG TTAAATTTA GTAATATTTA TTAAATTTTC     6780

TCCAAGTGCA CGAAATTACA AATGTAACAA CCTAATTCCC TAGTGGCCTA ATAACCCTAT    6840

TTCCAGACCT CTTCTCATTA CAAGGAAAAA CTCATATGCA GATAGTTCTA AAGGTATGAA    6900

GTGAAAAGAT AAAGATTTTT CTTCCTTGCT GCATCCTCAC CCCATCAGCA TTATTCCCCA    6960
```

-continued

```
GGGTAACTAC TATTAATAGA TAGTAATTCT ACCCAAAGGA AAAAATCATA TGCATATAAC      7020

AGCATCATAT GTATACCTTT CTAGTAACTT ACAAAACAAA TGATAATATC ATATCCTTTC      7080

TTATGTGTAT TGCTCTTTTC ACTAAATGTA TCTGTGATAT GTGTCTATAT CAGCTGATTG      7140

TCCTTTTTGA TGGCTGAATA ATATTCCATC TTGTCCACGT GATAGTATTA CTTGACAAGC      7200

TCCCTGCTGA TGGACATTTG TCTTTGTTAC TATGATAGTA ATATAATCAA CATTTATATA      7260

TGTTTTGTAT GTATCTATAA TACACATGCA CATACACATG CATATTTCTG CAGGGATAGC      7320

CATAGTAAAT AACTAGTAAC GGTATTGCAA GTTAAAGGAA CAATCTCATT GCTTGAAATT      7380

TTAAATTTTG AAATACACTG CCAATTTTCA TGGTCTCTCC TTGTAAGCTA GTTTGGGCTT      7440

TCTCACAGCA TGACAGGCTC AGGGCAGTCA GACCATCCTG GCCAAAGAGC AGAGTGCCAC      7500

AGACCACAAC TGCTTCTAAT CAGCCATCTT CCCAAAGCCT TCTCTTTTTT CTATTAATAA      7560

CTTTGTATGA GATTCCATCT TAATACTTTT CTGTTGTTTG GTCTTGTAAG AGCTTATTTT      7620

TCTGAACCAG GAAGTGGTTC AGGGCGGTTT TTCTAACTTC ACAGAGCTCC CTCTTCTGTT      7680

AGCTTTTGTG AAATGGTCAA AAACATAGCA GCCTGCCTTC TGAGTTCTCC ATCCCACCCT      7740

GGTTGGGCCT TCTCTATCCT TGTCTGTGTT GTTTATATCC TGCTGAAGTG TGATTCCACT      7800

TGTGCAGTTT CTCCTCTGTG TAGGATCAAA AGGGCTGTGG CTGGTTGGTT TGAAAATTTC      7860

TTATACCCTA GACTATTCCA GTGCCTTTCA GAAGTTTCCA AGGCCCTCTC ACACTAATCT      7920

ATTATCATAT TGGGCAAAAC TCCTTGCAGT TTCAGCTACT ATTCCCTGAT TGACTTTTCA      7980

GTAAATCTAT CTCTCAGTCT TTCAGTATCC AAAGAAGATT GGTTCTAGGA CCACCATCCC      8040

GCTGCCTCCA CAGATACCAA AATCAGAGGA TGCTCAATTC CCTCTTATAA AACGTTGCAG      8100

TATTTGCATA TAATCTGCAC ATGTATTTCT GTATATTTTA AATCATCCCT AGATTACTTA      8160

TAATACCTGA TACAATATAA ATGCTAAATA GCTGTAACAC TGTATCTTTA AAATTTACAT      8220

TATTTTTTGT TGTTGTATTA TTATTTTTAT TGTATTTTTA AAAAATATTT TCCATCTACA      8280

GTCAGTAGAA TCCACGGATA CAGAACCTAT GGATAGGAAG GACCAACTGT ATCTTTTAGT      8340

GTTTTGAGGT TCTTG                                                      8355
```

(2) INFORMATION FOR SEQ ID NO:24:

(i) SEQUENCE CHARACTERISTICS:
        (A) LENGTH: 1584 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: mat_peptide
        (B) LOCATION: 357..917

(xi) SEQUENCE DESCRIPTION: SEQ ID NO:24:

```
AATTCTCAGG TCGTTTGCTT TCCTTTGCTT TCTCCCAAGT CTTGTTTTAC AATTTGCTTT        60

AGTCATTCAC TGAAACTTTA AAAAACATTA GAAAACCTCA CAGTTTGTAA ATCTTTTTCC       120

CTATTATATA TATCATAAGA TAGGAGCTTA AATAAAGAGT TTTAGAAACT ACTAAAATGT       180

AAATGACATA GGAAAACTGA AAGGGAGAAG TGAAAGTGGG AAATTCCTCT GAATAGAGAG       240

AGGACCATCT CATATAAATA GGCCATACCC ACGGAGAAAG GACATTCTAA CTGCAACCTT       300

TCGAAGCCTT TGCTCTGGCA CAACAGGTAG TAGGCGACAC TGTTCGTGTT GTCAAC          356

ATG ACC AAC AAG TGT CTC CTC CAA ATT GCT CTC CTG TTG TGC TTC TCC        404
Met Thr Asn Lys Cys Leu Leu Gln Ile Ala Leu Leu Leu Cys Phe Ser
```

```
        1               5                10               15
ACT ACA GCT CTT TCC ATG AGC TAC AAC TTG CTT GGA TTC CTA CAA AGA     452
Thr Thr Ala Leu Ser Met Ser Tyr Asn Leu Leu Gly Phe Leu Gln Arg
                    20                25                30

AGC AGC AAT TTT CAG TGT CAG AAG CTC CTG TGG CAA TTG AAT GGG AGG     500
Ser Ser Asn Phe Gln Cys Gln Lys Leu Leu Trp Gln Leu Asn Gly Arg
            35                40                45

CTT GAA TAC TGC CTC AAG GAC AGG ATG AAC TTT GAC ATC CCT GAG GAG     548
Leu Glu Tyr Cys Leu Lys Asp Arg Met Asn Phe Asp Ile Pro Glu Glu
        50                55                60

ATT AAG CAG CTG CAG CAG TTC CAG AAG GAG GAC GCC GCA TTG ACC ATC     596
Ile Lys Gln Leu Gln Gln Phe Gln Lys Glu Asp Ala Ala Leu Thr Ile
65                70                75                80

TAT GAG ATG CTC CAG AAC ATC TTT GCT ATT TTC AGA CAA GAT TCA TCT     644
Tyr Glu Met Leu Gln Asn Ile Phe Ala Ile Phe Arg Gln Asp Ser Ser
                    85                90                95

AGC ACT GGC TGG AAT GAG ACT ATT GTT GAG AAC CTC CTG GCT AAT GTC     692
Ser Thr Gly Trp Asn Glu Thr Ile Val Glu Asn Leu Leu Ala Asn Val
            100               105               110

TAT CAT CAG ATA AAC CAT CTG AAG ACA GTC CTG GAA GAA AAA CTG GAG     740
Tyr His Gln Ile Asn His Leu Lys Thr Val Leu Glu Glu Lys Leu Glu
        115               120               125

AAA GAA GAT TTC ACC AGG GGA AAA CTC ATG AGC AGT CTG CAC CTG AAA     788
Lys Glu Asp Phe Thr Arg Gly Lys Leu Met Ser Ser Leu His Leu Lys
130               135               140

AGA TAT TAT GGG AGG ATT CTG CAT TAC CTG AAG GCC AAG GAG TAC AGT     836
Arg Tyr Tyr Gly Arg Ile Leu His Tyr Leu Lys Ala Lys Glu Tyr Ser
145               150               155               160

CAC TGT GCC TGG ACC ATA GTC AGA GTG GAA ATC CTA AGG AAC TTT TAC     884
His Cys Ala Trp Thr Ile Val Arg Val Glu Ile Leu Arg Asn Phe Tyr
                    165               170               175

TTC ATT AAC AGA CTT ACA GGT TAC CTC CGA AAC TGAAGATCTC CTAGCCTGTG   937
Phe Ile Asn Arg Leu Thr Gly Tyr Leu Arg Asn
            180               185

CCTCTGGGAC TGGACAATTG CTTCAAGCAT TCTTCAACCA GCAGATGCTG TTTAAGTGAC    997

TGATGGCTAA TGTACTGCAT ATGAAAGGAC ACTAGAAGAT TTTGAAATTT TTATTAAATT   1057

ATGAGTTATT TTTATTTATT TAAATTTTAT TTTGGAAAAT AAATTATTTT TGGTGCAAAA   1117

GTCAACATGG CAGTTTTAAT TTCGATTTGA TTTATATAAC CATCCATATT ATAAAATTGC   1177

CAAGTACCTA TTAGTTGTTC TTTTTAAAAT ATACCTGCAA AGTAGTATAC TTTCTGGCCC   1237

CTGCCTTTAA GGAATTTAAA ATTCAAGAAA GCCATGATGG AATATATAAG GTAAGAGACA   1297

ATAAGGGGAC CTGAACCTTA TGGGGAATAA AATATGGCAT GAACTGCTGT GGGATTAAAA   1357

GAGAAAAGGA AAGCTGGAGG GTCTGGAACT AAACCTGGGG TTCCCATTCC TCCTACTGTG   1417

TGTTCCAGAT TCTCTCATCA TAAAGTTAGA ATTGAGCTGG CCATCAGGAA TAGCCAGAGG   1477

AATATGTCAG CTTTTGTGTT CTCCCTAACC TTCCCCAGTT ATTTGGGGGA TCACTTTGCT   1537

CCTCGAAAGA TTTTTAAATA ATTATGTGCC CCCCACCATC CCTGCAA                1584
```

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGACATAGGA AAACTGAAAG G                                                      21

(2) INFORMATION FOR SEQ ID NO:26:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:26:

TTTGGATCCG TTGACAACAC GAACAGTGTC G                                           31

(2) INFORMATION FOR SEQ ID NO:27:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:27:

TTTCCCGGGA CATTGATTAT TGACTAGTT                                              29

(2) INFORMATION FOR SEQ ID NO:28:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:28:

CGTGTCAAGG ACGGTGACTG C                                                      21

(2) INFORMATION FOR SEQ ID NO:29:

(i) SEQUENCE CHARACTERISTICS:
         (A) LENGTH: 113 amino acids
         (B) TYPE: amino acid
         (D) TOPOLOGY: linear (ii) MOLECULE TYPE: protein (xi) SEQUENCE DESCRIPTION: SEQ ID NO:29:

Met Arg Gly Met Lys Leu Leu Gly Ala Leu Leu Ala Leu Ala Ala Leu
 1               5                  10                  15

Leu Gln Gly Ala Val Ser Leu Lys Ile Ala Ala Phe Asn Ile Gln Thr
             20                  25                  30

Phe Gly Glu Thr Lys Met Ser Asn Ala Thr Leu Val Ser Tyr Ile Val
         35                  40                  45

Gln Ile Leu Ser Arg Tyr Asp Ile Ala Leu Val Gln Glu Val Arg Asp
     50                  55                  60

Ser His Leu Thr Ala Val Gly Lys Leu Leu Asp Asn Leu Asn Gln Asp
 65                  70                  75                  80

Ala Pro Asp Thr Tyr His Tyr Val Val Ser Glu Pro Leu Gly Arg Asn
                 85                  90                  95

-continued

```
Ser Tyr Lys Glu Arg Tyr Leu Phe Val Tyr Arg Pro Asp Gln Val Ser
            100                 105                 110

Ala (2) INFORMATION FOR SEQ ID NO:30:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:30:

Met Thr Asn Lys Cys Leu Leu Gln Ile Ala Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
            35                  40                  45

Leu Glu Tyr Cys Leu Lys Asp Arg Met Asn Phe Asp Ile Pro Glu Glu
        50                  55                  60

Ile Lys Gln Leu Gln Gln Phe Gln Lys Glu Asp Ala Ala Leu Thr Ile
 65                 70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185
```